US012658295B2

(12) United States Patent
Gallopyn et al.

(10) Patent No.: US 12,658,295 B2
(45) Date of Patent: Jun. 16, 2026

(54) AUTOMATED CLINICAL DOCUMENTATION SYSTEM AND METHOD FOR SYNCHRONIZING MACHINE VISION AND AUDIO ENCOUNTER INFORMATION

(71) Applicant: Microsoft Technology Licensing, LLC., Redmond, WA (US)

(72) Inventors: Guido Remi Marcel Gallopyn, Newburyport, MA (US); Dushyant Sharma, Woburn, MA (US); Uwe Helmut Jost, Groton, MA (US); Donald E. Owen, Orlando, FL (US); Patrick Naylor, Reading (GB); Amr Nour-Eldin, Toronto (CA); Daniel Paulino Almendro Barreda, London (GB); Mehmet Mert Öz, Baden (AT); Garret N. Erskine, Torrance, CA (US)

(73) Assignee: Microsoft Technology Licensing, LLC., Redmond, WA (US)

(*) Notice: Subject to any disclaimer, the term of this patent is extended or adjusted under 35 U.S.C. 154(b) by 1052 days.

(21) Appl. No.: 17/210,292

(22) Filed: Mar. 23, 2021

(65) Prior Publication Data

US 2022/0051772 A1      Feb. 17, 2022

Related U.S. Application Data

(63) Continuation-in-part of application No. 16/058,826, filed on Aug. 8, 2018, now abandoned.
(Continued)

(51) Int. Cl.
*G16H 15/00* (2018.01)
*G06V 20/52* (2022.01)
(Continued)

(52) U.S. Cl.
CPC ............. *G16H 15/00* (2018.01); *G06V 20/52* (2022.01); *G10L 21/0208* (2013.01);
(Continued)

(58) Field of Classification Search
CPC ........ G16H 15/00; G16H 10/60; G16H 20/10; G16H 40/20; G16H 40/67; G06V 20/52;
(Continued)

(56) References Cited

U.S. PATENT DOCUMENTS 5,357,427 A      10/1994  Langen
7,298,930 B1*    11/2007  Erol ....................... G11B 27/28
                                                             707/999.001
(Continued)

FOREIGN PATENT DOCUMENTS

CN        102551762 A       7/2012
WO      2008120146 A1      10/2008
(Continued)

OTHER PUBLICATIONS

Communication pursuant to Article 94(3) EPC Received for European Application No. 18843254.6, mailed on Mar. 26, 2024, 08 pages.
(Continued)

*Primary Examiner* — Daniel C Washburn
*Assistant Examiner* — Penny L Caudle
(74) *Attorney, Agent, or Firm* — Foley IP Law, PLLC

(57) ABSTRACT

A computer-implemented method, computer program product, and computing system for synchronizing machine vision and audio is executed on a computing device and includes obtaining encounter information of a user encounter, wherein the encounter information includes machine vision encounter information and audio encounter information. The machine vision encounter information and the
(Continued)

audio encounter information are temporally-aligned to produce a temporarily-aligned encounter recording.

18 Claims, 47 Drawing Sheets

Related U.S. Application Data

(60) Provisional application No. 62/993,482, filed on Mar. 23, 2020, provisional application No. 62/638,809, filed on Mar. 5, 2018, provisional application No. 62/543,762, filed on Aug. 10, 2017.

(51) Int. Cl.
| | |
|---|---|
| *G10L 21/0208* | (2013.01) |
| *G10L 21/0272* | (2013.01) |
| *G16H 10/60* | (2018.01) |

(52) U.S. Cl.
CPC ......... *G10L 21/0272* (2013.01); *G16H 10/60* (2018.01); *G10L 2021/02082* (2013.01)

(58) Field of Classification Search
CPC ............. G10L 21/0208; G10L 21/0272; G10L 2021/02082; G10L 2021/02087
See application file for complete search history.

(56) References Cited

U.S. PATENT DOCUMENTS

| | | | |
|---|---|---|---|
| 8,132,104 B2 | 3/2012 | Ash | |
| 8,589,379 B2 | 11/2013 | Hirasawa | |
| 9,584,946 B1 | 2/2017 | Lyren et al. | |
| 9,730,023 B2 * | 8/2017 | Swirsky | H04W 76/10 |
| 2001/0044588 A1 | 11/2001 | Mault | |
| 2004/0122706 A1 | 6/2004 | Walker | |
| 2004/0122707 A1 | 6/2004 | Sabol | |
| 2005/0256746 A1 | 11/2005 | Zaleski | |
| 2006/0173708 A1 | 8/2006 | Vining | |
| 2006/0277071 A1 | 12/2006 | Shufeldt | |
| 2008/0243544 A1 | 10/2008 | Cafer | |
| 2009/0023555 A1 | 1/2009 | Raymond | |
| 2009/0089082 A1 | 4/2009 | Heckerman | |
| 2009/0089100 A1 | 4/2009 | Nenov et al. | |
| 2009/0304254 A1 | 12/2009 | Yoshida | |
| 2010/0063845 A1 | 3/2010 | Yeluri | |
| 2010/0094650 A1 | 4/2010 | Tran et al. | |
| 2011/0112832 A1 * | 5/2011 | Prorock | G11B 27/36 704/E15.044 |
| 2011/0254954 A1 | 10/2011 | Lee | |
| 2012/0101847 A1 | 4/2012 | Johnson et al. | |
| 2012/0197648 A1 | 8/2012 | Moloney | |
| 2012/0209625 A1 | 8/2012 | Armstrong | |
| 2012/0323589 A1 | 12/2012 | Udani | |
| 2013/0064358 A1 | 3/2013 | Nusbaum | |
| 2013/0138457 A1 | 5/2013 | Ragusa | |
| 2013/0173287 A1 | 7/2013 | Cashman et al. | |
| 2013/0238330 A1 | 9/2013 | Casella Dos Santos | |
| 2014/0013219 A1 | 1/2014 | Liu | |
| 2014/0074454 A1 * | 3/2014 | Brown | G10L 15/08 704/235 |
| 2014/0169767 A1 | 6/2014 | Goldberg | |
| 2014/0253876 A1 | 9/2014 | Klin | |
| 2014/0288968 A1 | 9/2014 | Johnson | |
| 2014/0337048 A1 | 11/2014 | Brown et al. | |
| 2015/0106123 A1 | 4/2015 | Amarasingham | |
| 2016/0239617 A1 | 8/2016 | Farooq et al. | |
| 2017/0039502 A1 | 2/2017 | Guman | |
| 2017/0098051 A1 | 4/2017 | Balram | |
| 2017/0116392 A1 | 4/2017 | Casella Dos Santos | |
| 2017/0186441 A1 * | 6/2017 | Wenus | H04N 7/147 |
| 2017/0277993 A1 | 9/2017 | Beaver | |
| 2018/0197548 A1 | 7/2018 | Palakodety et al. | |
| 2018/0332389 A1 | 11/2018 | Ekkizogloy | |

| | | | |
|---|---|---|---|
| 2022/0344038 A1 | 10/2022 | Gallopyn et al. | |
| 2023/0021529 A1 | 1/2023 | Bhattacherjee | |
| 2023/0290023 A1 | 9/2023 | Tsunomori | |

FOREIGN PATENT DOCUMENTS

| | | | |
|---|---|---|---|
| WO | 2016138522 A1 | 9/2016 | |
| WO | WO-2017108944 A1 * | 6/2017 | ......... G06Q 10/1093 |

OTHER PUBLICATIONS

Communication pursuant to Article 94(3) Received in European Patent Application No. 18844226.3, mailed on Mar. 22, 2024, 7 pages.

Sapru, et al., "Improving Speaker Diarization using Social Role Information", In Proceedings of International Conference on Acoustics, Speech and Signal Processing, May 4, 2014, pp. 101-105.

Klann et al., "An Intelligent Listening Framework for Capturing Encounter Notes from a Doctor-Patient Dialog", BMC Medical Informatics and Decision Making, vol. 9, Supplemental 1:S3, 2009, pp. 1-10.

Non-Final Office Action mailed on Dec. 11, 2023, in U.S. Appl. No. 17/697,593, 23 Pages.

Non-Final Office Action mailed on Nov. 9, 2023 in U.S. Appl. No. 17/678,791, 8 pages.

Non-Final Office Action mailed on Nov. 9, 2023 in U.S. Appl. No. 17/955,693, 8 pages.

Non-Final Office Action mailed on Oct. 23, 2023, in U.S. Appl. No. 17/210,233, 47 pages.

Notice of Allowance mailed on Feb. 14, 2024, in U.S. Appl. No. 17/571,799, 7 pages.

Notice of Allowance mailed on Jan. 31, 2024 in U.S. Appl. No. 17/846,355, 8 Pages.

Final Office Action mailed on Mar. 7, 2024, in U.S. Appl. No. 17/210,233, 54 pages.

Non-Final Office Action mailed on Sep. 27, 2023, in U.S. Appl. No. 17/846,355, 16 pages.

Notice of Allowance mailed on Mar. 18, 2024, in U.S. Appl. No. 17/571,799, 2 pages.

Communication 94(3) Received for European Application No. 18844406.1, mailed on Apr. 4, 2024, 11 pages.

Communication 94(3) Received for European Application No. 18844669.4, mailed on Apr. 3, 2024, 5 pages.

Communication 94(3) Received for European Application No. 18844829.4, mailed on Apr. 4, 2024, 5 pages.

Communication pursuant to Article 94(3) EPC Received for European Application No. 18843255.3, mailed on Feb. 26, 2024, 6 pages.

Communication pursuant to Article 94(3) EPC Received for European Application No. 18844752.8, mailed on Feb. 7, 2024, 06 pages.

Communication pursuant to Article 94(3) EPC, Received for European Application No. 18843175.3, mailed on Feb. 29, 2024, 09 pages.

Communication pursuant to Article 94(3) EPC, Received for European Application No. 18843648.9, mailed on May 2, 2024, 10 pages.

Communication pursuant to Article 94(3) EPC, Received for European Application No. 18843945.9. mailed on Mar. 4, 2024, 09 pages.

Communication Pursuant to Article 94(3) EPC, Received for European Application No. 18844407.9, mailed on Feb. 14, 2024, 06 pages.

Communication pursuant to Article 94(3) received in European Application No. 18843873.3, mailed on Apr. 11, 2024, 5 pages.

Communication pursuant to Article 94(3) received in European Application No. 18844530.8, mailed on Apr. 3, 2024, 5 pages.

Communication pursuant to Article 94(3) Received in European Patent Application No. 18845144.7, mailed on May 3, 2024, 10 pages.

(56) References Cited

OTHER PUBLICATIONS

Communication pursuant to Rules 70(2) and 70a(2) Received for European Application No. 19763338.1, mailed on Apr. 25, 2022, 01 pages.
Communication pursuant to Rules 70(2) and 70a(2) Received for European Application No. 19763834.9, mailed on Jan. 5, 2022, 01 pages.
Communication pursuant to Rules 70(2) and 70a(2) Received for European Application No. 19764329.9, mailed on Jan. 12, 2022, 01 pages.
Communication under Rule 71(3) EPC Received for European Application No. 18843874.1, mailed on May 10, 2024, 09 pages.
Communication under Rule 71(3) EPC Received for European Application No. 18845046.4, mailed on Feb. 29, 2024, 5 pages.
Final Office Action mailed on Jun. 21, 2024, in U.S. Appl. No. 17/697,593, 28 pages.
Lee, et al., "Portable meeting recorder.", Proceedings of the tenth ACM international conference on Multimedia, 2002, 10 Pages.
Non-Final Office Action mailed on Apr. 16, 2024, in U.S. Appl. No. 17/210,300, 13 pages.
Notice of Allowance mailed on Apr. 3, 2024, in U.S. Appl. No. 17/678,791, 8 pages.
Notice of Allowance mailed on Apr. 17, 2024, in U.S. Appl. No. 17/955,693, 08 pages.

Weibel, et al., "Lab-in-a-Box. semi-automatic tracking of activity in the medical office," Personal Ubiquitous Computing, Springer, Sep. 28, 2014, pp. 317-334.
Final Office Action mailed on Aug. 21, 2024, in U.S. Appl. No. 17/210,300, 08 pages.
Notice of Allowance received in matter (U.S. Appl. No. 17/571,799) mailed on Jul. 31, 2024.
Communication 94(3) Received for European Application No. 18845046.4, mailed on Jul. 26, 2024.
Communication under Rule 71(3) Received in European Patent Application No. 18842996.3, mailed on Sep. 25, 2024, 08 pages.
Decision to Grant pursuant to Article 97(1) received in European Application No. 18842996.3, mailed on Jan. 30, 2025, 2 pages.
Non-Final Office Action mailed on Jan. 27, 2025, in U.S. Appl. No. 17/210,253, 40 pages.
Non-Final Office Action mailed on Oct. 7, 2024, in U.S. Appl. No. 17/210,262, 13 pages.
Communication pursuant to Article 94(3) Received in European Patent Application No. 18843329.6, mailed on Mar. 26, 2025, 04 pages.
Communication under Rule 71(3) EPC Received for European Application No. 18845046.4, mailed on Aug. 18, 2025, 8 pages.
Communication pursuant to Article 94(3) received in European Application No. 19763474.4, mailed on Jul. 16, 2025, 09 pages.

* cited by examiner

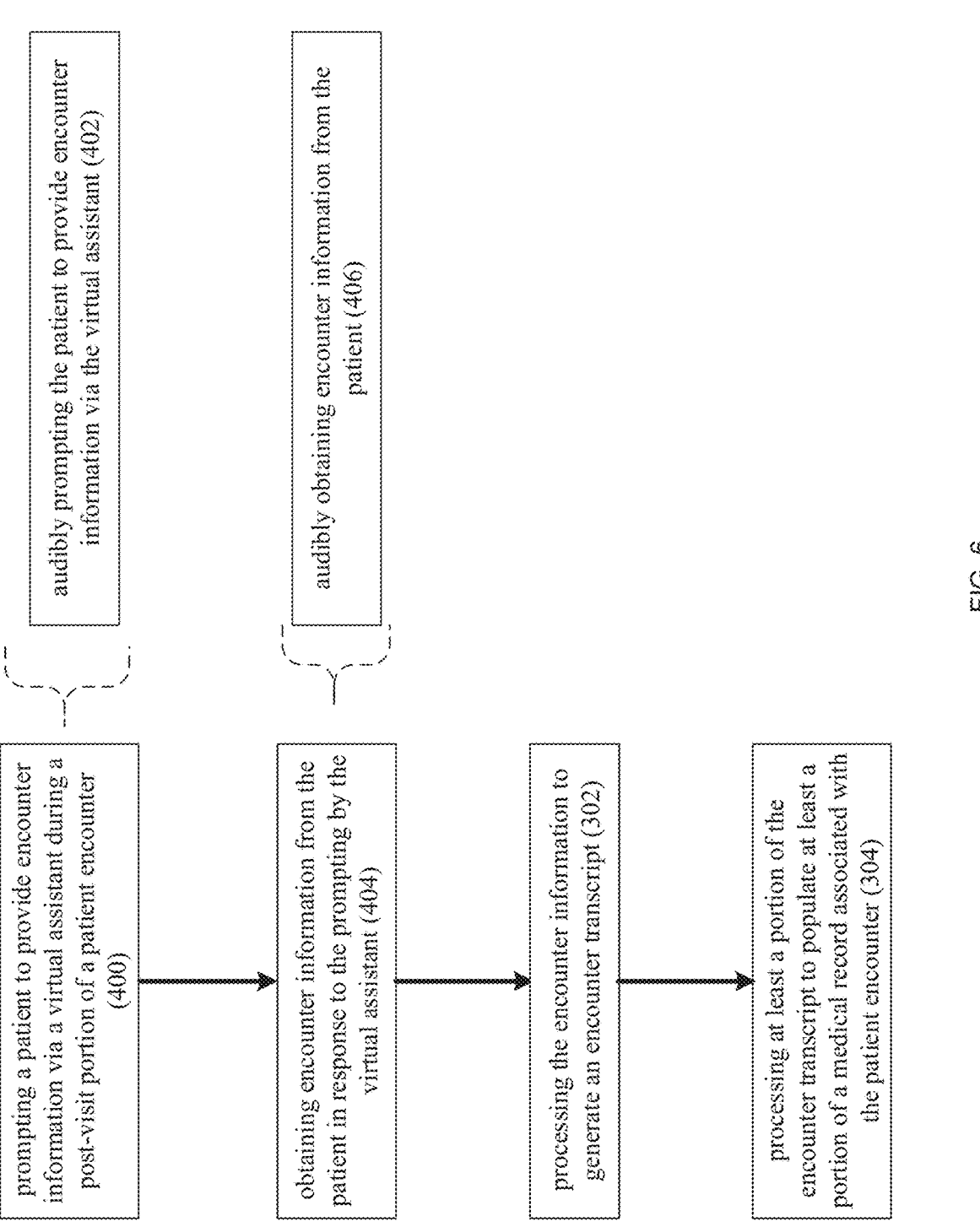

FIG. 6 prompting a patient to provide encounter information via a virtual assistant during a post-visit portion of a patient encounter (400)

audibly prompting the patient to provide encounter information via the virtual assistant (402)

obtaining encounter information from the patient in response to the prompting by the virtual assistant (404)

audibly obtaining encounter information from the patient (406)

processing the encounter information to generate an encounter transcript (302)

processing at least a portion of the encounter transcript to populate at least a portion of a medical record associated with the patient encounter (304)

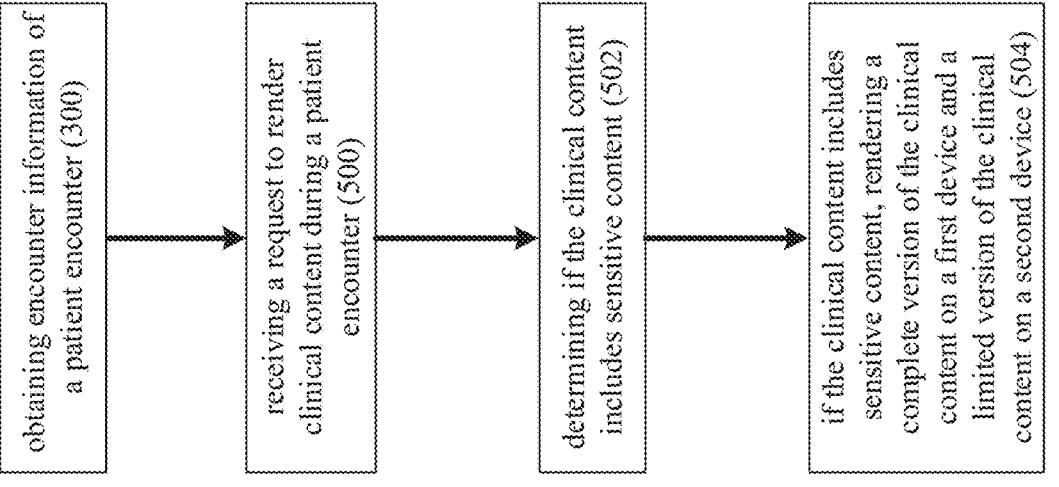

obtaining encounter information of a patient encounter (300)

receiving a request to render clinical content during a patient encounter (500)

determining if the clinical content includes sensitive content (502)

if the clinical content includes sensitive content, rendering a complete version of the clinical content on a first device and a limited version of the clinical content on a second device (504)

FIG. 8

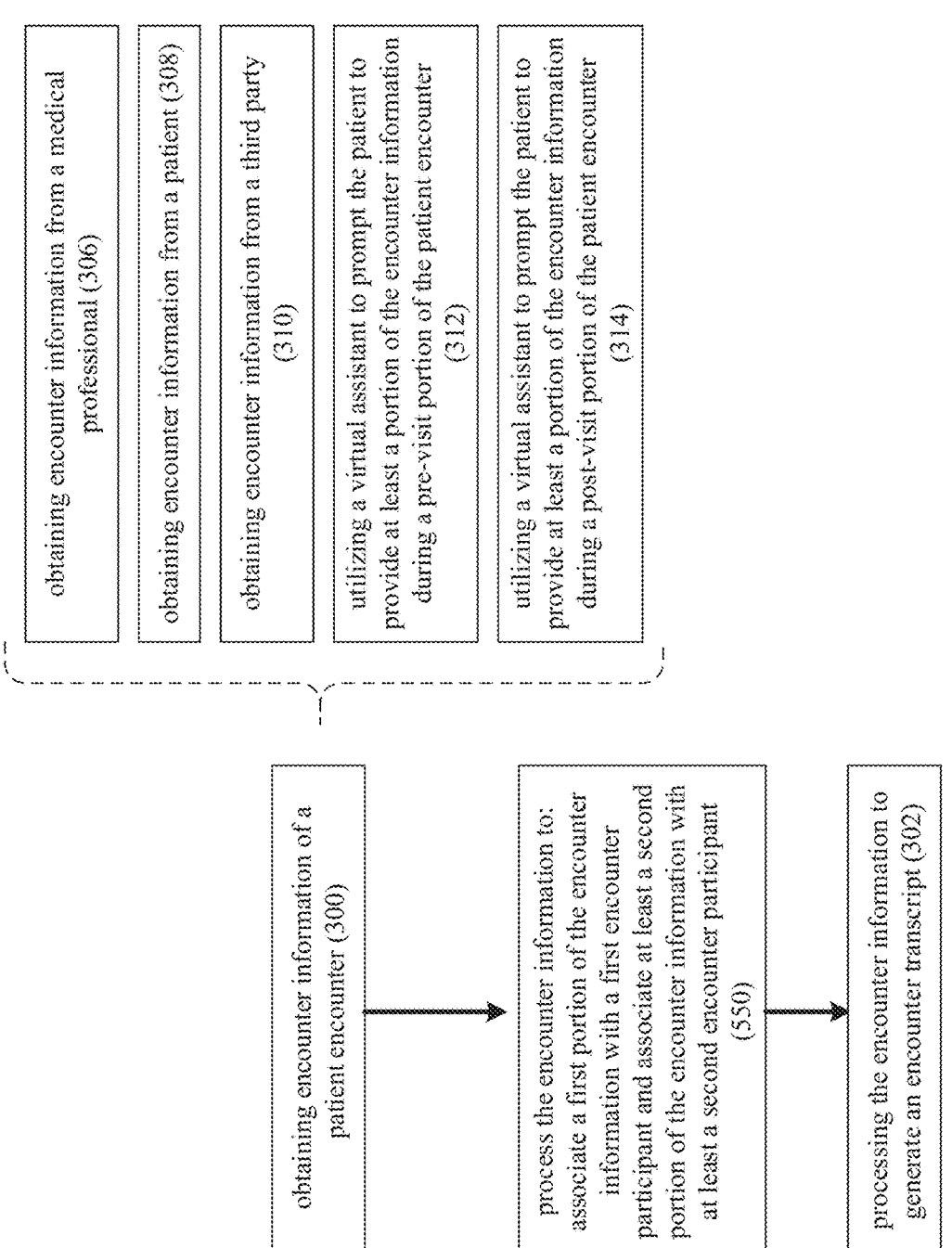

obtaining encounter information from a medical professional (306)

obtaining encounter information from a patient (308)

obtaining encounter information from a third party (310)

utilizing a virtual assistant to prompt the patient to provide at least a portion of the encounter information during a pre-visit portion of the patient encounter (312)

utilizing a virtual assistant to prompt the patient to provide at least a portion of the encounter information during a post-visit portion of the patient encounter (314)

obtaining encounter information of a patient encounter (300)

process the encounter information to: associate a first portion of the encounter information with a first encounter participant and associate at least a second portion of the encounter information with at least a second encounter participant (550)

processing the encounter information to generate an encounter transcript (302)

FIG. 9

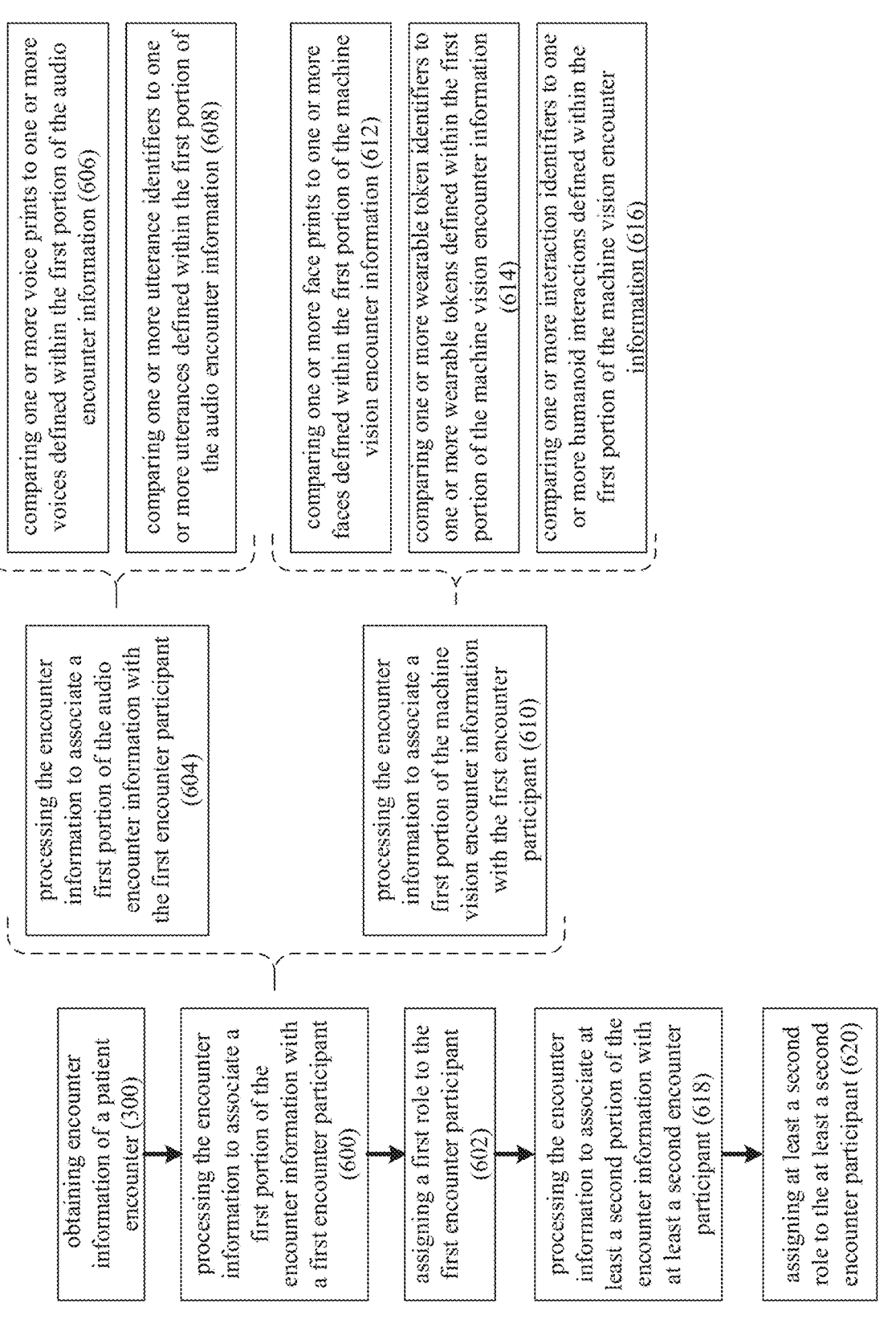

comparing one or more voice prints to one or more voices defined within the first portion of the audio encounter information (606)

comparing one or more utterance identifiers to one or more utterances defined within the first portion of the audio encounter information (608)

comparing one or more face prints to one or more faces defined within the first portion of the machine vision encounter information (612)

comparing one or more wearable token identifiers to one or more wearable tokens defined within the first portion of the machine vision encounter information (614)

comparing one or more interaction identifiers to one or more humanoid interactions defined within the first portion of the machine vision encounter information (616)

processing the encounter information to associate a first portion of the audio encounter information with the first encounter participant (604)

processing the encounter information to associate a first portion of the machine vision encounter information with the first encounter participant (610)

obtaining encounter information of a patient encounter (300)

processing the encounter information to associate a first portion of the encounter information with a first encounter participant (600)

assigning a first role to the first encounter participant (602)

processing the encounter information to associate at least a second portion of the encounter information with at least a second encounter participant (618)

assigning at least a second role to the at least a second encounter participant (620)

FIG. 10

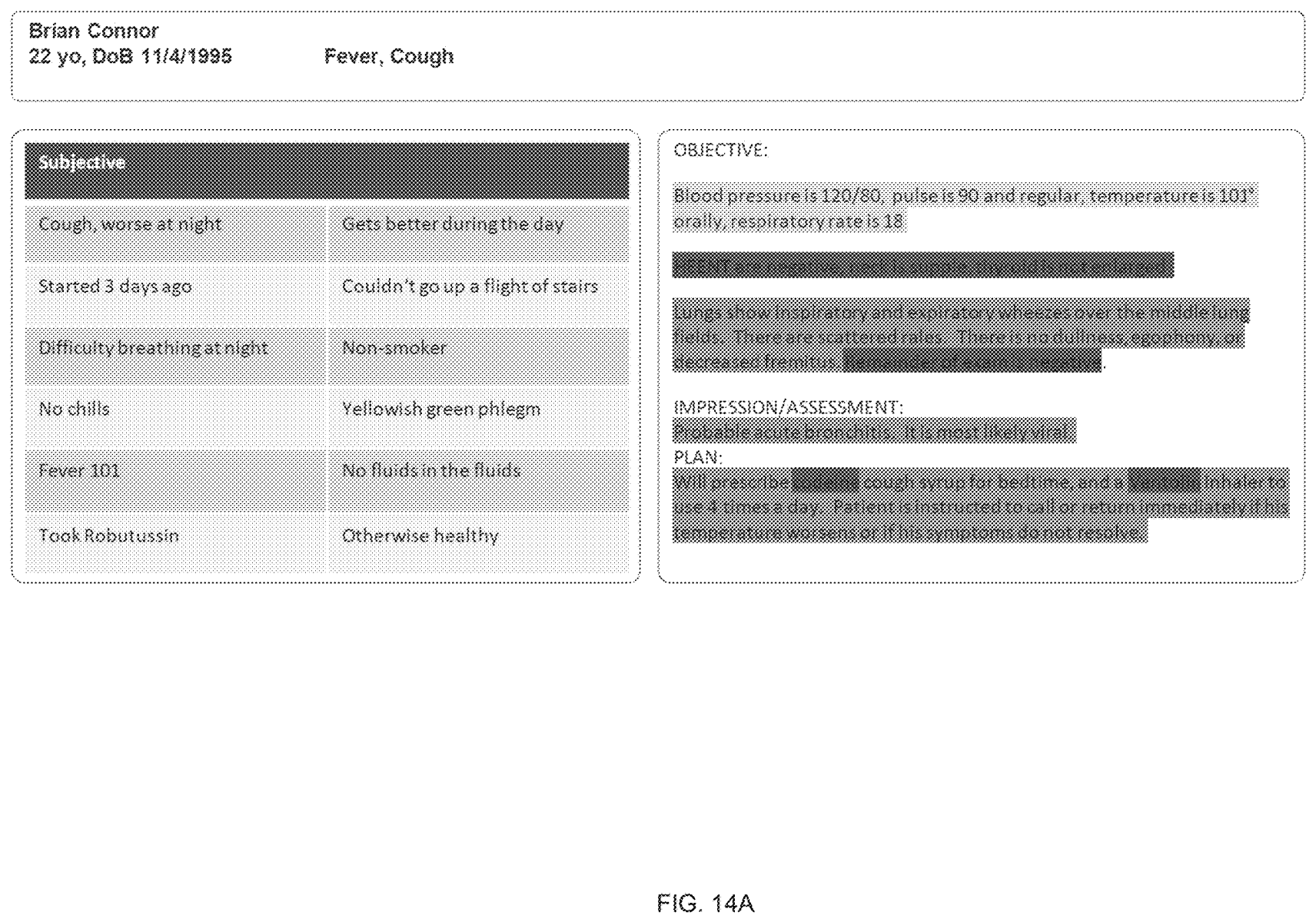

Brian Connor
22 yo, DoB 11/4/1995          Fever, Cough

Subjective

Cough, worse at night          Gets better during the day

Started 3 days ago             Couldn't go up a flight of stairs

Difficulty breathing at night  Non-smoker

No chills                      Yellowish green phlegm

Fever 101                      No fluids in the fluids

Took Robutussin                Otherwise healthy

OBJECTIVE:

Blood pressure is 120/80, pulse is 90 and regular, temperature is 101 orally, respiratory rate is 18

IMPRESSION/ASSESSMENT:

PLAN:

FIG. 14A

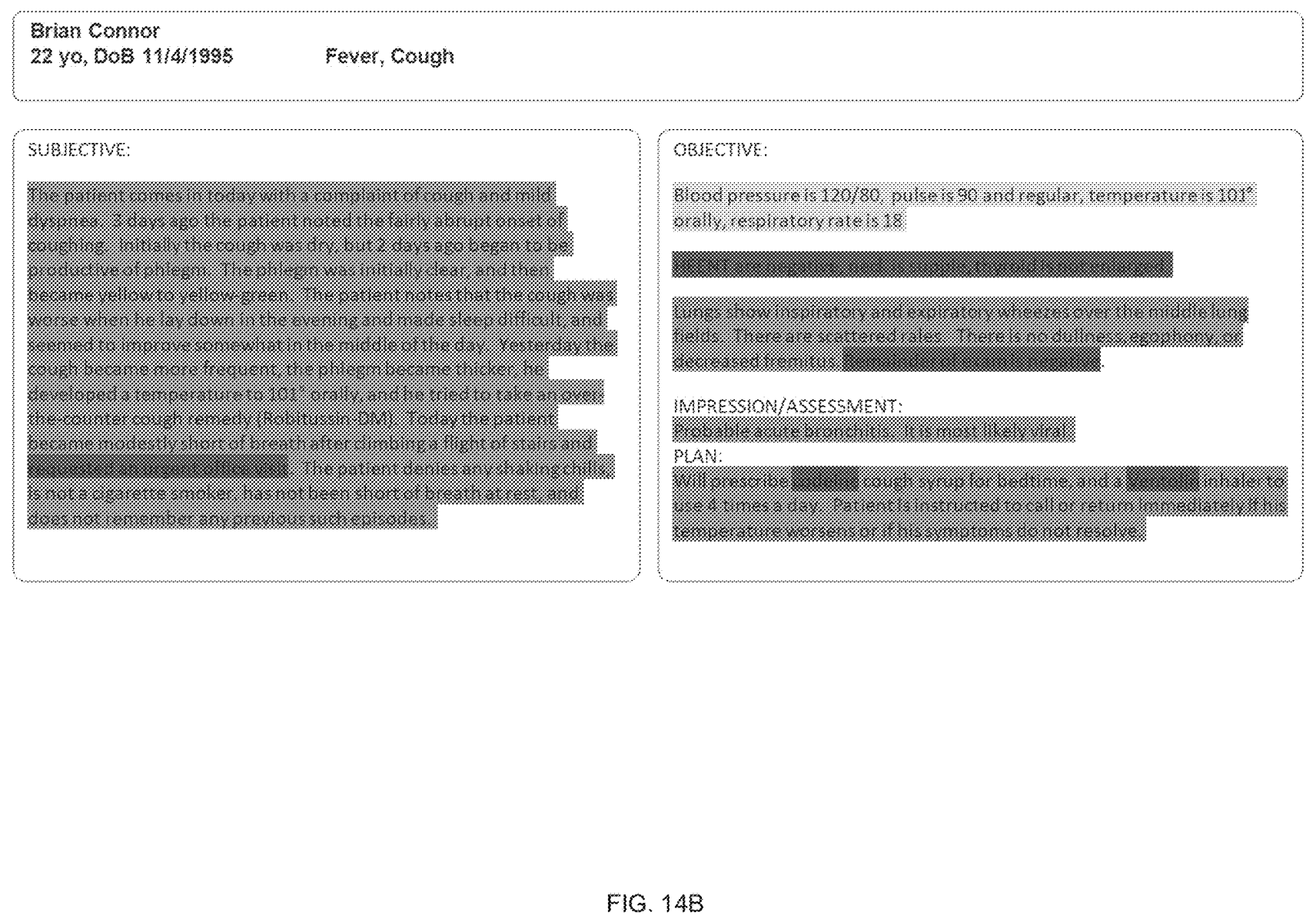

Brian Connor
22 yo, DoB 11/4/1995

Fever, Cough

SUBJECTIVE:

OBJECTIVE:

Blood pressure is 120/80, pulse is 90 and regular, temperature is 101
orally, respiratory rate is 18

IMPRESSION/ASSESSMENT:

PLAN:

FIG. 14B

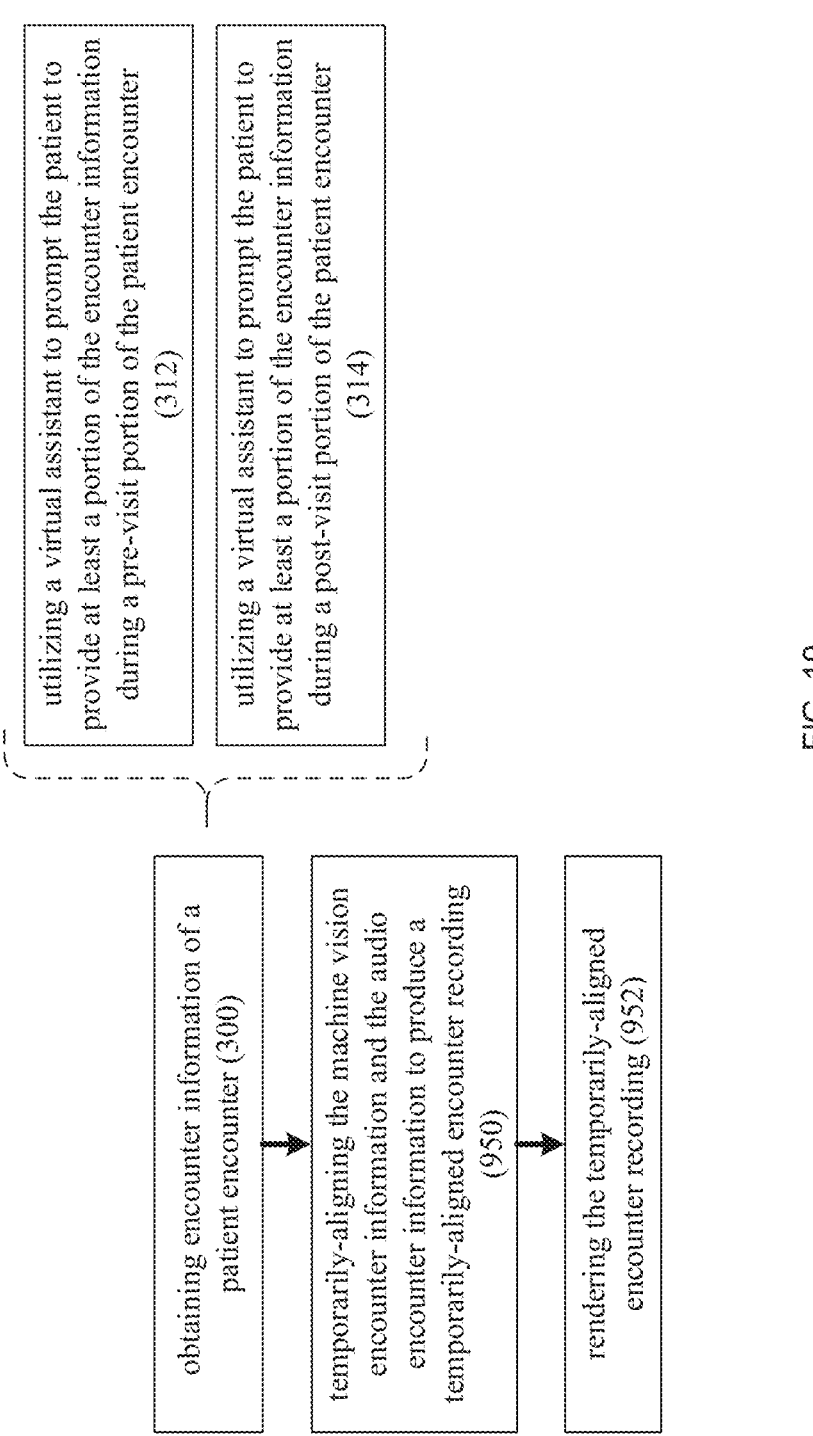

utilizing a virtual assistant to prompt the patient to provide at least a portion of the encounter information during a pre-visit portion of the patient encounter (312)

utilizing a virtual assistant to prompt the patient to provide at least a portion of the encounter information during a post-visit portion of the patient encounter (314)

obtaining encounter information of a patient encounter (300)

temporarily-aligning the machine vision encounter information and the audio encounter information to produce a temporarily-aligned encounter recording (950)

rendering the temporarily-aligned encounter recording (952)

FIG. 19 obtaining encounter information of a patient encounter (300)

Figure 21:
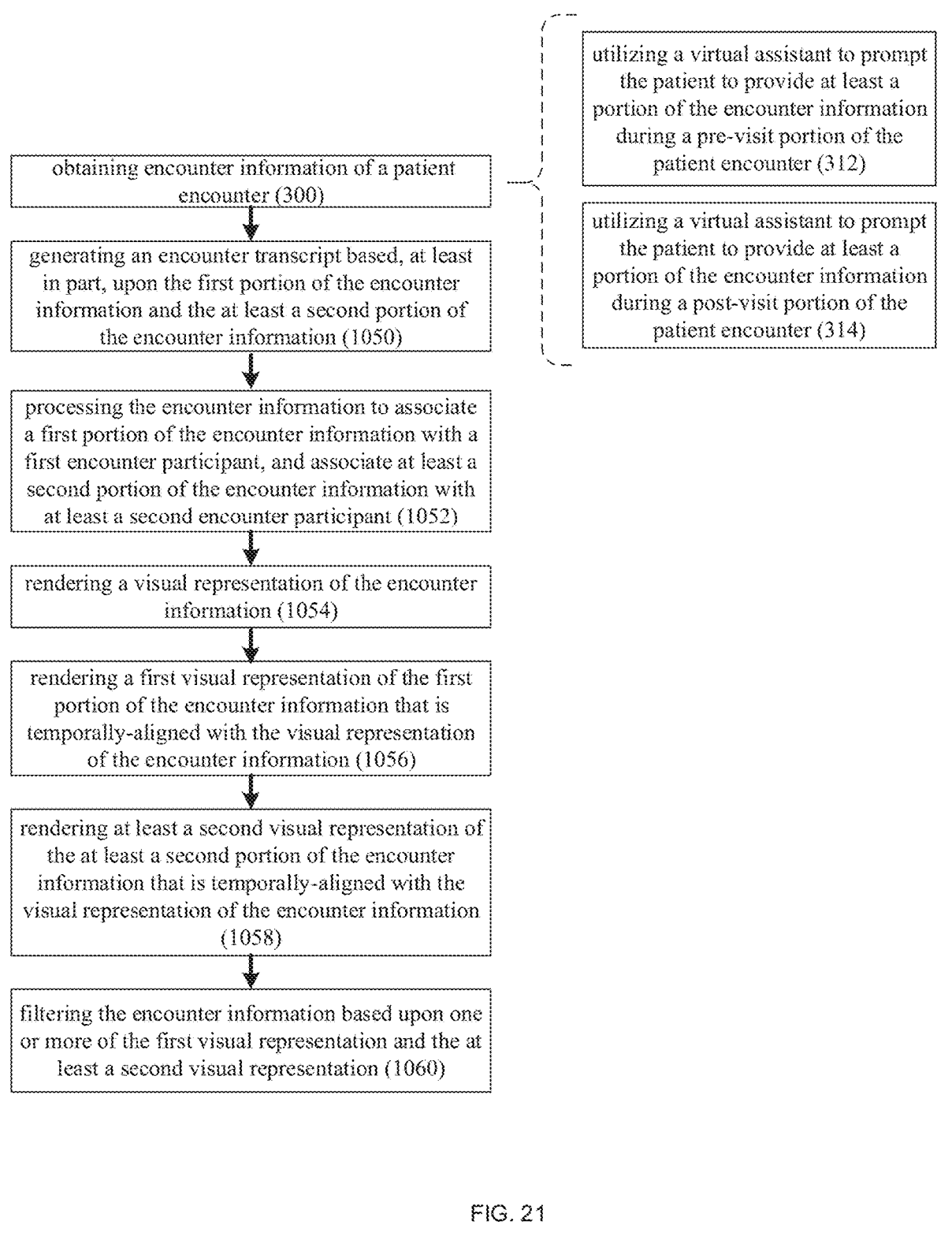

utilizing a virtual assistant to prompt the patient to provide at least a portion of the encounter information during a pre-visit portion of the patient encounter (312)

utilizing a virtual assistant to prompt the patient to provide at least a portion of the encounter information during a post-visit portion of the patient encounter (314)

generating an encounter transcript based, at least in part, upon the first portion of the encounter information and the at least a second portion of the encounter information (1050)

processing the encounter information to associate a first portion of the encounter information with a first encounter participant, and associate at least a second portion of the encounter information with at least a second encounter participant (1052)

rendering a visual representation of the encounter information (1054)

rendering a first visual representation of the first portion of the encounter information that is temporally-aligned with the visual representation of the encounter information (1056)

rendering at least a second visual representation of the at least a second portion of the encounter information that is temporally-aligned with the visual representation of the encounter information (1058)

filtering the encounter information based upon one or more of the first visual representation and the at least a second visual representation (1060)

Figure 22:
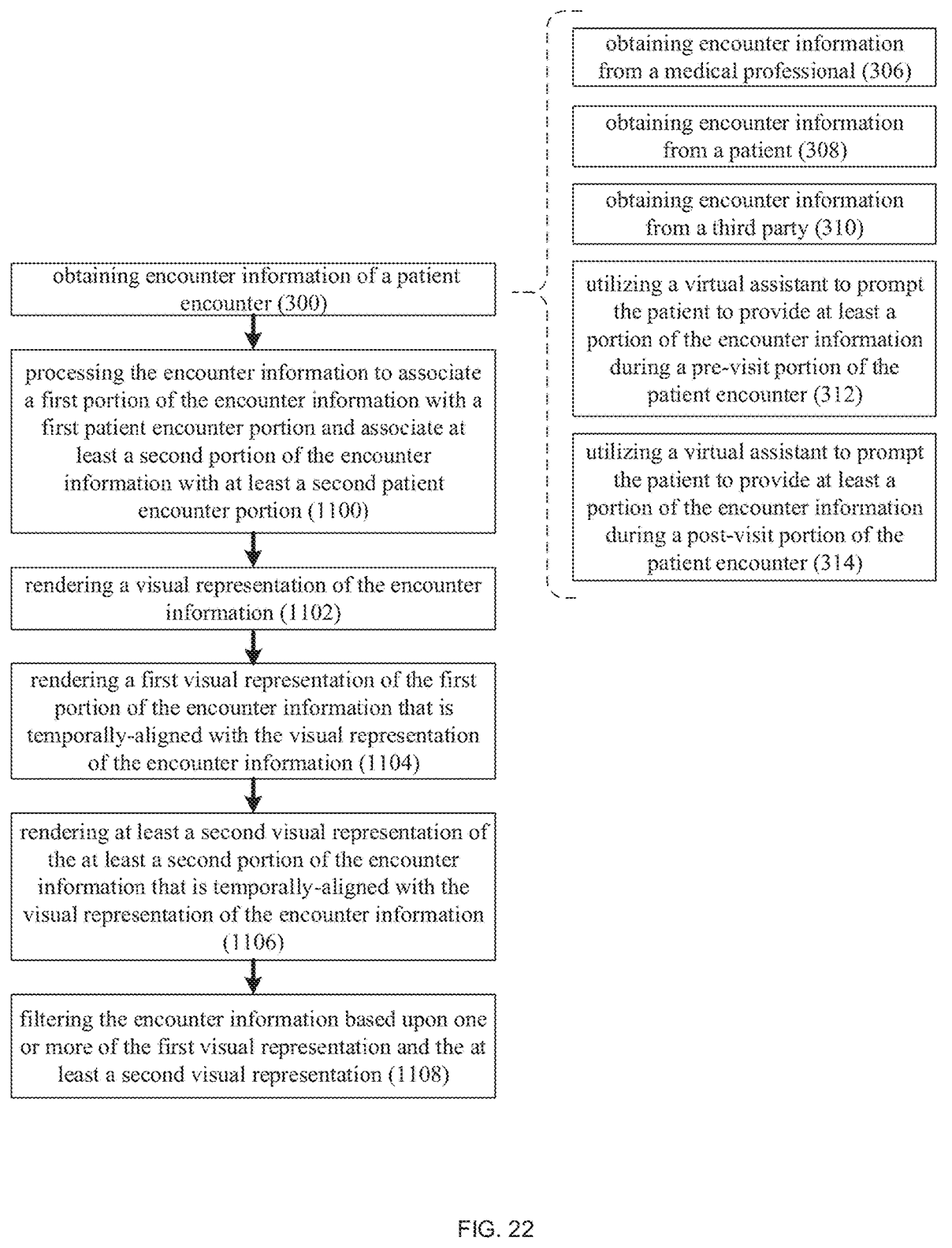

FIG. 21 obtaining encounter information
from a medical professional (306)

obtaining encounter information
from a patient (308)

obtaining encounter information
from a third party (310)

obtaining encounter information of a patient
encounter (300)

utilizing a virtual assistant to prompt
the patient to provide at least a
portion of the encounter information
during a pre-visit portion of the
patient encounter (312)

processing the encounter information to associate
a first portion of the encounter information with a
first patient encounter portion and associate at
least a second portion of the encounter
information with at least a second patient
encounter portion (1100)

utilizing a virtual assistant to prompt
the patient to provide at least a
portion of the encounter information
during a post-visit portion of the
patient encounter (314)

rendering a visual representation of the encounter
information (1102)

rendering a first visual representation of the first
portion of the encounter information that is
temporally-aligned with the visual representation
of the encounter information (1104)

rendering at least a second visual representation of
the at least a second portion of the encounter
information that is temporally-aligned with the
visual representation of the encounter information
(1106)

filtering the encounter information based upon one
or more of the first visual representation and the at
least a second visual representation (1108)

FIG. 22 obtaining encounter information of a user encounter (1300)

processing the encounter information to generate an encounter transcript (1302)

processing at least a portion of the encounter transcript to populate at least a portion of a record associated with the user encounter (1304)

receiving a request to render content during a user encounter (1500)

determining if the content includes sensitive content (1502)

if the content includes sensitive content, rendering a complete version of the content on a first device and a limited version of the content on a second device (1504)

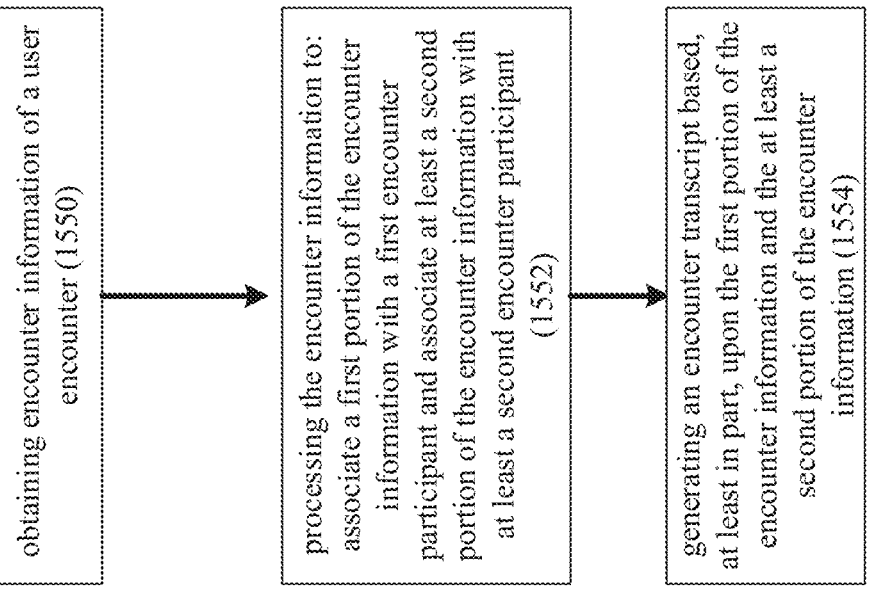

obtaining encounter information of a user encounter (1550)

processing the encounter information to: associate a first portion of the encounter information with a first encounter participant and associate at least a second portion of the encounter information with at least a second encounter participant (1552)

generating an encounter transcript based, at least in part, upon the first portion of the encounter information and the at least a second portion of the encounter information (1554)

FIG. 30

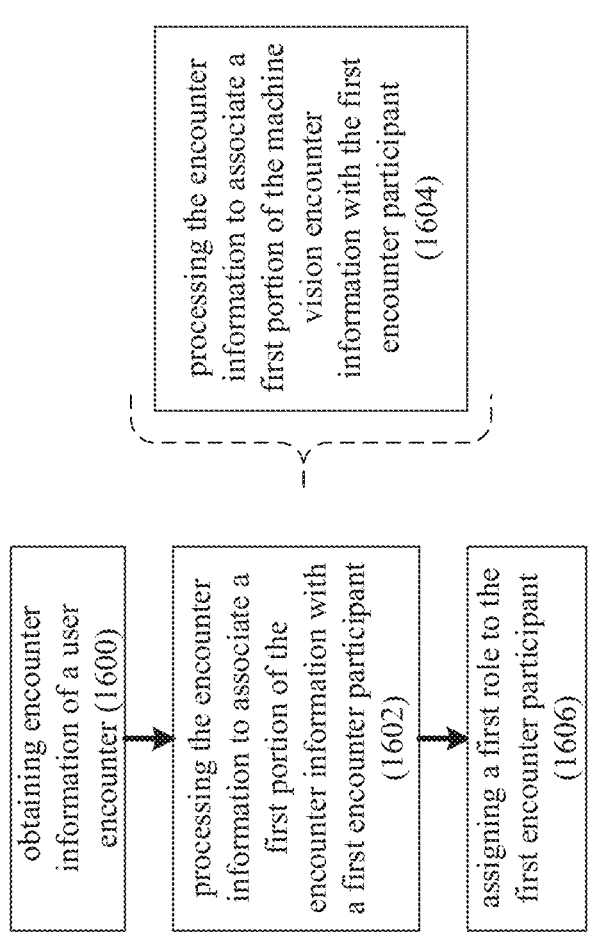

processing the encounter information to associate a first portion of the machine vision encounter information with the first encounter participant (1604)

obtaining encounter information of a user encounter (1600)

processing the encounter information to associate a first portion of the encounter information with a first encounter participant (1602)

assigning a first role to the first encounter participant (1606)

FIG. 31 obtaining encounter information of a user encounter (1700)

processing the encounter information to generate an encounter transcript (1702)

generating at least one semantic frame based, at least in part, upon at least one portion of the encounter transcript (1704)

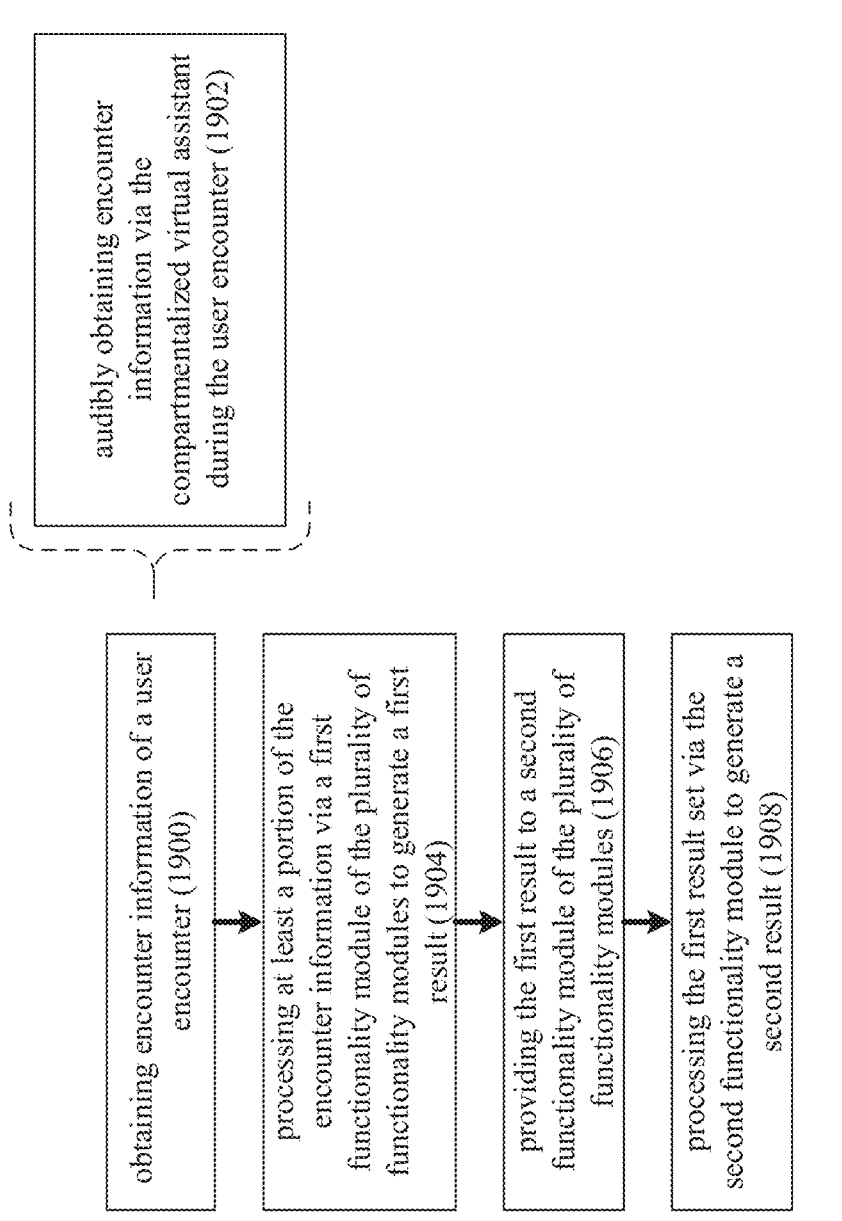

audibly obtaining encounter information via the compartmentalized virtual assistant during the user encounter (1902)

obtaining encounter information of a user encounter (1900)

processing at least a portion of the encounter information via a first functionality module of the plurality of functionality modules to generate a first result (1904)

providing the first result to a second functionality module of the plurality of functionality modules (1906)

processing the first result set via the second functionality module to generate a second result (1908)

FIG. 37 obtaining encounter information of a user encounter (1950)

temporarily-aligning the machine vision encounter information and the audio encounter information to produce a temporarily-aligned encounter recording (1952)

Figure 39:
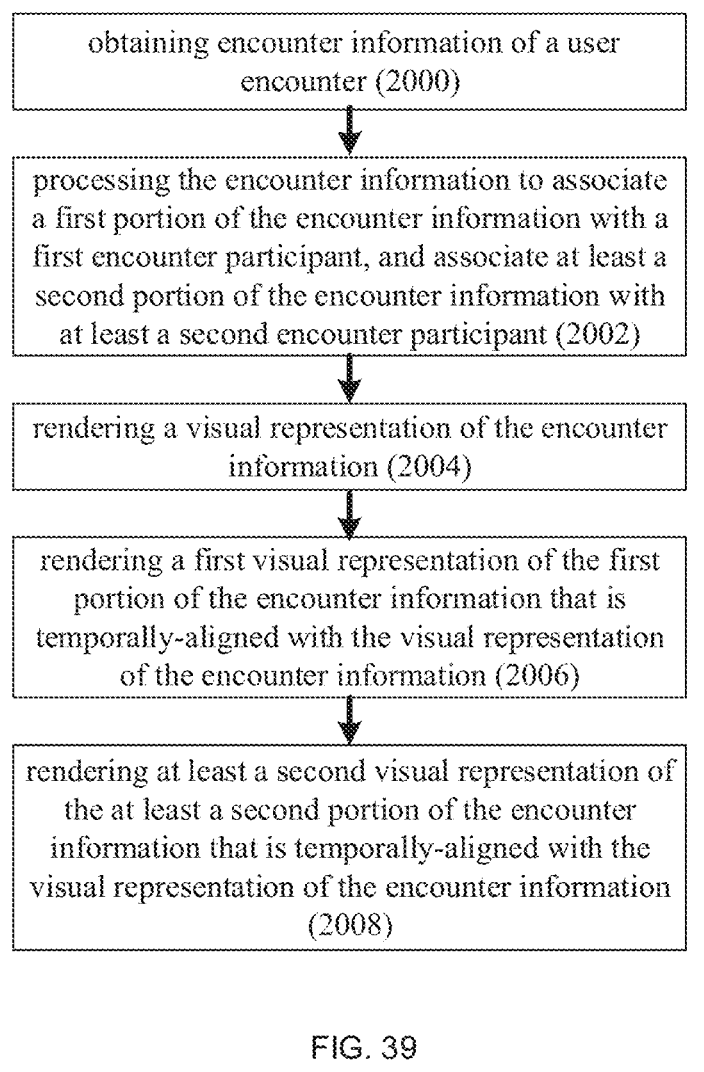

obtaining encounter information of a user encounter (2000)

↓ processing the encounter information to associate a first portion of the encounter information with a first encounter participant, and associate at least a second portion of the encounter information with at least a second encounter participant (2002)

↓ rendering a visual representation of the encounter information (2004)

↓ rendering a first visual representation of the first portion of the encounter information that is temporally-aligned with the visual representation of the encounter information (2006)

↓ rendering at least a second visual representation of the at least a second portion of the encounter information that is temporally-aligned with the visual representation of the encounter information (2008)

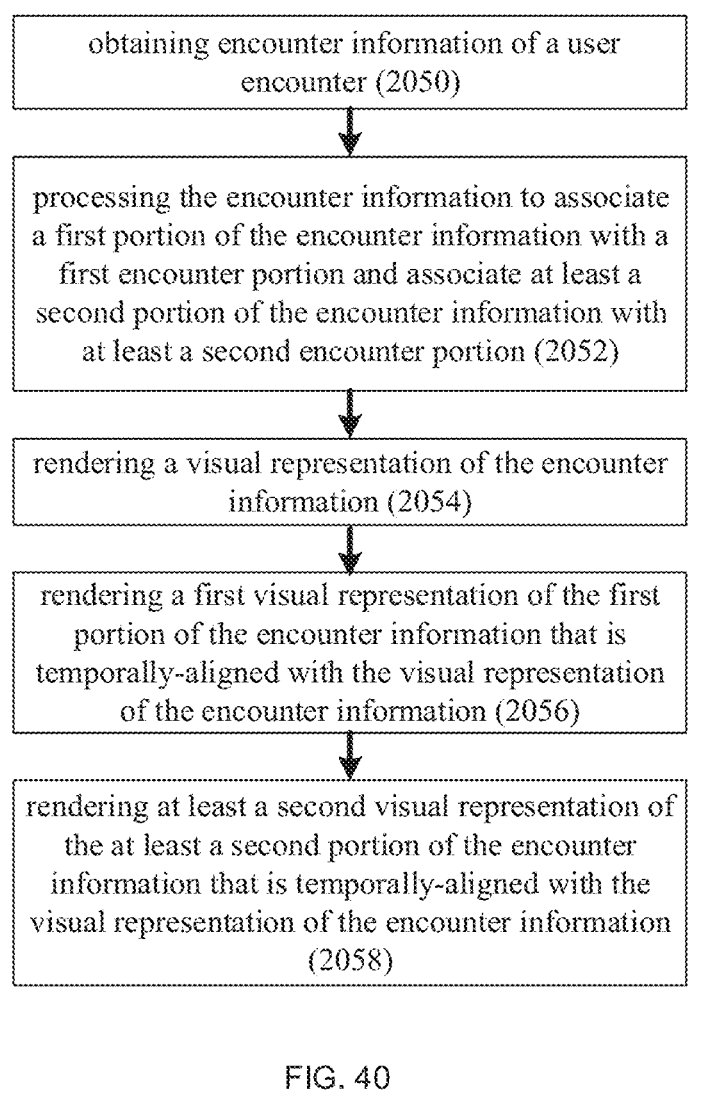

FIG. 39 obtaining encounter information of a user
encounter (2050)

↓ processing the encounter information to associate
a first portion of the encounter information with a
first encounter portion and associate at least a
second portion of the encounter information with
at least a second encounter portion (2052)

↓ rendering a visual representation of the encounter
information (2054)

↓ rendering a first visual representation of the first
portion of the encounter information that is
temporally-aligned with the visual representation
of the encounter information (2056)

↓ rendering at least a second visual representation of
the at least a second portion of the encounter
information that is temporally-aligned with the
visual representation of the encounter information
(2058)

FIG. 40

AUTOMATED CLINICAL DOCUMENTATION SYSTEM AND METHOD FOR SYNCHRONIZING MACHINE VISION AND AUDIO ENCOUNTER INFORMATION

PRIORITY APPLICATION(S)

This application claims the benefit of U.S. Provisional Application Ser. No. 62/993,482, filed on 23 Mar. 2020. This application is also a Continuation-in-Part of U.S. application Ser. No. 16/058,826, filed on 8 Aug. 2018, which claims the benefit of U.S. Provisional Application Ser. No. 62/543,762, filed on 10 Aug. 2017 and U.S. Provisional Application Ser. No. 62/638,809, filed on 5 Mar. 2018, their entire contents of which are incorporated herein by reference.

TECHNICAL FIELD

This disclosure relates to documentation systems and methods and, more particularly, to automated clinical documentation systems and methods.

BACKGROUND

As is known in the art, clinical documentation is the creation of records and documentation that details an encounter. As would be expected, traditional clinical documentation includes various types of data, examples of which may include but are not limited to paper-based documents and transcripts, as well as various images and diagrams.

As the world moved from paper-based content to digital content, clinical documentation also moved in that direction, where records and documentation were gradually transitioned from stacks of paper geographically-dispersed across multiple locations/institutions to consolidated and readily accessible digital content.

SUMMARY OF DISCLOSURE

Concept 13-16

A computer-implemented method for source separation is executed on a computing device and includes: obtaining encounter information of a user encounter, wherein the encounter information includes first audio encounter information obtained from a first encounter participant and at least second audio encounter information obtained from at least a second encounter participant; and processing the first audio encounter information and the at least second audio encounter information to eliminate audio interference between the first audio encounter information and the at least second audio encounter information.

One or more of the following features may be included. The user encounter may include one or more of: a financial encounter; a life coach encounter; a legal encounter; a telecom encounter; a retail encounter; and a business encounter. The encounter information may include one or more of: financial information; life coach information; legal information; telecom information; retail information; and business information. The computer-implemented method may be executed within one or more of: a financial environment; a life coach environment; a legal environment; a telecom environment; a retail environment; and a business environment. Obtaining encounter information of a user encounter may include: steering a first audio recording beam toward the first encounter participant; and steering at least a second audio recording beam toward the at least a second encounter participant. Processing the first audio encounter information and the at least a second audio encounter information to eliminate audio interference may include: executing an echo cancellation process on the first audio encounter information and the at least a second audio encounter information. Processing the first audio encounter information and the at least a second audio encounter information to eliminate audio interference includes: executing a blind source process on the first audio encounter information and the at least a second audio encounter information.

The details of one or more implementations are set forth in the accompanying drawings and the description below. Other features and advantages will become apparent from the description, the drawings, and the claims.

A computer-implemented method for compartmentalizing a virtual assistant is executed on a computing device and includes: obtaining encounter information via a compartmentalized virtual assistant during a user encounter, wherein the compartmentalized virtual assistant includes a core functionality module; and adding one or more additional functionalities to the compartmentalized virtual assistant on an as-needed basis.

One or more of the following features may be included. The user encounter may include one or more of: a financial encounter; a life coach encounter; a legal encounter; a telecom encounter; a retail encounter; and a business encounter. The encounter information may include one or more of: financial information; life coach information; legal information; telecom information; retail information; and business information. The computer-implemented method may be executed within one or more of: a financial environment; a life coach environment; a legal environment; a telecom environment; a retail environment; and a business environment. Adding one or more additional functionalities to the compartmentalized virtual assistant on an as-needed basis may include: loading one or more additional functionality modules for the compartmentalized virtual assistant when needed to effectuate the additional functionalities. One or more existing functionalities may be removed from the compartmentalized virtual assistant on an as-needed basis. Removing one or more existing functionalities from the compartmentalized virtual assistant on an as-needed basis may include: unloading one or more existing functionality modules of the compartmentalized virtual assistant when no longer needed to effectuate the existing functionalities.

The details of one or more implementations are set forth in the accompanying drawings and the description below. Other features and advantages will become apparent from the description, the drawings, and the claims.

A computer-implemented method for functionality module communication is executed on a computing device and includes: obtaining encounter information via a compartmentalized virtual assistant during a user encounter, wherein the compartmentalized virtual assistant includes a plurality of functionality modules; processing at least a portion of the encounter information via a first functionality module of the plurality of functionality modules to generate a first result; providing the first result to a second functionality module of the plurality of functionality modules; and processing the first result set via the second functionality module to generate a second result.

One or more of the following features may be included. The user encounter may include one or more of: a financial encounter; a life coach encounter; a legal encounter; a telecom encounter; a retail encounter; and a business encounter. The encounter information may include one or more of: financial information; life coach information; legal information; telecom information; retail information; and business information. The computer-implemented method may be executed within one or more of: a financial environment; a life coach environment; a legal environment; a telecom environment; a retail environment; and a business environment. The encounter information may include one or more of: machine vision encounter information obtained via one or more machine vision systems; and audio encounter information obtained via one or more audio sensors. The one or more machine vision systems may include one or more of: an RGB imaging system; an infrared imaging system; an ultraviolet imaging system; a laser imaging system; an X-ray imaging system; a SONAR imaging system; a RADAR imaging system; and a thermal imaging system. Obtaining encounter information via a compartmentalized virtual assistant during a user encounter may include: audibly obtaining encounter information via the compartmentalized virtual assistant during the user encounter.

The details of one or more implementations are set forth in the accompanying drawings and the description below. Other features and advantages will become apparent from the description, the drawings, and the claims.

A computer-implemented method for synchronizing machine vision and audio is executed on a computing device and includes: obtaining encounter information of a user encounter, wherein the encounter information includes machine vision encounter information and audio encounter information; and temporally-aligning the machine vision encounter information and the audio encounter information to produce a temporarily-aligned encounter recording.

One or more of the following features may be included. The user encounter may include one or more of: a financial encounter; a life coach encounter; a legal encounter; a telecom encounter; a retail encounter; and a business encounter. The encounter information may include one or more of: financial information; life coach information; legal information; telecom information; retail information; and business information. The computer-implemented method may be executed within one or more of: a financial environment; a life coach environment; a legal environment; a telecom environment; a retail environment; and a business environment. The machine vision encounter information may be obtained via one or more machine vision systems. The one or more machine vision systems may include one or more of: an RGB imaging system; an infrared imaging system; an ultraviolet imaging system; a laser imaging system; an X-ray imaging system; a SONAR imaging system; a RADAR imaging system; and a thermal imaging system. The audio encounter information may be obtained via one or more audio sensors.

The details of one or more implementations are set forth in the accompanying drawings and the description below. Other features and advantages will become apparent from the description, the drawings, and the claims.

BRIEF DESCRIPTION OF THE DRAWINGS

FIG. 6 is a flow chart of another implementation of the automated clinical documentation process of FIG. 1;

FIG. 8 is a flow chart of another implementation of the automated clinical documentation process of FIG. 1;

FIG. 9 is a flow chart of another implementation of the automated clinical documentation process of FIG. 1;

FIG. 10 is a flow chart of another implementation of the automated clinical documentation process of FIG. 1;

FIGS. 14A-14B are diagrammatic views of a medical record as populated by the automated clinical documentation process of FIG. 1;

FIG. 19 is a flow chart of another implementation of the automated clinical documentation process of FIG. 1;

FIG. 21 is a flow chart of another implementation of the automated clinical documentation process of FIG. 1;

FIG. 22 is a flow chart of another implementation of the automated clinical documentation process of FIG. 1;

FIG. 30 is a flow chart of another implementation of the automated clinical documentation process of FIG. 1;

FIG. 31 is a flow chart of another implementation of the automated clinical documentation process of FIG. 1;

FIG. 37 is a flow chart of another implementation of the automated clinical documentation process of FIG. 1;

FIG. 39 is a flow chart of another implementation of the automated clinical documentation process of FIG. 1;

FIG. 40 is a flow chart of another implementation of the automated clinical documentation process of FIG. 1;

Like reference symbols in the various drawings indicate like elements.

DETAILED DESCRIPTION OF THE PREFERRED EMBODIMENTS

Figure 1:
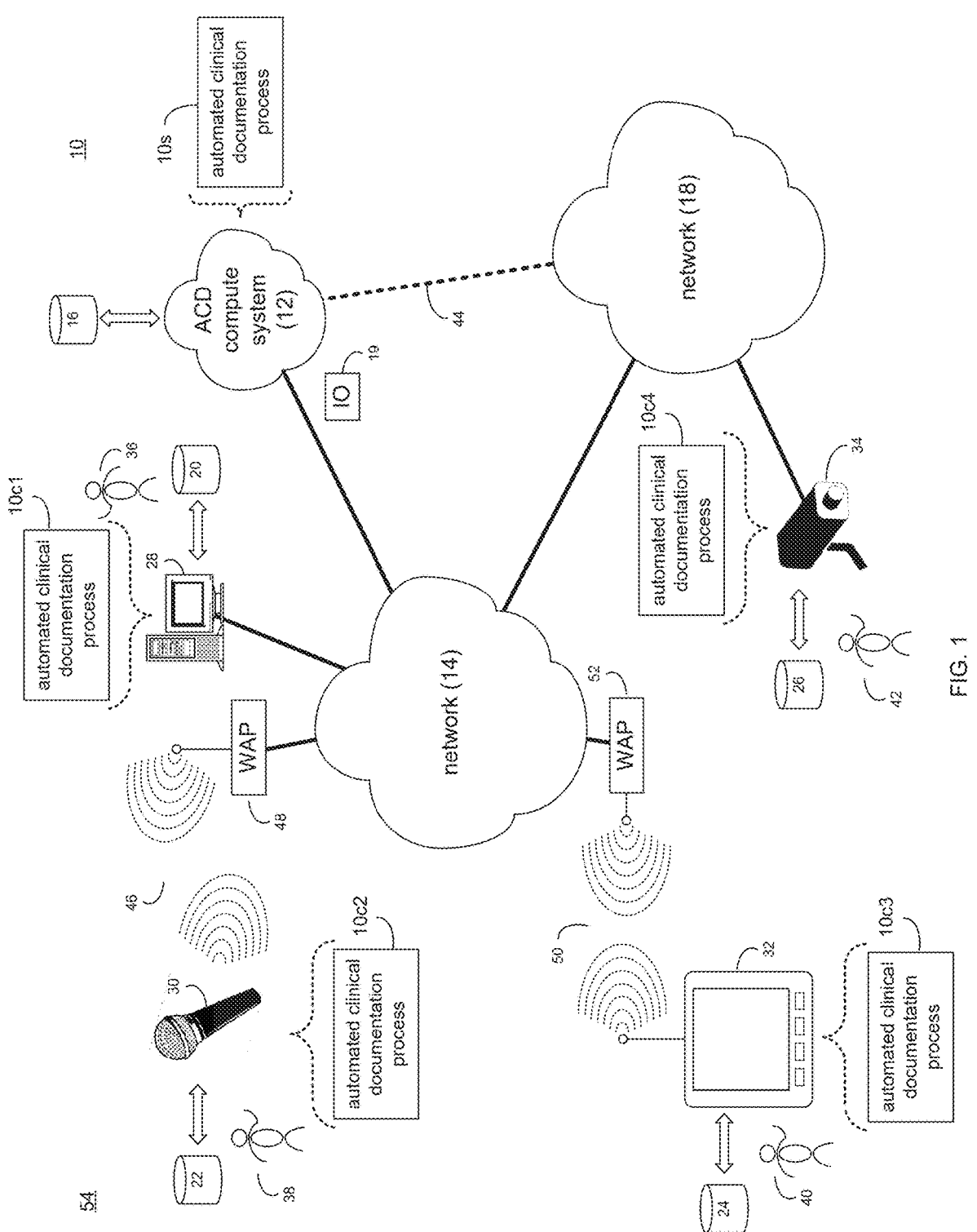
FIG. 1 is a diagrammatic view of an automated clinical documentation compute system and an automated clinical documentation process coupled to a distributed computing network.

System Overview:

Referring to FIG. 1, there is shown automated clinical documentation process 10. As will be discussed below in greater detail, automated clinical documentation process 10 may be configured to automate the collection and processing of clinical encounter information to generate/store/distribute medical records.

Automated clinical documentation process 10 may be implemented as a server-side process, a client-side process, or a hybrid server-side/client-side process. For example, automated clinical documentation process 10 may be implemented as a purely server-side process via automated clinical documentation process 10s. Alternatively, automated clinical documentation process 10 may be implemented as a purely client-side process via one or more of automated clinical documentation process 10c1, automated clinical documentation process 10c2, automated clinical documentation process 10c3, and automated clinical documentation process 10c4. Alternatively still, automated clinical documentation process 10 may be implemented as a hybrid server-side/client-side process via automated clinical documentation process 10s in combination with one or more of automated clinical documentation process 10c1, automated clinical documentation process 10c2, automated clinical documentation process 10c3, and automated clinical documentation process 10c4.

Accordingly, automated clinical documentation process 10 as used in this disclosure may include any combination of automated clinical documentation process 10s, automated clinical documentation process 10c1, automated clinical documentation process 10c2, automated clinical documentation process 10c3, and automated clinical documentation process 10c4.

Automated clinical documentation process 10s may be a server application and may reside on and may be executed by automated clinical documentation (ACD) compute system 12, which may be connected to network 14 (e.g., the Internet or a local area network). ACD compute system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

As is known in the art, a SAN may include one or more of a personal computer, a server computer, a series of server computers, a mini computer, a mainframe computer, a RAID device and a NAS system. The various components of ACD compute system 12 may execute one or more operating systems, examples of which may include but are not limited to: Microsoft Windows Server™; Redhat Linux™, Unix, or a custom operating system, for example.

The instruction sets and subroutines of automated clinical documentation process 10s, which may be stored on storage device 16 coupled to ACD compute system 12, may be executed by one or more processors (not shown) and one or more memory architectures (not shown) included within ACD compute system 12. Examples of storage device 16 may include but are not limited to: a hard disk drive; a RAID device; a random-access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Various IO requests (e.g. IO request 19) may be sent from automated clinical documentation process 10s, automated clinical documentation process 10c1, automated clinical documentation process 10c2, automated clinical documentation process 10c3 and/or automated clinical documentation process 10c4 to ACD compute system 12. Examples of IO request 19 may include but are not limited to data write requests (i.e. a request that content be written to ACD compute system 12) and data read requests (i.e. a request that content be read from ACD compute system 12).

The instruction sets and subroutines of automated clinical documentation process 10c1, automated clinical documentation process 10c2, automated clinical documentation process 10c3 and/or automated clinical documentation process 10c4, which may be stored on storage devices 20, 22, 24, 26 (respectively) coupled to ACD client electronic devices 28, 30, 32, 34 (respectively), may be executed by one or more processors (not shown) and one or more memory architectures (not shown) incorporated into ACD client electronic devices 28, 30, 32, 34 (respectively). Storage devices 20, 22, 24, 26 may include but are not limited to: hard disk drives; optical drives; RAID devices; random access memories (RAM); read-only memories (ROM), and all forms of flash memory storage devices. Examples of ACD client electronic devices 28, 30, 32, 34 may include, but are not limited to, personal computing device 28 (e.g., a smart phone, a personal digital assistant, a laptop computer, a notebook computer, and a desktop computer), audio input device 30 (e.g., a handheld microphone, a lapel microphone, an embedded microphone (such as those embedded within eyeglasses, smart phones, tablet computers and/or watches) and an audio recording device), display device 32 (e.g., a tablet computer, a computer monitor, and a smart television), machine vision input device 34 (e.g., an RGB imaging system, an infrared imaging system, an ultraviolet imaging system, a laser imaging system, a SONAR imaging system, a RADAR imaging system, and a thermal imaging system), a hybrid device (e.g., a single device that includes the functionality of one or more of the above-references devices; not shown), an audio rendering device (e.g., a speaker system, a headphone system, or an earbud system; not shown), various medical devices (e.g., medical imaging equipment, heart monitoring machines, body weight scales, body temperature thermometers, and blood pressure machines; not shown), and a dedicated network device (not shown).

Users 36, 38, 40, 42 may access ACD compute system 12 directly through network 14 or through secondary network 18. Further, ACD compute system 12 may be connected to network 14 through secondary network 18, as illustrated with link line 44.

The various ACD client electronic devices (e.g., ACD client electronic devices 28, 30, 32, 34) may be directly or indirectly coupled to network 14 (or network 18). For example, personal computing device 28 is shown directly coupled to network 14 via a hardwired network connection. Further, machine vision input device 34 is shown directly coupled to network 18 via a hardwired network connection. Audio input device 30 is shown wirelessly coupled to network 14 via wireless communication channel 46 established between audio input device 30 and wireless access point (i.e., WAP) 48, which is shown directly coupled to network 14. WAP 48 may be, for example, an IEEE 802.11a, 802.11b, 802.11g, 802.11n, Wi-Fi, and/or Bluetooth device that is capable of establishing wireless communication channel 46 between audio input device 30 and WAP 48. Display device 32 is shown wirelessly coupled to network 14 via wireless communication channel 50 established between display device 32 and WAP 52, which is shown directly coupled to network 14.

The various ACD client electronic devices (e.g., ACD client electronic devices 28, 30, 32, 34) may each execute an operating system, examples of which may include but are not limited to Microsoft Windows™, Apple Macintosh™, Redhat Linux™, or a custom operating system, wherein the combination of the various ACD client electronic devices (e.g., ACD client electronic devices 28, 30, 32, 34) and ACD compute system 12 may form modular ACD system 54.

Figure 2:
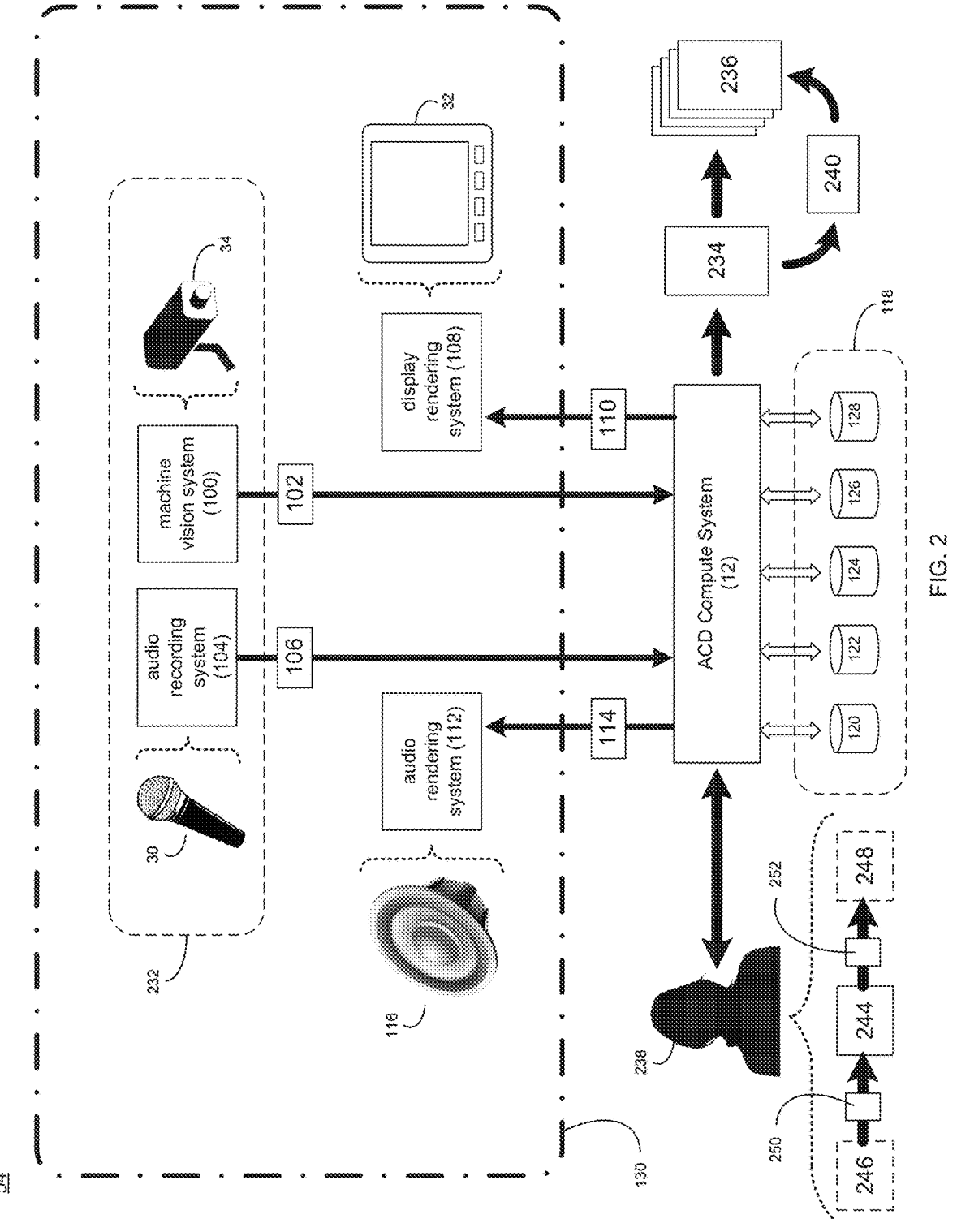
FIG. 2 is a diagrammatic view of a modular ACD system incorporating the automated clinical documentation compute system of FIG. 1.

The Automated Clinical Documentation System:

Referring also to FIG. 2, there is shown a simplified exemplary embodiment of modular ACD system 54 that is configured to automate clinical documentation. Modular ACD system 54 may include: machine vision system 100 configured to obtain machine vision encounter information 102 concerning a patient encounter; audio recording system 104 configured to obtain audio encounter information 106 concerning the patient encounter; and a compute system (e.g., ACD compute system 12) configured to receive machine vision encounter information 102 and audio encounter information 106 from machine vision system 100 and audio recording system 104 (respectively). Modular ACD system 54 may also include: display rendering system 108 configured to render visual information 110; and audio rendering system 112 configured to render audio information 114, wherein ACD compute system 12 may be configured to provide visual information 110 and audio information 114 to display rendering system 108 and audio rendering system 112 (respectively).

Example of machine vision system 100 may include but are not limited to: one or more ACD client electronic devices (e.g., ACD client electronic device 34, examples of which may include but are not limited to an RGB imaging system, an infrared imaging system, an ultraviolet imaging system, a laser imaging system, a SONAR imaging system, a RADAR imaging system, and a thermal imaging system). Examples of audio recording system 104 may include but are not limited to: one or more ACD client electronic devices (e.g., ACD client electronic device 30, examples of which may include but are not limited to a handheld microphone, a lapel microphone, an embedded microphone (such as those embedded within eyeglasses, smart phones, tablet computers and/or watches) and an audio recording device). Examples of display rendering system 108 may include but are not limited to: one or more ACD client electronic devices (e.g., ACD client electronic device 32, examples of which may include but are not limited to a tablet computer, a computer monitor, and a smart television). Examples of audio rendering system 112 may include but are not limited to: one or more ACD client electronic devices (e.g., audio rendering device 116, examples of which may include but are not limited to a speaker system, a headphone system, and an earbud system).

As will be discussed below in greater detail, ACD compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource. While in this particular example, five different examples of datasources 118, are shown, this is for illustrative purposes only and is not intended to be a limitation of this disclosure, as other configurations are possible and are considered to be within the scope of this disclosure.

As will be discussed below in greater detail, modular ACD system 54 may be configured to monitor a monitored space (e.g., monitored space 130) in a clinical environment, wherein examples of this clinical environment may include but are not limited to: a doctor's office, a medical facility, a medical practice, a medical lab, an urgent care facility, a medical clinic, an emergency room, an operating room, a hospital, a long term care facility, a rehabilitation facility, a nursing home, and a hospice facility. Accordingly, an example of the above-referenced patient encounter may include but is not limited to a patient visiting one or more of the above-described clinical environments (e.g., a doctor's office, a medical facility, a medical practice, a medical lab, an urgent care facility, a medical clinic, an emergency room, an operating room, a hospital, a long-term care facility, a rehabilitation facility, a nursing home, and a hospice facility).

Machine vision system 100 may include a plurality of discrete machine vision systems when the above-described clinical environment is larger or a higher level of resolution is desired. As discussed above, examples of machine vision system 100 may include but are not limited to: one or more ACD client electronic devices (e.g., ACD client electronic device 34, examples of which may include but are not limited to an RGB imaging system, an infrared imaging system, an ultraviolet imaging system, a laser imaging system, a SONAR imaging system, a RADAR imaging system, and a thermal imaging system). Accordingly, machine vision system 100 may include one or more of each of an RGB imaging system, an infrared imaging systems, an ultraviolet imaging systems, a laser imaging system, a SONAR imaging system, a RADAR imaging system, and a thermal imaging system.

Audio recording system 104 may include a plurality of discrete audio recording systems when the above-described clinical environment is larger or a higher level of resolution is desired. As discussed above, examples of audio recording system 104 may include but are not limited to: one or more ACD client electronic devices (e.g., ACD client electronic device 30, examples of which may include but are not limited to a handheld microphone, a lapel microphone, an embedded microphone (such as those embedded within eyeglasses, smart phones, tablet computers and/or watches) and an audio recording device). Accordingly, audio recording system 104 may include one or more of each of a handheld microphone, a lapel microphone, an embedded microphone (such as those embedded within eyeglasses, smart phones, tablet computers and/or watches) and an audio recording device.

Display rendering system 108 may include a plurality of discrete display rendering systems when the above-described clinical environment is larger or a higher level of resolution is desired. As discussed above, examples of display rendering system 108 may include but are not limited to: one or more ACD client electronic devices (e.g., ACD client electronic device 32, examples of which may include but are not limited to a tablet computer, a computer monitor, and a smart television). Accordingly, display rendering system 108 may include one or more of each of a tablet computer, a computer monitor, and a smart television.

Audio rendering system 112 may include a plurality of discrete audio rendering systems when the above-described clinical environment is larger or a higher level of resolution is desired. As discussed above, examples of audio rendering system 112 may include but are not limited to: one or more ACD client electronic devices (e.g., audio rendering device 116, examples of which may include but are not limited to a speaker system, a headphone system, or an earbud system). Accordingly, audio rendering system 112 may include one or more of each of a speaker system, a headphone system, or an earbud system.

ACD compute system 12 may include a plurality of discrete compute systems. As discussed above, ACD compute system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform. Accordingly, ACD compute system 12 may include one or more of each of a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

Figure 3:
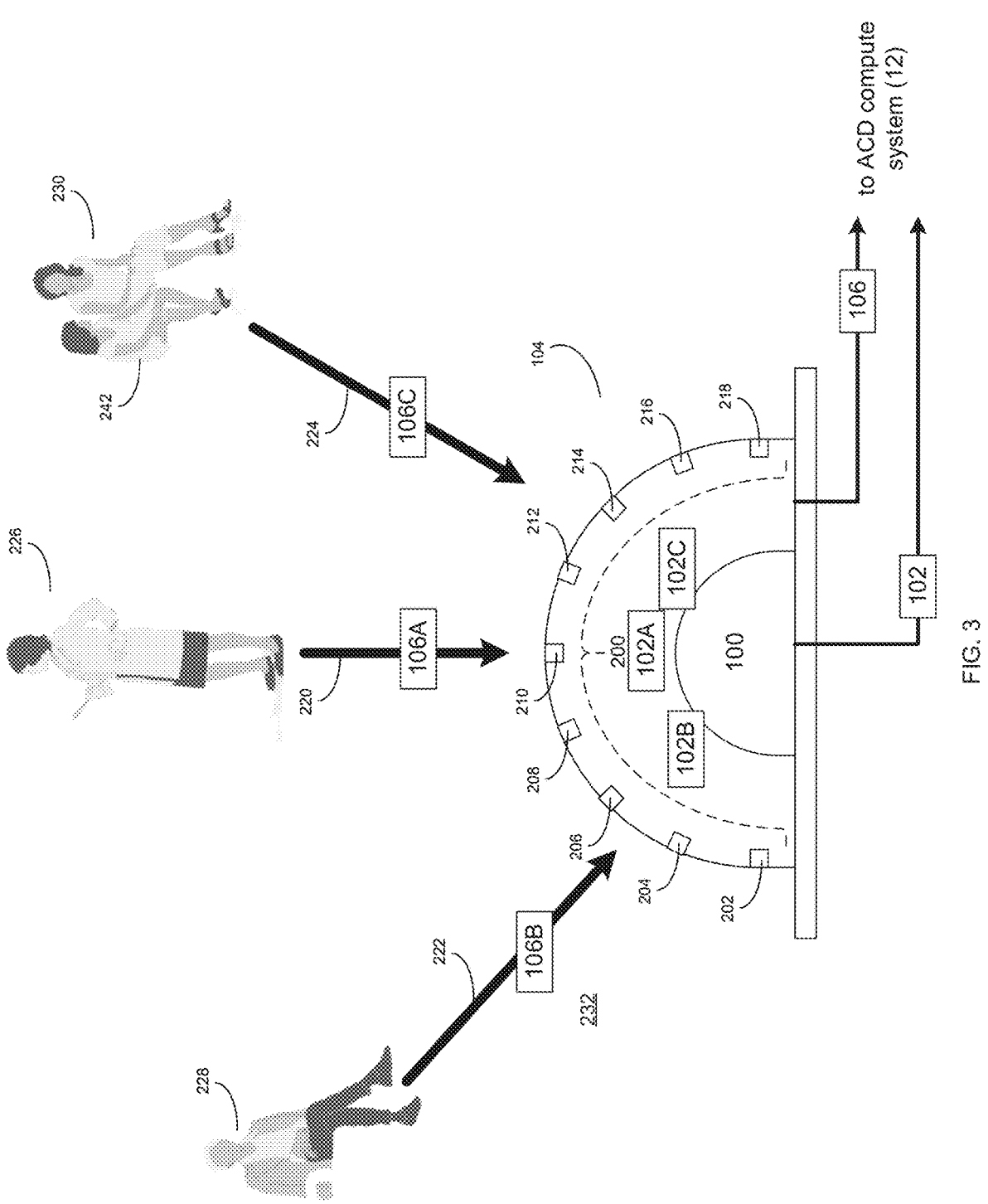
FIG. 3 is a diagrammatic view of a mixed-media ACD device included within the modular ACD system of FIG. 2.

Referring also to FIG. 3, audio recording system 104 may include directional microphone array 200 having a plurality of discrete microphone assemblies. For example, audio recording system 104 may include a plurality of discrete audio acquisition devices (e.g., audio acquisition devices 202, 204, 206, 208, 210, 212, 214, 216, 218) that may form microphone array 200. As will be discussed below in greater detail, modular ACD system 54 may be configured to form one or more audio recording beams (e.g., audio recording beams 220, 222, 224) via the discrete audio acquisition devices (e.g., audio acquisition devices 202, 204, 206, 208, 210, 212, 214, 216, 218) included within audio recording system 104.

For example, modular ACD system 54 may be further configured to steer the one or more audio recording beams (e.g., audio recording beams 220, 222, 224) toward one or more encounter participants (e.g., encounter participants 226, 228, 230) of the above-described patient encounter. Examples of the encounter participants (e.g., encounter participants 226, 228, 230) may include but are not limited to: medical professionals (e.g., doctors, nurses, physician's assistants, lab technicians, physical therapists, scribes (e.g., a transcriptionist) and/or staff members involved in the patient encounter), patients (e.g., people that are visiting the above-described clinical environments for the patient encounter), and third parties (e.g., friends of the patient, relatives of the patient and/or acquaintances of the patient that are involved in the patient encounter).

Accordingly, modular ACD system 54 and/or audio recording system 104 may be configured to utilize one or more of the discrete audio acquisition devices (e.g., audio acquisition devices 202, 204, 206, 208, 210, 212, 214, 216, 218) to form an audio recording beam. For example, modular ACD system 54 and/or audio recording system 104 may be configured to utilize audio acquisition device 210 to form audio recording beam 220, thus enabling the capturing of audio (e.g., speech) produced by encounter participant 226 (as audio acquisition device 210 is pointed to (i.e., directed toward) encounter participant 226). Additionally, modular ACD system 54 and/or audio recording system 104 may be configured to utilize audio acquisition devices 204, 206 to form audio recording beam 222, thus enabling the capturing of audio (e.g., speech) produced by encounter participant 228 (as audio acquisition devices 204, 206 are pointed to (i.e., directed toward) encounter participant 228). Additionally, modular ACD system 54 and/or audio recording system 104 may be configured to utilize audio acquisition devices 212, 214 to form audio recording beam 224, thus enabling the capturing of audio (e.g., speech) produced by encounter participant 230 (as audio acquisition devices 212, 214 are pointed to (i.e., directed toward) encounter participant 230). Further, modular ACD system 54 and/or audio recording system 104 may be configured to utilize null-steering precoding to cancel interference between speakers and/or noise.

As is known in the art, null-steering precoding is a method of spatial signal processing by which a multiple antenna transmitter may null multiuser interference signals in wireless communications, wherein null-steering precoding may mitigate the impact off background noise and unknown user interference.

In particular, null-steering precoding may be a method of beamforming for narrowband signals that may compensate for delays of receiving signals from a specific source at different elements of an antenna array. In general and to improve performance of the antenna array, in incoming signals may be summed and averaged, wherein certain signals may be weighted and compensation may be made for signal delays.

Machine vision system 100 and audio recording system 104 may be stand-alone devices (as shown in FIG. 2). Additionally/alternatively, machine vision system 100 and audio recording system 104 may be combined into one package to form mixed-media ACD device 232. For example, mixed-media ACD device 232 may be configured to be mounted to a structure (e.g., a wall, a ceiling, a beam, a column) within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility), thus allowing for easy installation of the same. Further, modular ACD system 54 may be configured to include a plurality of mixed-media ACD devices (e.g., mixed-media ACD device 232) when the above-described clinical environment is larger or a higher level of resolution is desired.

The Mixed-Media Automated Clinical Documentation Device:

Modular ACD system 54 may be further configured to steer the one or more audio recording beams (e.g., audio recording beams 220, 222, 224) toward one or more encounter participants (e.g., encounter participants 226, 228, 230) of the patient encounter based, at least in part, upon machine vision encounter information 102. As discussed above, mixed-media ACD device 232 (and machine vision system 100/audio recording system 104 included therein) may be configured to monitor one or more encounter participants (e.g., encounter participants 226, 228, 230) of a patient encounter.

Specifically and as will be discussed below in greater detail, machine vision system 100 (either as a stand-alone system or as a component of mixed-media ACD device 232) may be configured to detect humanoid shapes within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility). And when these humanoid shapes are detected by machine vision system 100, modular ACD system 54 and/or audio recording system 104 may be configured to utilize one or more of the discrete audio acquisition devices (e.g., audio acquisition devices 202, 204, 206, 208, 210, 212, 214, 216, 218) to form an audio recording beam (e.g., audio recording beams 220, 222, 224) that is directed toward each of the detected humanoid shapes (e.g., encounter participants 226, 228, 230).

As discussed above, ACD compute system 12 may be configured to receive machine vision encounter information 102 and audio encounter information 106 from machine vision system 100 and audio recording system 104 (respectively); and may be configured to provide visual information 110 and audio information 114 to display rendering system 108 and audio rendering system 112 (respectively). Depending upon the manner in which modular ACD system 54 (and/or mixed-media ACD device 232) is configured, ACD compute system 12 may be included within mixed-media ACD device 232 or external to mixed-media ACD device 232.

The Automated Clinical Documentation Process:

As discussed above, ACD compute system 12 may execute all or a portion of automated clinical documentation process 10, wherein the instruction sets and subroutines of automated clinical documentation process 10 (which may be stored on one or more of e.g., storage devices 16, 20, 22, 24, 26) may be executed by ACD compute system 12 and/or one or more of ACD client electronic devices 28, 30, 32, 34.

Figure 4:
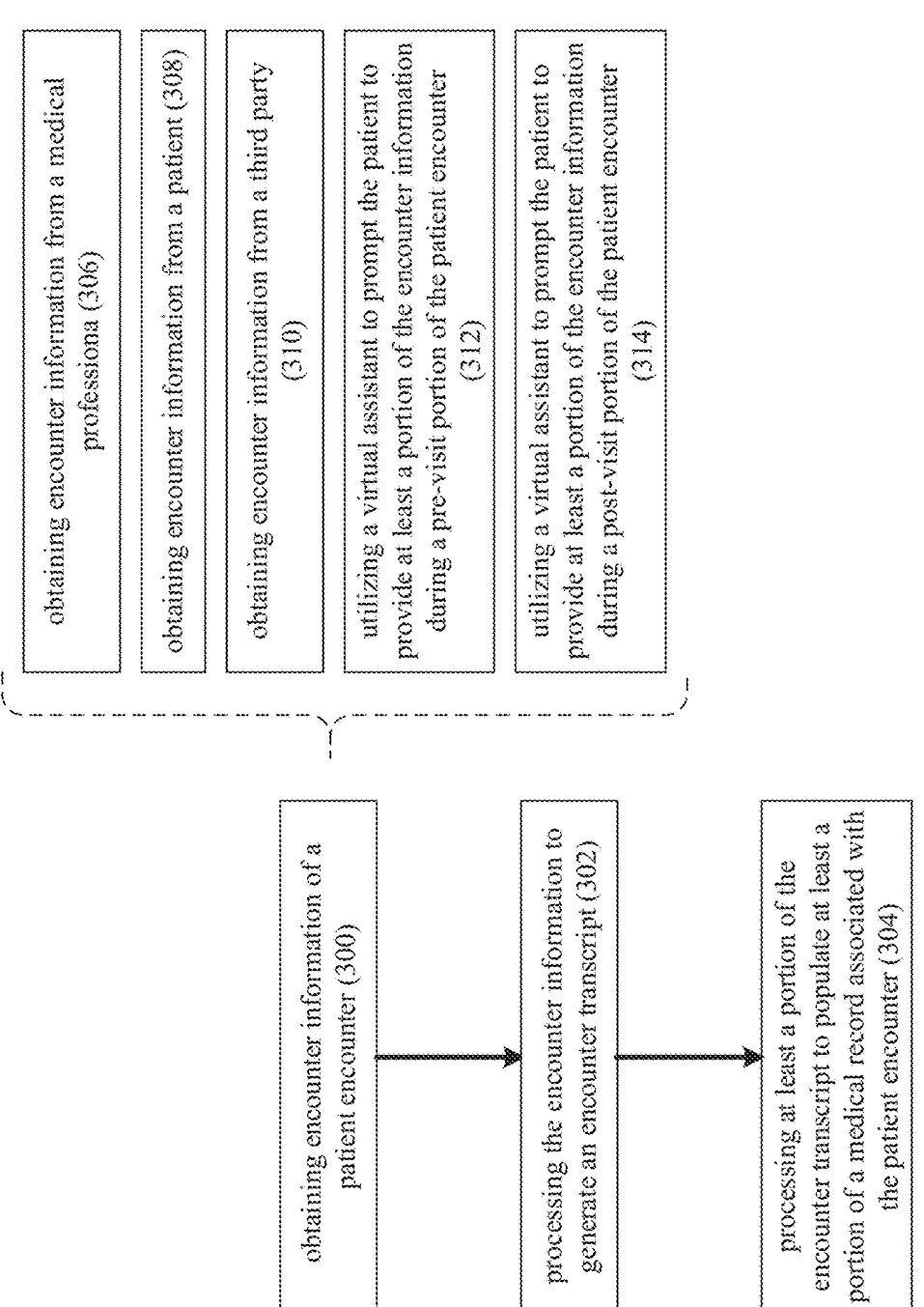
FIG. 4 is a flow chart of one implementation of the automated clinical documentation process of FIG. 1.

As discussed above, automated clinical documentation process 10 may be configured to automate the collection and processing of clinical encounter information to generate/store/distribute medical records. Accordingly and referring also to FIG. 4, automated clinical documentation process 10 may be configured to obtain 300 encounter information (e.g., machine vision encounter information 102 and/or audio encounter information 106) of a patient encounter (e.g., a visit to a doctor's office). Automated clinical documentation process 10 may further be configured to process 302 the encounter information (e.g., machine vision encounter information 102 and/or audio encounter information 106) to generate an encounter transcript (e.g., encounter transcript 234), wherein automated clinical documentation process 10 may then process 304 at least a portion of the encounter transcript (e.g., encounter transcript 234) to populate at least a portion of a medical record (e.g., medical record 236) associated with the patient encounter (e.g., the visit to the doctor's office). Encounter transcript 234 and/or medical record 236 may be reviewed by a medical professional involved with the patient encounter (e.g., a visit to a doctor's office) to determine the accuracy of the same and/or make corrections to the same.

For example, a scribe involved with (or assigned to) the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, automated clinical documentation process 10 may utilize these corrections for training/tuning purposes (e.g., to adjust the various profiles associated the participants of the patient encounter) to enhance the future accuracy/efficiency/performance of automated clinical documentation process 10.

Alternatively/additionally, a doctor involved with the patient encounter (e.g., a visit to a doctor's office) may review encounter transcript 234 and/or medical record 236 to confirm that the same was accurate and/or make corrections to the same. In the event that corrections are made to encounter transcript 234 and/or medical record 236, automated clinical documentation process 10 may utilize these corrections for training/tuning purposes (e.g., to adjust the various profiles associated the participants of the patient encounter) to enhance the future accuracy/efficiency/performance of automated clinical documentation process 10.

For example, assume that a patient (e.g., encounter participant 228) visits a clinical environment (e.g., a doctor's office) because they do not feel well. They have a headache, fever, chills, a cough, and some difficulty breathing. In this particular example, a monitored space (e.g., monitored space 130) within the clinical environment (e.g., the doctor's office) may be outfitted with machine vision system 100 configured to obtain machine vision encounter information 102 concerning the patient encounter (e.g., encounter participant 228 visiting the doctor's office) and audio recording system 104 configured to obtain audio encounter information 106 concerning the patient encounter (e.g., encounter participant 228 visiting the doctor's office) via one or more audio sensors (e.g., audio acquisition devices 202, 204, 206, 208, 210, 212, 214, 216, 218).

As discussed above, machine vision system 100 may include a plurality of discrete machine vision systems if the monitored space (e.g., monitored space 130) within the clinical environment (e.g., the doctor's office) is larger or a higher level of resolution is desired, wherein examples of machine vision system 100 may include but are not limited to: an RGB imaging system, an infrared imaging system, an ultraviolet imaging system, a laser imaging system, a SONAR imaging system, a RADAR imaging system, and a thermal imaging system. Accordingly and in certain instances/embodiments, machine vision system 100 may include one or more of each of an RGB imaging system, an infrared imaging system, an ultraviolet imaging system, a laser imaging system, a SONAR imaging system, a RADAR imaging system, and a thermal imaging system positioned throughout monitored space 130, wherein each of these systems may be configured to provide data (e.g., machine vision encounter information 102) to ACD compute system 12 and/or modular ACD system 54.

As also discussed above, audio recording system 104 may include a plurality of discrete audio recording systems if the monitored space (e.g., monitored space 130) within the clinical environment (e.g., the doctor's office) is larger or a higher level of resolution is desired, wherein examples of audio recording system 104 may include but are not limited to: a handheld microphone, a lapel microphone, an embedded microphone (such as those embedded within eyeglasses, smart phones, tablet computers and/or watches) and an audio recording device. Accordingly and in certain instances/embodiments, audio recording system 104 may include one or more of each of a handheld microphone, a lapel microphone, an embedded microphone (such as those embedded within eyeglasses, smart phones, tablet computers and/or watches) and an audio recording device positioned throughout monitored space 130, wherein each of these microphones/devices may be configured to provide data (e.g., audio encounter information 106) to ACD compute system 12 and/or modular ACD system 54.

Since machine vision system 100 and audio recording system 104 may be positioned throughout monitored space 130, all of the interactions between medical professionals (e.g., encounter participant 226), patients (e.g., encounter participant 228) and third parties (e.g., encounter participant 230) that occur during the patient encounter (e.g., encounter participant 228 visiting the doctor's office) within the monitored space (e.g., monitored space 130) of the clinical environment (e.g., the doctor's office) may be monitored/recorded/processed. Accordingly, a patient "check-in" area within monitored space 130 may be monitored to obtain encounter information (e.g., machine vision encounter information 102 and/or audio encounter information 106) during this pre-visit portion of the patient encounter (e.g., encounter participant 228 visiting the doctor's office). Further, various rooms within monitored space 130 may be monitored to obtain encounter information (e.g., machine vision encounter information 102 and/or audio encounter information 106) during these various portions of the patient encounter (e.g., while meeting with the doctor, while vital signs and statistics are obtained, and while imaging is performed). Further, a patient "check-out" area within monitored space 130 may be monitored to obtain encounter information (e.g., machine vision encounter information 102 and/or audio encounter information 106) during this post-visit portion of the patient encounter (e.g., encounter participant 228 visiting the doctor's office). Additionally and via machine vision encounter information 102, visual speech recognition (via visual lip-reading functionality) may be utilized by automated clinical documentation process 10 to further effectuate the gathering of audio encounter information 106.

Accordingly and when obtaining 300 encounter information (e.g., machine vision encounter information 102 and/or audio encounter information 106), automated clinical documentation process 10 may: obtain 306 encounter information (e.g., machine vision encounter information 102 and/or audio encounter information 106) from a medical professional (e.g., encounter participant 226); obtain 308 encounter information (e.g., machine vision encounter information 102 and/or audio encounter information 106) from a patient (e.g., encounter participant 228); and/or obtain 310 encounter information (e.g., machine vision encounter information 102 and/or audio encounter information 106) from a third party (e.g., encounter participant 230). Further and when obtaining 300 encounter information (e.g., machine vision encounter information 102 and/or audio encounter information 106), automated clinical documentation process 10 may obtain 300 the encounter information (e.g., machine vision encounter information 102 and/or audio encounter information 106) from previous (related or unrelated) patient encounters. For example, if the current patient encounter is actually the third visit that the patient is making concerning e.g., shortness of breath, the encounter information from the previous two visits (i.e., the previous two patient encounters) may be highly-related and may be obtained 300 by automated clinical documentation process 10.

As will be discussed below in greater detail, when automated clinical documentation process 10 obtains 300 the encounter information, automated clinical documentation process 10 may utilize 312 a virtual assistant (e.g., virtual assistant 238) to prompt the patient (e.g., encounter participant 228) to provide at least a portion of the encounter information (e.g., machine vision encounter information 102 and/or audio encounter information 106) during a pre-visit portion (e.g., a patient intake portion) of the patient encounter (e.g., encounter participant 228 visiting the doctor's office).

Further and as will be discussed below in greater detail, when automated clinical documentation process 10 obtains 300 encounter information, automated clinical documentation process 10 may utilize 314 a virtual assistant (e.g., virtual assistant 238) to prompt the patient (e.g., encounter participant 228) to provide at least a portion of the encounter information (e.g., machine vision encounter information 102 and/or audio encounter information 106) during a post-visit portion (e.g., a patient follow-up portion) of the patient encounter (e.g., encounter participant 228 visiting the doctor's office).

As discussed above, when automated clinical documentation process 10 obtains 300 encounter information, automated clinical documentation process 10 may utilize 312 a virtual assistant (e.g., virtual assistant 238) to prompt the patient (e.g., encounter participant 228) to provide at least a portion of the encounter information (e.g., machine vision encounter information 102 and/or audio encounter information 106) during a pre-visit portion (e.g., a patient intake portion) of the patient encounter (e.g., encounter participant 228 visiting the doctor's office).

As will be discussed below in greater detail, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office).

Figure 5:
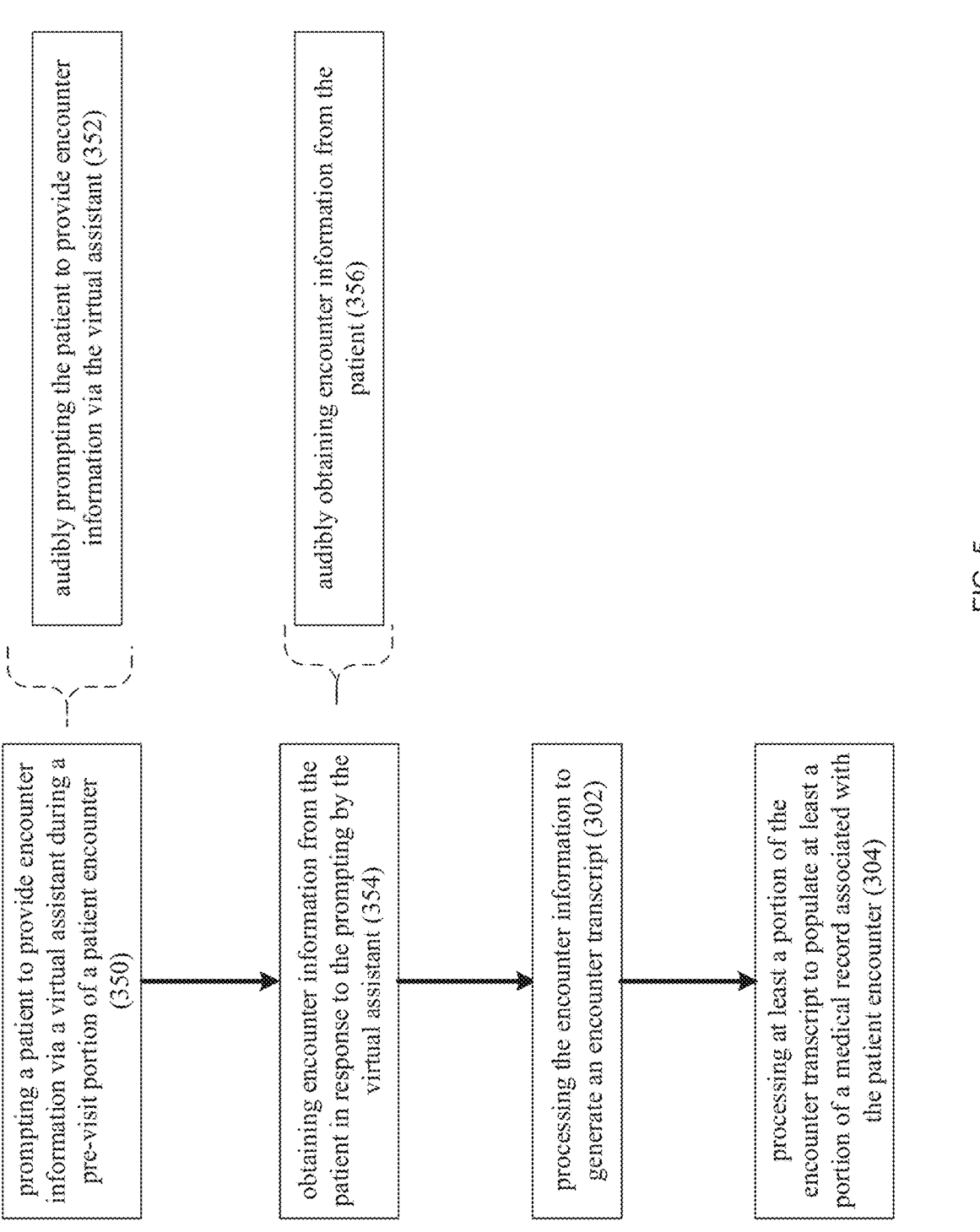
FIG. 5 is a flow chart of another implementation of the automated clinical documentation process of FIG. 1.

Accordingly and referring also to FIG. 5, automated clinical documentation process 10 may be configured to prompt 350 a patient (e.g., encounter participant 228) to provide encounter information (e.g., machine vision encounter information 102 and/or audio encounter information 106) via a virtual assistant (e.g., virtual assistant 238) during a pre-visit portion of a patient encounter (e.g., encounter participant 228 visiting the doctor's office).

For example and upon arriving for the patient encounter (e.g., encounter participant 228 visiting the doctor's office), the patient (e.g., encounter participant 228) may be directed to a "check-in" area within the monitored space (e.g., monitored space 130) of the clinical environment. An example of this "check-in" area may include a booth into which the patient (e.g., encounter participant 228) enters. Upon entering this "check-in" area, the pre-visit portion (e.g., the patient intake portion) of the patient encounter (e.g., encounter participant 228 visiting the doctor's office) may begin.

When prompting 350 the patient (e.g., encounter participant 228) to provide encounter information (e.g., machine vision encounter information 102 and/or audio encounter information 106) via the virtual assistant (e.g., virtual assistant 238), automated clinical documentation process 10 may audibly prompt 352 the patient (e.g., encounter participant 228) to provide encounter information (e.g., machine vision encounter information 102 and/or audio encounter information 106) via the virtual assistant (e.g., virtual assistant 238). For example, virtual assistant 238 may provide (via audio rendering device 116) a cordial greeting to the patient (e.g., encounter participant 228) and ask them if they are checking in for a visit. If the patient (e.g., encounter participant 228) responds affirmatively, virtual assistant 238 may audibly prompt 352 the patient (e.g., encounter participant 228) to provide encounter information (e.g., machine vision encounter information 102 and/or audio encounter information 106), examples of which may include but are not limited to: patient background information; patient current-prescription information; patient insurance information; and patient symptom information.

Therefore, virtual assistant 238 may ask the patient (e.g., encounter participant 228) to provide various pieces of identifying information, examples of which may include but are not limited to: patient name, patient social security number, and patient date of birth. Depending upon the manner in which automated clinical documentation process 10 is configured, machine vision encounter information 102 may be utilized to further enhance/expedite the check-in process. For example and via machine vision encounter information 102, facial recognition functionality may be utilized to positively identify the patient (e.g., encounter participant 228). Additionally and via machine vision encounter information 102, visual speech recognition (via visual lip-reading functionality) may be utilized by automated clinical documentation process 10 to further effectuate the gathering of audio encounter information 106. Virtual assistant 238 may ask the patient (e.g., encounter participant 228) to provide additional pieces of information, examples of which may include but are not limited to patient current-prescription information; patient insurance information; and patient symptom information.

While the pre-visit portion of the patient encounter (e.g., encounter participant 228 visiting the doctor's office) is described above as being the point of the patient encounter (e.g., encounter participant 228 visiting the doctor's office) where the patient (e.g., encounter participant 228) is entering the monitored space (e.g., monitored space 130) in a clinical environment, this is for illustrative purposes only and is not intended to be a limitation of this disclosure, as other configurations are possible and are considered to be within the scope of this disclosure. For example, this pre-visit portion of the patient encounter (e.g., encounter participant 228 visiting the doctor's office) may include: automated wellness phone calls, automated wellness text messages, and automated wellness video conferences initiated by virtual assistant 238 and directed toward the patient (e.g., encounter participant 228) or a third party; and/or phone calls, text messages, and video conferences initiated by the patient (e.g., encounter participant 228) or a third party and automatically processed by virtual assistant 238.

During this pre-visit portion (e.g., the patient intake portion) of the patient encounter (e.g., encounter participant 228 visiting the doctor's office), automated clinical documentation process 10 may obtain 354 encounter information (e.g., machine vision encounter information 102 and/or audio encounter information 106) from the patient (e.g., encounter participant 228) in response to the prompting by the virtual assistant (e.g., virtual assistant 238). When obtaining 354 the encounter information (e.g., machine vision encounter information 102 and/or audio encounter information 106) from the patient (e.g., encounter participant 228), automated clinical documentation process 10 may audibly obtain 356 the encounter information (e.g., machine vision encounter information 102 and/or audio encounter information 106) from the patient (e.g., encounter participant 228), thus allowing encounter participant 228 to simply verbalize their answers, wherein this information (e.g., audio encounter information 106) may be received via audio input device 30.

Automated clinical documentation process 10 may then process 302 the encounter information (e.g., machine vision encounter information 102 and/or audio encounter information 106) to generate an encounter transcript (e.g., encounter transcript 234), wherein at least a portion of the encounter transcript (e.g., encounter transcript 234) may be processed 304 to populate at least a portion of a medical record (e.g., medical record 236) associated with the patient encounter (e.g., a visit to a doctor's office).

As discussed above, when automated clinical documentation process 10 obtains 300 encounter information, automated clinical documentation process 10 may utilize 314 a virtual assistant (e.g., virtual assistant 238) to prompt the patient (e.g., encounter participant 228) to provide at least a portion of the encounter information (e.g., machine vision encounter information 102 and/or audio encounter information 106) during a post-visit portion (e.g., a patient follow-up portion) of the patient encounter (e.g., encounter participant 228 visiting the doctor's office.

As discussed above and as will be discussed below in greater detail, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office).

Accordingly and referring also to FIG. 6, automated clinical documentation process 10 may be configured to prompt 400 a patient (e.g., encounter participant 228) to provide encounter information (e.g., machine vision encounter information 102 and/or audio encounter information 106) via a virtual assistant (e.g., virtual assistant 238) during a post-visit portion of a patient encounter (e.g., encounter participant 228 visiting the doctor's office).

For example and upon completing the patient encounter (e.g., encounter participant 228 visiting the doctor's office), the patient (e.g., encounter participant 228) may be directed to a "check-out" area within the monitored space (e.g., monitored space 130) of the clinical environment. An example of this "check-out" area may include a booth into which the patient (e.g., encounter participant 228) enters. Upon entering this "check-out" area, the post-visit portion (e.g., the patient follow-up portion) of the patient encounter (e.g., encounter participant 228 visiting the doctor's office) may begin.

When prompting 400 the patient (e.g., encounter participant 228) to provide encounter information (e.g., machine vision encounter information 102 and/or audio encounter information 106) via the virtual assistant (e.g., virtual assistant 238), automated clinical documentation process 10 may audibly prompt 402 the patient (e.g., encounter participant 228) to provide encounter information (e.g., machine vision encounter information 102 and/or audio encounter information 106) via the virtual assistant (e.g., virtual assistant 238). For example, virtual assistant 238 may provide (via audio rendering device 116) a cordial greeting to the patient (e.g., encounter participant 228) and ask them if they are checking out. If the patient (e.g., encounter participant 228) responds affirmatively, virtual assistant 238 may audibly prompt 402 the patient (e.g., encounter participant 228) to provide encounter information (e.g., machine vision encounter information 102 and/or audio encounter information 106), examples of which may include but are not limited to: patient status information; patient medication information; and patient follow-up information.

Therefore, virtual assistant 238 may ask the patient (e.g., encounter participant 228) to provide various pieces of identifying information, examples of which may include but are not limited to: patient status information; patient medication information; and patient follow-up information. Depending upon the manner in which automated clinical documentation process 10 is configured, machine vision encounter information 102 may be utilized to further enhance/expedite the check-out process. For example and via machine vision encounter information 102, facial recognition functionality may be utilized to positively identify the patient (e.g., encounter participant 228). Additionally and via machine vision encounter information 102, visual speech recognition (via visual lip-reading functionality) may be utilized by automated clinical documentation process 10 to further effectuate the gathering of audio encounter information 106.

While the post-visit portion of the patient encounter (e.g., encounter participant 228 visiting the doctor's office) is described above as being the point of the patient encounter (e.g., encounter participant 228 visiting the doctor's office) where the patient (e.g., encounter participant 228) is leaving the monitored space (e.g., monitored space 130) in a clinical environment, this is for illustrative purposes only and is not intended to be a limitation of this disclosure, as other configurations are possible and are considered to be within the scope of this disclosure. For example, this post-visit portion of the patient encounter (e.g., encounter participant 228 visiting the doctor's office) may include: automated wellness phone calls, automated wellness text messages, and automated wellness video conferences initiated by virtual assistant 238 and directed toward the patient (e.g., encounter participant 228) or a third party; and/or phone calls, text messages, and video conferences initiated by the patient (e.g., encounter participant 228) or a third party and automatically processed by virtual assistant 238.

During this post-visit portion (e.g., the patient follow-up portion) of the patient encounter (e.g., encounter participant 228 visiting the doctor's office), automated clinical documentation process 10 may obtain 404 encounter information (e.g., machine vision encounter information 102 and/or audio encounter information 106) from the patient (e.g., encounter participant 228) in response to the prompting by the virtual assistant (e.g., virtual assistant 238). When obtaining 404 encounter information (e.g., machine vision encounter information 102 and/or audio encounter information 106) from the patient (e.g., encounter participant 228), automated clinical documentation process 10 may audibly obtain 406 encounter information (e.g., machine vision encounter information 102 and/or audio encounter information 106) from the patient (e.g., encounter participant 228), thus allowing encounter participant 228 to simply verbalize their answers, wherein this information (e.g., audio encounter information 106) may be received via audio input device 30.

Automated clinical documentation process 10 may then process 302 the encounter information (e.g., machine vision encounter information 102 and/or audio encounter information 106) to generate an encounter transcript (e.g., encounter transcript 234), wherein at least a portion of the encounter transcript (e.g., encounter transcript 234) may be processed 304 to populate at least a portion of a medical record (e.g., medical record 236) associated with the patient encounter (e.g., a visit to a doctor's office).

Automated clinical documentation process 10 may be configured to monitor the interaction between the patient (e.g., encounter participant 228) and the medical professionals (e.g., a doctor, a nurse, a physician's assistant, a lab technician, a physical therapist and/or a staff member involved in the patient encounter) during the patient encounter (e.g., encounter participant 228 visiting the doctor's office) to determine if any potential medical situations are missed.

Figure 7:
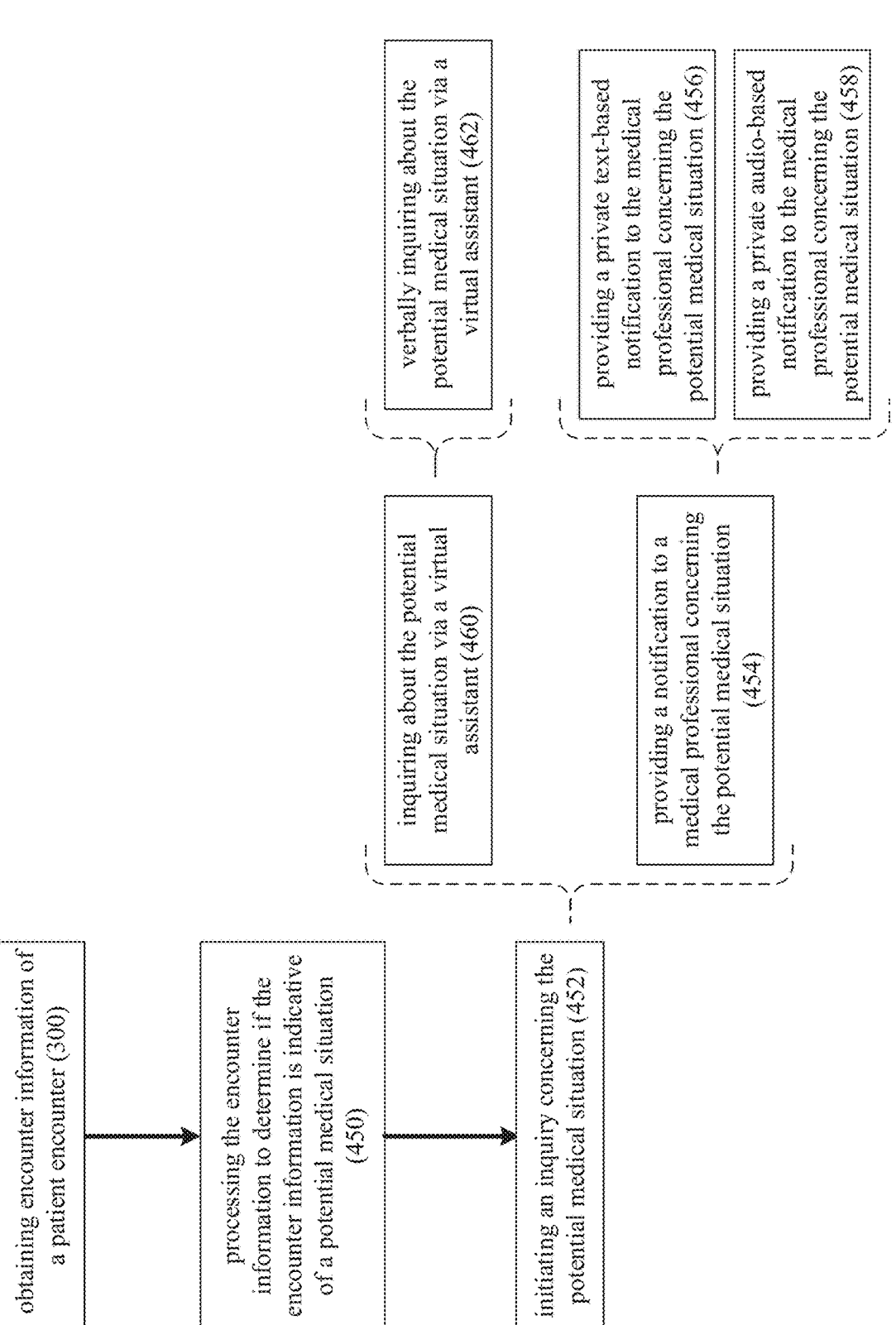
FIG. 7 is a flow chart of another implementation of the automated clinical documentation process of FIG. 1.

Accordingly and referring also to FIG. 7, automated clinical documentation process 10 may obtain 300 encounter information (e.g., machine vision encounter information 102 and/or audio encounter information 106) of a patient encounter (e.g., a visit to a doctor's office).

As discussed above, since machine vision system 100 and audio recording system 104 may be positioned throughout monitored space 130, all of the interactions between medical professionals (e.g., encounter participant 226), patients (e.g., encounter participant 228) and third parties (e.g., encounter participant 230) that occur during the patient encounter (e.g., encounter participant 228 visiting the doctor's office) within the monitored space (e.g., monitored space 130) of the clinical environment (e.g., the doctor's office) may be monitored/recorded/processed. Accordingly, a patient "check-in" area within monitored space 130 may be monitored to obtain encounter information (e.g., machine vision encounter information 102 and/or audio encounter information 106) during this pre-visit portion of the patient encounter (e.g., encounter participant 228 visiting the doctor's office). Additionally and as discussed above, this pre-visit encounter information may be obtained via e.g., virtual assistant 238 before the patient (e.g., encounter participant 228) has entered monitored space 130. Further, various rooms within monitored space 130 may be monitored to obtain encounter information (e.g., machine vision encounter information 102 and/or audio encounter information 106) during these various portions of the patient encounter (e.g., while meeting with the doctor, while vital signs and statistics are obtained, and while imaging is performed). Further, a patient "check-out" area within monitored space 130 may be monitored to obtain encounter information (e.g., machine vision encounter information 102 and/or audio encounter information 106) during this post-visit portion of the patient encounter (e.g., encounter participant 228 visiting the doctor's office). Additionally and as discussed above, this post-visit encounter information may be obtained via e.g., virtual assistant 238 after the patient (e.g., encounter participant 228) has left monitored space 130. Further and via machine vision encounter information 102, visual speech recognition (via visual lip-reading functionality) may be utilized by automated clinical documentation process 10 to further effectuate the gathering of audio encounter information 106.

Accordingly, a complete recording of the patient encounter (e.g., encounter participant 228 visiting the doctor's office) may be generated, wherein this encounter information (e.g., machine vision encounter information 102 and/or audio encounter information 106) may be processed 302 to generate an encounter transcript (e.g., encounter transcript 234) and at least a portion of this encounter transcript (e.g., encounter transcript 234) may be processed 304 to populate at least a portion of a medical record (e.g., medical record 236) associated with the patient encounter (e.g., the visit to the doctor's office).

Automated clinical documentation process 10 may process 450 the encounter information (e.g., machine vision encounter information 102 and/or audio encounter information 106) to determine if the encounter information (e.g., machine vision encounter information 102 and/or audio encounter information 106) is indicative of a potential medical situation, wherein examples of these potential medical situations may include but are not limited to one or more of: a potential medical condition; a potential medication issue; a potential home healthcare issue; and a potential follow-up issue.

As discussed above, ACD compute system 12 may be configured to access one or more datasources (e.g., datasources 118), wherein examples of datasources 118 may include a medical conditions symptoms datasource (e.g., that defines the symptoms for various diseases and medical conditions), a prescriptions compatibility datasource (e.g., that defines groups of prescriptions that are substitutable for (or compatible with) each other), a medical insurance coverage datasource (e.g., that defines what prescriptions are covered by various medical insurance providers), and a home healthcare datasource (e.g., that defines best practices concerning when home healthcare is advisable). Accordingly, automated clinical documentation process 10 may process 450 the data included within the encounter information (e.g., machine vision encounter information 102 and/or audio encounter information 106) to compare this data to data defined within the datasources (e.g., datasources 118) to determine if the encounter information (e.g., machine vision encounter information 102 and/or audio encounter information 106) is indicative of a potential medical situation.

For example, assume that the encounter information (e.g., machine vision encounter information 102 and/or audio encounter information 106) indicates that the patient (e.g., encounter participant 228) mentioned during the patient encounter (e.g., encounter participant 228 visiting the doctor's office) that their wound was healing slowly. Can that be indicative of high blood sugar? Further suppose that the encounter information (e.g., machine vision encounter information 102 and/or audio encounter information 106) indicates that the patient (e.g., encounter participant 228) is quite elderly, lives alone and now needs to take injectable medication every day for the next week. Should home health care be arranged to medicate this patient? Additionally, suppose the encounter information (e.g., machine vision encounter information 102 and/or audio encounter information 106) indicates that the doctor (e.g., encounter participant 226) prescribed medication X. Does the patient's medical insurance cover Medication X (or do they only cover Medication Y)?

If a potential medical situation is identified, automated clinical documentation process 10 may initiate 452 an inquiry concerning the potential medical situation. When initiating 452 an inquiry concerning the potential medical situation, automated clinical documentation process 10 may provide 454 a notification (e.g., as visual information 110 and/or audio information 114) to a medical professional (e.g., a doctor, a nurse, a physician's assistant, a lab technician, a physical therapist and/or a staff member involved in the patient encounter) concerning the potential medical situation. Example of such an inquiry may be asking one or more questions, such as "Does this patient have diabetes?", "Should we arrange home healthcare for this patient?" of "Would you like to substitute Medication Y for Medication X?"

When providing 454 a notification (e.g., as visual information 110 and/or audio information 114) to a medical professional (e.g., a doctor, a nurse, a physician's assistant, a lab technician, a physical therapist and/or a staff member involved in the patient encounter) concerning the potential medical situation, automated clinical documentation process 10 may provide 456 a private text-based notification (e.g., as visual information 110) to the medical professional (e.g., a doctor, a nurse, a physician's assistant, a lab technician, a physical therapist and/or a staff member involved in the patient encounter) concerning the potential medical situation. This private text-based notification (e.g., as visual information 110) may be provided to the medical professional on e.g., a private display device, examples of which may include but are not limited to a smart phone, a table computer, a notebook computer, or a desktop computer.

When providing 454 a notification (e.g., as visual information 110 and/or audio information 114) to a medical professional (e.g., a doctor, a nurse, a physician's assistant, a lab technician, a physical therapist and/or a staff member involved in the patient encounter) concerning the potential medical situation, automated clinical documentation process 10 may provide 458 a private audio-based notification (e.g., as audio information 114) to the medical professional (e.g., a doctor, a nurse, a physician's assistant, a lab technician, a physical therapist and/or a staff member involved in the patient encounter) concerning the potential medical situation. This private audio-based notification (e.g., as audio information 114) may be provided to the medical professional on e.g., a private audio device, examples of which may include but are not limited to a smart phone, or an earbud.

Alternatively, when initiating 452 an inquiry concerning the potential medical situation, automated clinical documentation process 10 may inquire 460 about the potential medical situation via a virtual assistant (e.g., virtual assistant 238), wherein inquiring 460 about the potential medical situation via a virtual assistant (e.g., virtual assistant 238) may include verbally inquiring 462 about the potential medical situation via a virtual assistant (e.g., virtual assistant 238). For example and in such a configuration, when initiating 452 the inquiry, automated clinical documentation process 10 may inquire 460 about the potential medical situation by having virtual assistant 238 verbally (and publically) inquire 462 by asking one or more questions, such as "Does this patient have diabetes?", "Should we arrange home healthcare for this patient?" of "Would you like to substitute Medication Y for Medication X?"

Automated clinical documentation process 10 may be configured to simultaneously render content to multiple output devices at varying levels of detail, as it may be desirable to not broadcast certain "sensitive" content within the examination room.

Accordingly and referring also to FIG. 8, automated clinical documentation process 10 may obtain 300 encounter information (e.g., machine vision encounter information 102 and/or audio encounter information 106) of a patient encounter (e.g., a visit to a doctor's office). Assume that during the course of the patient encounter (e.g., a visit to a doctor's office), a medical professional (e.g., a doctor, a nurse, a physician's assistant, a lab technician, a physical therapist and/or a staff member involved in the patient encounter) wishes to render a piece of content for viewing. For example and as discussed above, during the various portions of the patient encounter (e.g., a visit to a doctor's office), various procedures may occur, an example of which includes but is not limited to an imaging procedure. Accordingly, assume that the medical professional would like to display one or more images for viewing within the monitored space (e.g., monitored space 130). Accordingly, automated clinical documentation process 10 may be configured to receive 500 a request to render clinical content (e.g., an x-ray image) during a patient encounter (e.g., a visit to a doctor's office). This rendering request may be in the form of a verbal request (e.g., audio encounter information 106) that is spoken by e.g., a medical professional or a computer-based request that is initiated by the medical processional via ACD client electronic devices 28, 32.

Upon receiving 500 such a request, automated clinical documentation process 10 may determine 502 if the clinical content (e.g., the x-ray image) includes sensitive content. Examples of such sensitive content may include but are not limited to one or more of: sensitive image-based content; sensitive text-based content; sensitive prognosis-based content; sensitive diagnosis-based content; and sensitive complication-based content.

If the clinical content includes sensitive content, automated clinical documentation process 10 may render 504: a complete version of the clinical content (e.g., an x-ray image) on a first device (wherein the complete version of the clinical content includes the sensitive content) and a limited version of the clinical content (e.g., an x-ray image) on a second device (wherein the limited version of the clinical content excludes the sensitive content).

For this example, the first device may be a private device available only to one or more medical professionals of the patient encounter (e.g., a visit to a doctor's office). Examples of such private devices may include but are not limited to a visual private device and an audible private device. For this example, the second device may be a public device available to all encounter participants of the patient encounter (e.g., a visit to a doctor's office). Examples of such public devices may include but are not limited to a visual public device.

For example, assume that upon receiving 500 a request to render the clinical content (e.g., the x-ray image), automated clinical documentation process 10 determines 502 that the clinical content (e.g., the x-ray image) does include sensitive content (e.g., a strange mass). Accordingly, automated clinical documentation process 10 may render 504 a complete version of the x-ray image (that includes annotations highlighting the strange mass) on a first device e.g., a private tablet computer only accessible to the medical professional (e.g., a doctor, a nurse, a physician's assistant, a lab technician, a physical therapist and/or a staff member involved in the patient encounter). Further, automated clinical documentation process 10 may render 504 a limited version of the x-ray image (that excludes annotations highlighting the strange mass) on a second device (e.g., a wall-mounted television within monitored space 130).

As another example, automated clinical documentation process 10 may render 504 a complete version of the patient's symptoms on a second device (e.g., a wall-mounted television within monitored space 130), wherein some of these symptoms may be indicative of diabetes. Accordingly, automated clinical documentation process 10 may render 504 a private message (e.g., as a text-based message or an audio-based message) on a first device (e.g., a private tablet computer accessible to the doctor or a private earbud worn by the doctor) indicating that some of these symptoms ay be indicative of diabetes and, therefore, the doctor may wish to order an A1C test.

Automated clinical documentation process 10 may be configured to process the encounter information (e.g., machine vision encounter information 102 and/or audio encounter information 106) to generate encounter transcript 234 that may be automatically formatted and punctuated.

Accordingly and referring also to FIG. 9, automated clinical documentation process 10 may be configured to obtain 300 encounter information (e.g., machine vision encounter information 102 and/or audio encounter information 106) of a patient encounter (e.g., a visit to a doctor's office).

When obtaining 300 encounter information (e.g., machine vision encounter information 102 and/or audio encounter information 106), automated clinical documentation process 10 may obtain 306 the encounter information (e.g., machine vision encounter information 102 and/or audio encounter information 106) from a medical professional; obtain 308 the encounter information (e.g., machine vision encounter information 102 and/or audio encounter information 106) from a patient; and/or obtain 310 the encounter information (e.g., machine vision encounter information 102 and/or audio encounter information 106) from a third party. Further and when obtaining 300 encounter information (e.g., machine vision encounter information 102 and/or audio encounter information 106), automated clinical documentation process 10 may obtain 300 the encounter information (e.g., machine vision encounter information 102 and/or audio encounter information 106) from previous (related or unrelated) patient encounters. For example, if the current patient encounter is actually the third visit that the patient is making concerning e.g., shortness of breath, the encounter information from the previous two visits (i.e., the previous two patient encounters) may be highly-related and may be obtained 300 by automated clinical documentation process 10.

As discussed above, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office).

Accordingly and when obtaining 300 encounter information (e.g., machine vision encounter information 102 and/or audio encounter information 106), automated clinical documentation process 10 may utilize 312 a virtual assistant (e.g., virtual assistant 238) to prompt the patient to provide at least a portion of the encounter information (e.g., machine vision encounter information 102 and/or audio encounter information 106) during a pre-visit portion of the patient encounter (e.g., a visit to a doctor's office).

Further and when obtaining 300 encounter information (e.g., machine vision encounter information 102 and/or audio encounter information 106), automated clinical documentation process 10 may utilize 314 a virtual assistant (e.g., virtual assistant 238) to prompt the patient to provide at least a portion of the encounter information (e.g., machine vision encounter information 102 and/or audio encounter information 106) during a post-visit portion of the patient encounter (e.g., a visit to a doctor's office).

Automated clinical documentation process 10 may process 550 the encounter information (e.g., machine vision encounter information 102 and/or audio encounter information 106) to: associate a first portion of the encounter information (e.g., machine vision encounter information 102 and/or audio encounter information 106) with a first encounter participant, and associate at least a second portion of the encounter information (e.g., machine vision encounter information 102 and/or audio encounter information 106) with at least a second encounter participant.

As discussed above, modular ACD system 54 may be configured to form one or more audio recording beams (e.g., audio recording beams 220, 222, 224) via the discrete audio acquisition devices (e.g., discrete audio acquisition devices 202, 204, 206, 208, 210, 212, 214, 216, 218) included within audio recording system 104, wherein modular ACD system 54 may be further configured to steer the one or more audio recording beams (e.g., audio recording beams 220, 222, 224) toward one or more encounter participants (e.g., encounter participants 226, 228, 230) of the above-described patient encounter.

Accordingly and continuing with the above-stated example, modular ACD system 54 may steer audio recording beam 220 toward encounter participant 226, may steer audio recording beam 222 toward encounter participant 228, and may steer audio recording beam 224 toward encounter participant 230. Accordingly and due to the directionality of audio recording beams 220, 222, 224, audio encounter information 106 may include three components, namely audio encounter information 106A (which is obtained via audio recording beam 220), audio encounter information 106B (which is obtained via audio recording beam 222) and audio encounter information 106C (which is obtained via audio recording beam 220).

Further and as discussed above, ACD compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource.

Accordingly, automated clinical documentation process 10 may process 550 the encounter information (e.g., machine vision encounter information 102 and/or audio encounter information 106) to: associate a first portion (e.g., encounter information 106A) of the encounter information (e.g., audio encounter information 106) with a first encounter participant (e.g., encounter participant 226), and associate at least a second portion (e.g., encounter information 106B, 106C) of the encounter information (e.g., audio encounter information 106) with at least a second encounter participant (e.g., encounter participants 228, 230; respectively).

Further and when processing 550 the encounter information (e.g., audio encounter information 106A, 106B, 106C), automated clinical documentation process 10 may compare each of audio encounter information 106A, 106B, 106C to the voice prints defined within the above-referenced voice print datasource so that the identity of encounter participants 226, 228, 230 (respectively) may be determined. Accordingly, if the voice print datasource includes a voice print that corresponds to one or more of the voice of encounter participant 226 (as heard within audio encounter information 106A), the voice of encounter participant 228 (as heard within audio encounter information 106B) or the voice of encounter participant 230 (as heard within audio encounter information 106C), the identity of one or more of encounter participants 226, 228, 230 may be defined. And in the event that a voice heard within one or more of audio encounter information 106A, audio encounter information 106B or audio encounter information 106C is unidentifiable, that one or more particular encounter participant may be defined as "Unknown Participant".

Once the voices of encounter participants 226, 228, 230 are processed 550, automated clinical documentation process 10 may generate 302 an encounter transcript (e.g., encounter transcript 234) based, at least in part, upon the first portion of the encounter information (e.g., audio encounter information 106A) and the at least a second portion of the encounter information (e.g., audio encounter information 106B. 106C).

Automated clinical documentation process 10 may be configured to automatically define roles for the encounter participants (e.g., encounter participants 226, 228, 230) in the patient encounter (e.g., a visit to a doctor's office).

Accordingly and referring also to FIG. 10, automated clinical documentation process 10 may be configured to obtain 300 encounter information (e.g., machine vision encounter information 102 and/or audio encounter information 106) of a patient encounter (e.g., a visit to a doctor's office).

Automated clinical documentation process 10 may then process 600 the encounter information (e.g., machine vision encounter information 102 and/or audio encounter information 106) to associate a first portion of the encounter information with a first encounter participant (e.g., encounter participant 226) and assign 602 a first role to the first encounter participant (e.g., encounter participant 226).

When processing 600 the encounter information (e.g., machine vision encounter information 102 and/or audio encounter information 106) to associate the first portion of the encounter information with the first encounter participant (e.g., encounter participant 226), automated clinical documentation process 10 may process 604 the encounter information (e.g., machine vision encounter information 102 and/or audio encounter information 106) to associate a first portion of the audio encounter information (e.g., audio encounter information 106A) with the first encounter participant (e.g., encounter participant 226).

Specifically and when processing 604 the encounter information (e.g., machine vision encounter information 102 and/or audio encounter information 106) to associate the first portion of the audio encounter information (e.g., audio encounter information 106A) with the first encounter participant (e.g., encounter participant 226), automated clinical documentation process 10 may compare 606 one or more voice prints (defined within voice print datasource) to one or more voices defined within the first portion of the audio encounter information (e.g., audio encounter information 106A); and may compare 608 one or more utterance identifiers (defined within utterance datasource) to one or more utterances defined within the first portion of the audio encounter information (e.g., audio encounter information 106A); wherein comparisons 606, 608 may allow automated clinical documentation process 10 to assign 602 a first role to the first encounter participant (e.g., encounter participant 226). For example, if the identity of encounter participant 226 can be defined via voice prints, a role for encounter participant 226 may be assigned 602 if that identity defined is associated with a role (e.g., the identity defined for encounter participant 226 is Doctor Susan Jones). Further, if an utterance made by encounter participant 226 is "I am Doctor Susan Jones", this utterance may allow a role for encounter participant 226 to be assigned 602.

When processing 600 the encounter information (e.g., machine vision encounter information 102 and/or audio encounter information 106) to associate the first portion of the encounter information with the first encounter participant (e.g., encounter participant 226), automated clinical documentation process 10 may process 610 the encounter information (e.g., machine vision encounter information 102 and/or audio encounter information 106) to associate a first portion of the machine vision encounter information (e.g., machine vision encounter information 102A) with the first encounter participant (e.g., encounter participant 226).

Specifically and when processing 610 the encounter information (e.g., machine vision encounter information 102 and/or audio encounter information 106) to associate the first portion of the machine vision encounter information (e.g., machine vision encounter information 102A) with the first encounter participant (e.g., encounter participant 226), automated clinical documentation process 10 may compare 612 one or more face prints (defined within face print datasource) to one or more faces defined within the first portion of the machine vision encounter information (e.g., machine vision encounter information 102A); compare 614 one or more wearable token identifiers (defined within wearable token identifier datasource) to one or more wearable tokens defined within the first portion of the machine vision encounter information (e.g., machine vision encounter information 102A); and compare 616 one or more interaction identifiers (defined within interaction identifier datasource) to one or more humanoid interactions defined within the first portion of the machine vision encounter information (e.g., machine vision encounter information 102A); wherein comparisons 612, 614, 616 may allow automated clinical documentation process 10 to assign 602 a first role to the first encounter participant (e.g., encounter participant 226). For example, if the identity of encounter participant 226 can be defined via face prints, a role for encounter participant 226 may be assigned 602 if that identity defined is associated with a role (e.g., the identity defined for encounter participant 226 is Doctor Susan Jones). Further, if a wearable token worn by encounter participant 226 can be identified as a wearable token assigned to Doctor Susan Jones, a role for encounter participant 226 may be assigned 602. Additionally, if an interaction made by encounter participant 226 corresponds to the type of interaction that is made by a doctor, the existence of this interaction may allow a role for encounter participant 226 to be assigned 602.

Examples of such wearable tokens may include but are not limited to wearable devices that may be worn by the medical professionals when they are within monitored space 130 (or after they leave monitored space 130). For example, these wearable tokens may be worn by medical professionals when e.g., they are moving between monitored rooms within monitored space 130, travelling to and/or from monitored space 130, and/or outside of monitored space 130 (e.g., at home).

Additionally, automated clinical documentation process 10 may process 618 the encounter information (e.g., machine vision encounter information 102 and/or audio encounter information 106) to associate at least a second portion of the encounter information with at least a second encounter participant; and may assign 620 at least a second role to the at least a second encounter participant.

Specifically, automated clinical documentation process 10 may process 618 the encounter information (e.g., machine vision encounter information 102 and/or audio encounter information 106) to associate at least a second portion of the encounter information with at least a second encounter participant. For example, automated clinical documentation process 10 may process 618 the encounter information (e.g., machine vision encounter information 102 and/or audio encounter information 106) to associate audio encounter information 106B and machine vision encounter information 102B with encounter participant 228 and may associate audio encounter information 106C and machine vision encounter information 102C with encounter participant 230.

Further, automated clinical documentation process 10 may assign 620 at least a second role to the at least a second encounter participant. For example, automated clinical documentation process 10 may assign 620 a role to encounter participants 228, 230.

Automated clinical documentation process 10 may be configured to monitor multiple encounter participants (e.g., encounter participants 226, 228, 230) within a patient encounter (e.g., a visit to a doctor's office), wherein some of these encounter participants may be identifiable via a unique voice print/profile, while others may be unidentifiable due to a lack of a unique voice print/profile.

Figure 11:
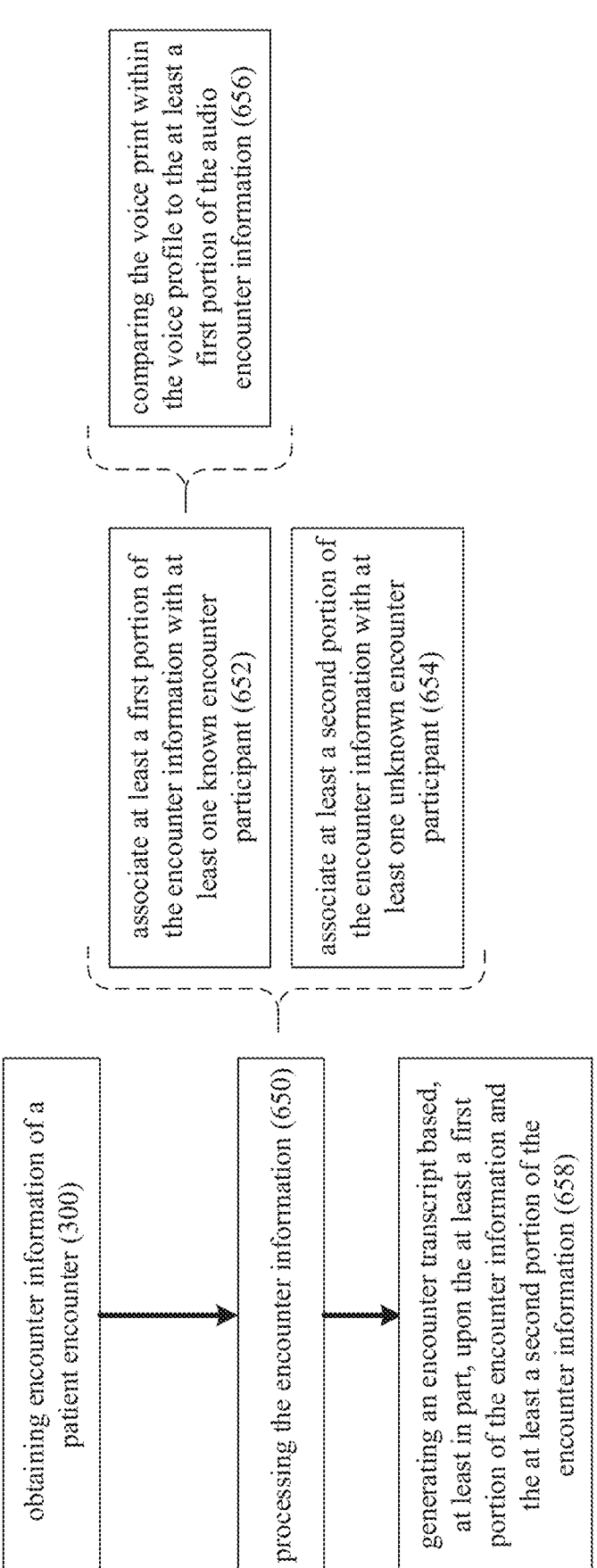
FIG. 11 is a flow chart of another implementation of the automated clinical documentation process of FIG. 1.

Accordingly and referring also to FIG. 11, automated clinical documentation process 10 may be configured to obtain 300 encounter information (e.g., machine vision encounter information 102 and/or audio encounter information 106) of a patient encounter (e.g., a visit to a doctor's office).

Automated clinical documentation process 10 may process 650 the encounter information (e.g., machine vision encounter information 102 and/or audio encounter information 106) to: associate 652 at least a first portion of the encounter information (e.g., machine vision encounter information 102 and/or audio encounter information 106) with at least one known encounter participant, and associate 654 at least a second portion of the encounter information (e.g., machine vision encounter information 102 and/or audio encounter information 106) with at least one unknown encounter participant.

As discussed above, modular ACD system 54 may be configured to form one or more audio recording beams (e.g., audio recording beams 220, 222, 224) via the discrete audio acquisition devices (e.g., discrete audio acquisition devices 202, 204, 206, 208, 210, 212, 214, 216, 218) included within audio recording system 104, wherein modular ACD system 54 may be further configured to steer the one or more audio recording beams (e.g., audio recording beams 220, 222, 224) toward one or more encounter participants (e.g., encounter participants 226, 228, 230) of the above-described patient encounter.

Accordingly and continuing with the above-stated example, modular ACD system 54 may steer audio recording beam 220 toward encounter participant 226, may steer audio recording beam 222 toward encounter participant 228, and may steer audio recording beam 224 toward encounter participant 230. Accordingly and due to the directionality of audio recording beams 220, 222, 224, audio encounter information 106 may include three components, namely audio encounter information 106A (which is obtained via audio recording beam 220), audio encounter information 106B (which is obtained via audio recording beam 222) and audio encounter information 106C (which is obtained via audio recording beam 220).

Further and as discussed above, ACD compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource.

When associating 652 at least a first portion of the encounter information (e.g., machine vision encounter information 102 and/or audio encounter information 106) with at least one known encounter participant, automated clinical documentation process 10 may compare 656 the data included within the user profile (defined within the user profile datasource) to the at least a first portion of the audio encounter information. The data included within the user profile may include voice-related data (e.g., a voice print that is defined locally within the user profile or remotely within the voice print datasource), language use patterns, user accent identifiers, user-defined macros, and user-defined shortcuts, for example.

Specifically and when attempting to associate 652 at least a first portion of the encounter information (e.g., machine vision encounter information 102 and/or audio encounter information 106) with at least one known encounter participant, automated clinical documentation process 10 may compare 656 one or more voice prints (defined within the voice print datasource) to one or more voices defined within the first portion of the audio encounter information (e.g., audio encounter information 106A); may compare 656 one or more voice prints (defined within the voice print datasource) to one or more voices defined within the second portion of the audio encounter information (e.g., audio encounter information 106B); and may compare 656 one or more voice prints (defined within the voice print datasource) to one or more voices defined within the third portion of the audio encounter information (e.g., audio encounter information 106C).

As discussed above and for this example, assume: that encounter participant 226 is a medical professional that has a voice print/profile; that encounter participant 228 is a long-term patient that has a voice print/profile; and that encounter participant 230 is a third party (the acquaintance of encounter participant 228) and, therefore, does not have a voice print/profile. Accordingly and for this example: assume that automated clinical documentation process 10 will be successful and identify encounter participant 226 when comparing 656 audio encounter information 106A to the various voice prints/profiles included within voice print datasource; assume that automated clinical documentation process 10 will be successful and identify encounter participant 228 when comparing 656 audio encounter information 106B to the various voice prints/profiles included within voice print datasource; and assume that automated clinical documentation process 10 will be unsuccessful and not identify encounter participant 230 when comparing 656 audio encounter information 106C to the various voice prints/profiles included within voice print datasource.

Accordingly and when processing 650 the encounter information (e.g., machine vision encounter information 102 and/or audio encounter information 106), automated clinical documentation process 10 may associate 652 audio encounter information 106A with the voice print/profile of Doctor Susan Jones and may identify encounter participant 226 as "Doctor Susan Jones". Automated clinical documentation process 10 may further associate 654 audio encounter information 106B with the voice print/profile of Patient Paul Smith and may identify encounter participant 228 as "Patient Paul Smith". Further, automated clinical documentation process 10 may not be able to associate 654 audio encounter information 106C with any voice prints/profiles and may identify encounter participant 230 as "Unknown Participant".

Automated clinical documentation process 10 may generate 658 an encounter transcript (e.g., encounter transcript 234) based, at least in part, upon the at least a first portion of the encounter information (e.g., machine vision encounter information 102 and/or audio encounter information 106) and the at least a second portion of the encounter information (e.g., machine vision encounter information 102 and/or audio encounter information 106). Accordingly, automated clinical documentation process 10 may generate 658 an encounter transcript (e.g., encounter transcript 234) that identifies the verbal comments and utterances made by "Doctor Susan Jones", "Patient Paul Smith" and "Unknown Participant".

Automated clinical documentation process 10 may be configured to use semantic frames as an intermediary step between encounter transcript 234 and medical record 236, wherein these semantic frames may define an abstract meaning of a portion of encounter transcript and this abstract meaning may be used when populating medical record 236.

Figure 12:
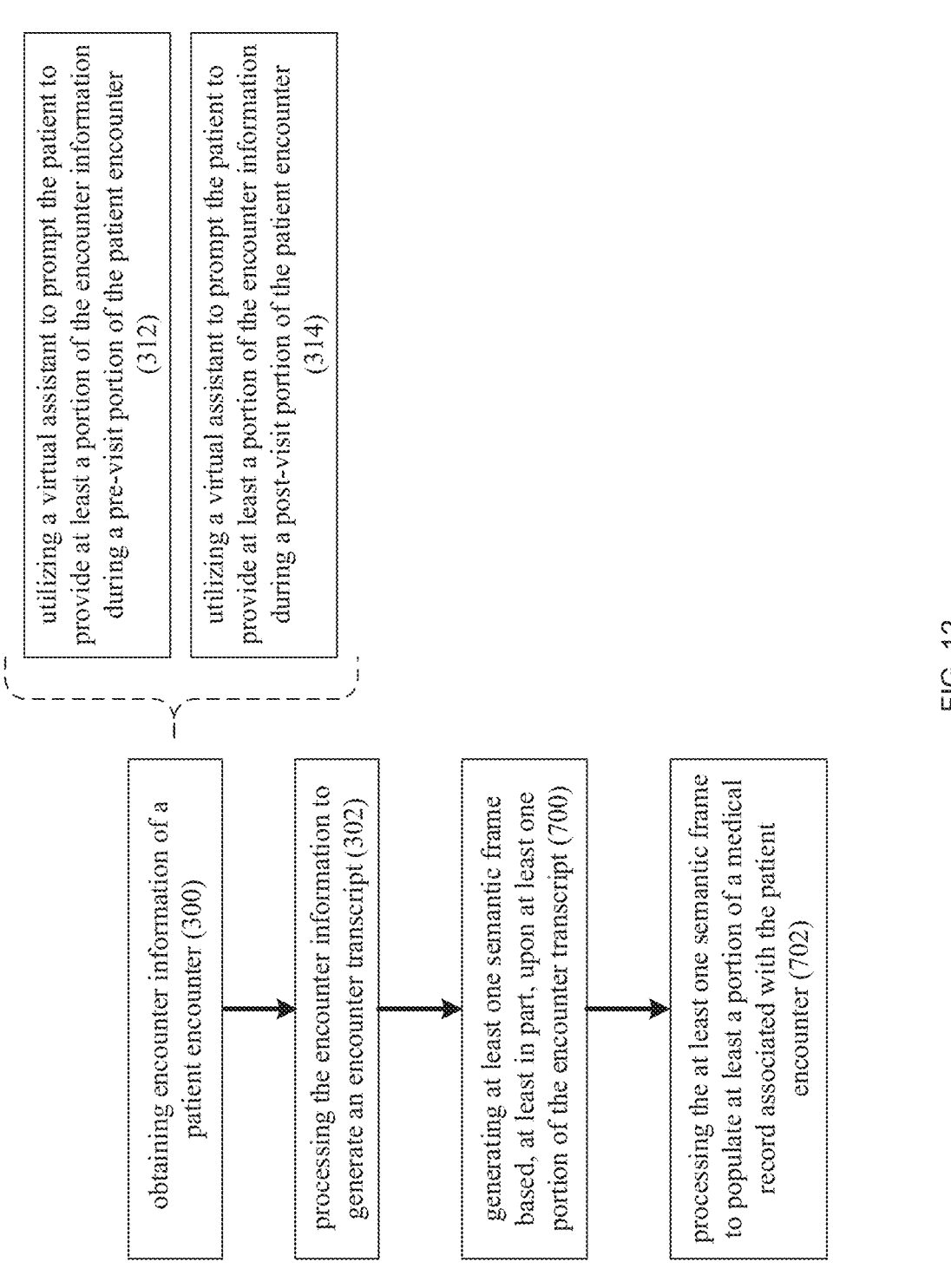
FIG. 12 is a flow chart of another implementation of the automated clinical documentation process of FIG. 1.
Figure 13A:
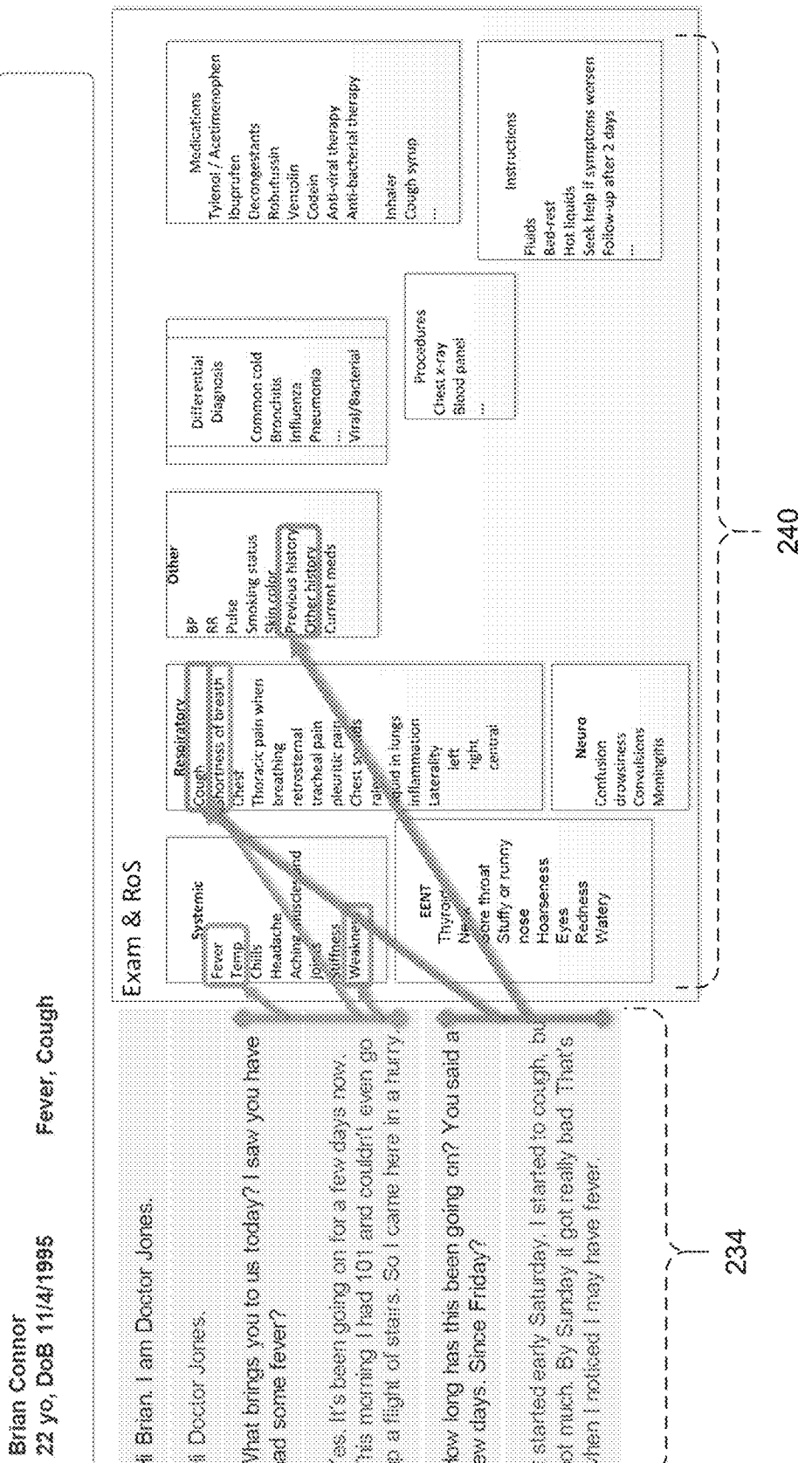
FIGS. 13A-13E are diagrammatic views of the encounter transcript and semantic frames as generated by the automated clinical documentation process of FIG. 1.
Figure 13B:
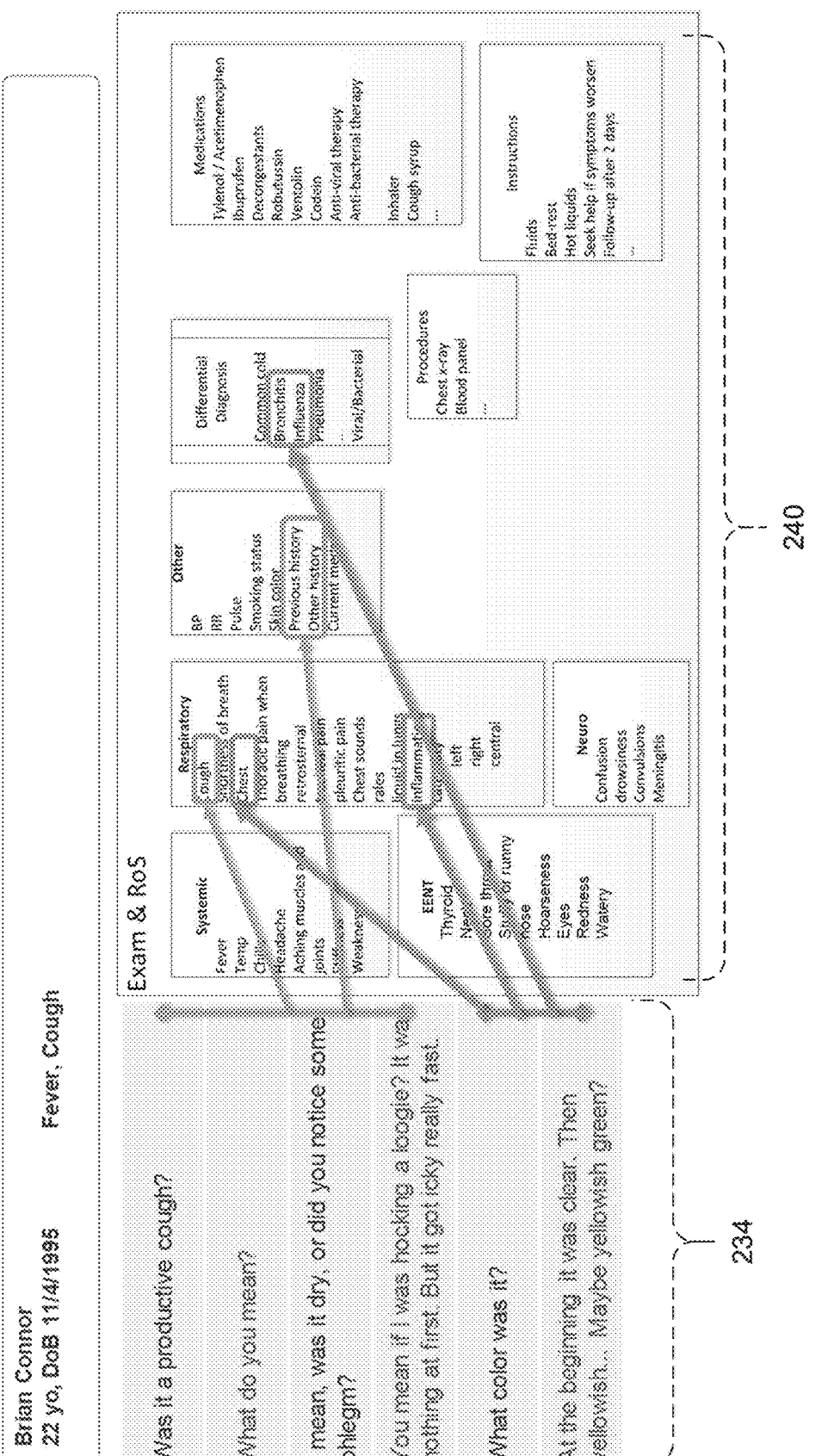
Figure 13C:
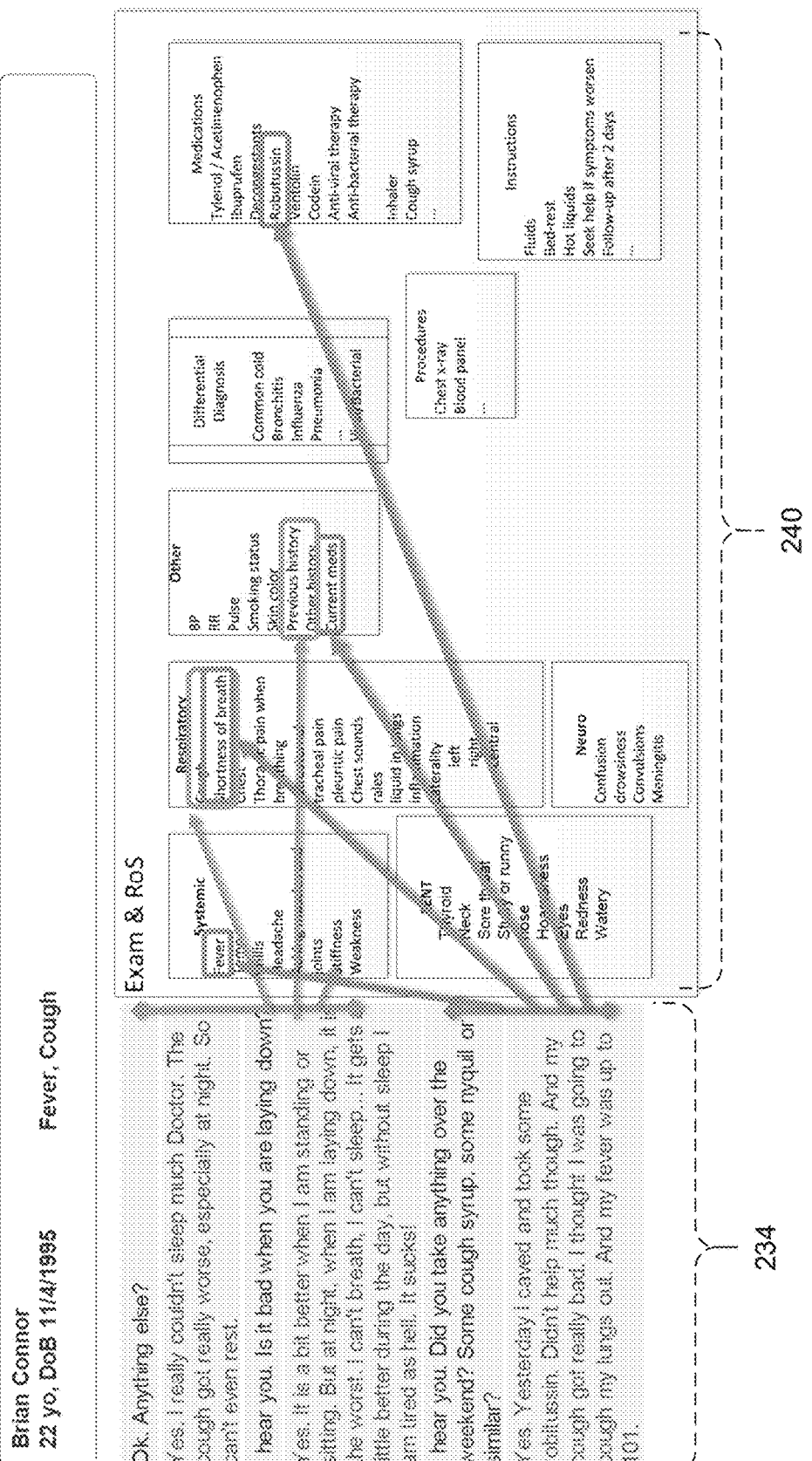
Figure 13D:
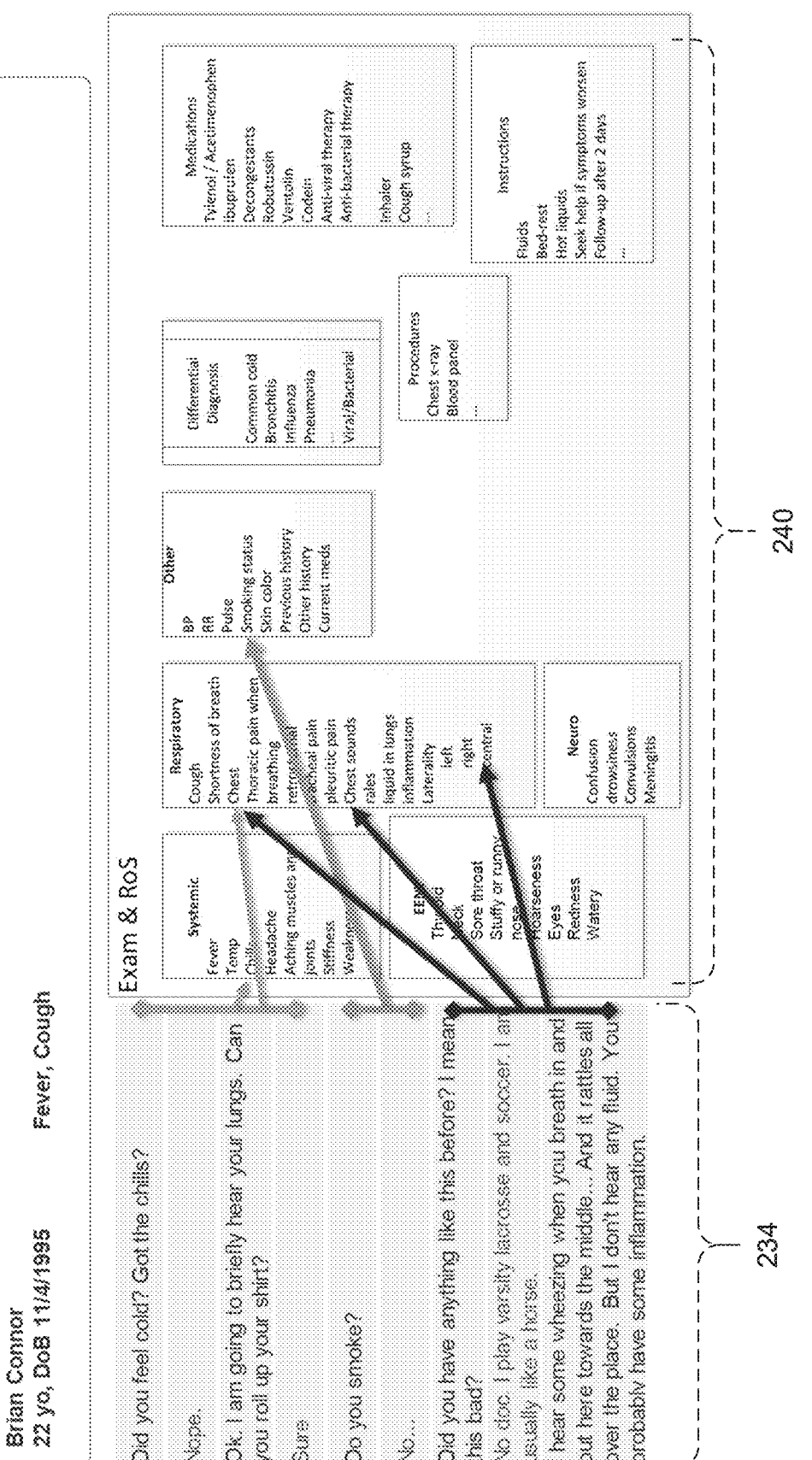
Figure 13E:
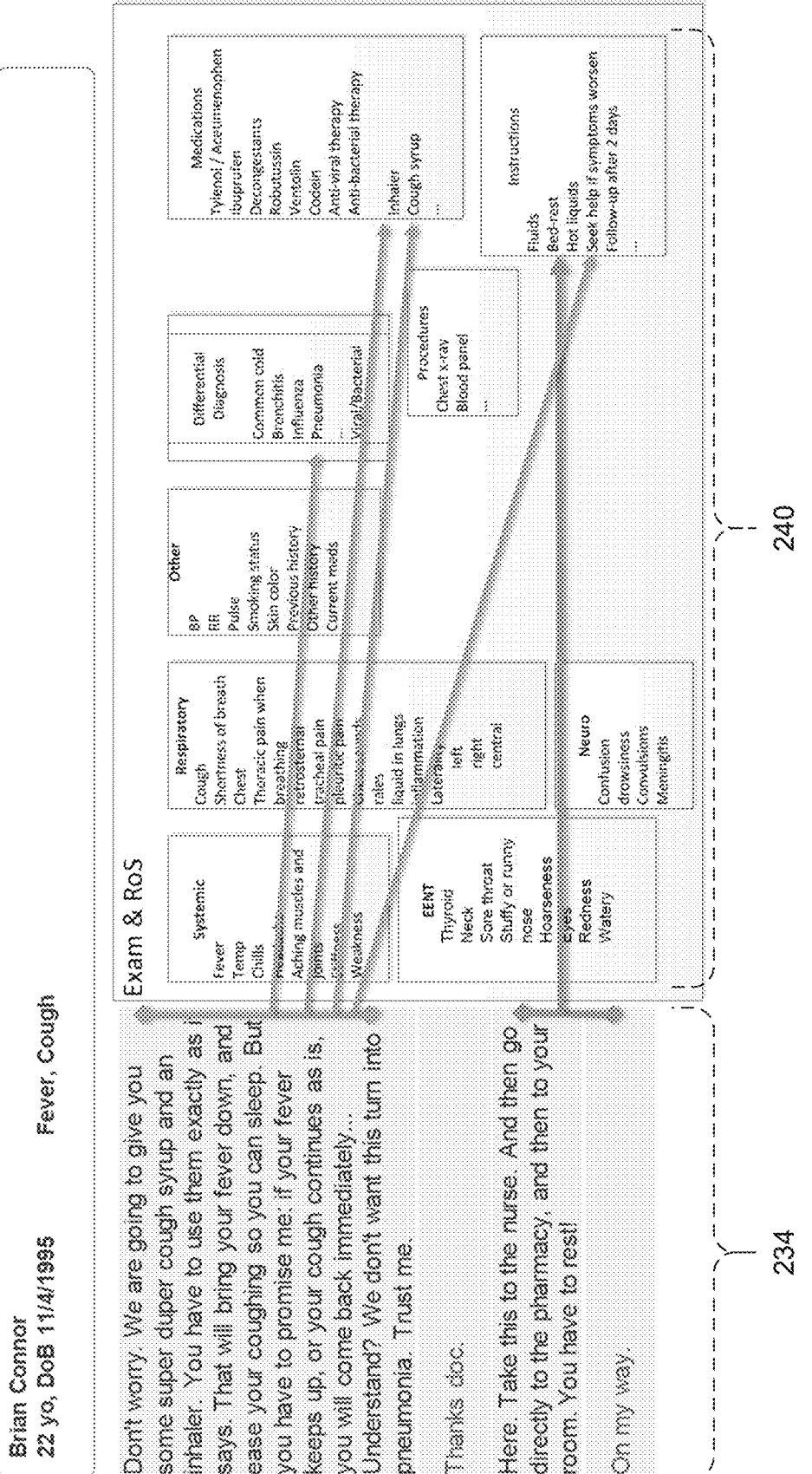

Accordingly and referring also to FIG. 12, automated clinical documentation process 10 may be configured to obtain 300 encounter information (e.g., machine vision encounter information 102 and/or audio encounter information 106) of a patient encounter (e.g., a visit to a doctor's office).

As discussed above, since machine vision system 100 and audio recording system 104 may be positioned throughout monitored space 130, all of the interactions between medical professionals (e.g., encounter participant 226), patients (e.g., encounter participant 228) and third parties (e.g., encounter participant 230) that occur during the patient encounter (e.g., encounter participant 228 visiting the doctor's office) within the monitored space (e.g., monitored space 130) of the clinical environment (e.g., the doctor's office) may be monitored/recorded/processed. Accordingly, a patient "check-in" area within monitored space 130 may be monitored to obtain encounter information (e.g., machine vision encounter information 102 and/or audio encounter information 106) during this pre-visit portion of the patient encounter (e.g., encounter participant 228 visiting the doctor's office). Additionally and as discussed above, this pre-visit encounter information may be obtained via e.g., virtual assistant 238 before the patient (e.g., encounter participant 228) has entered monitored space 130. Further, various rooms within monitored space 130 may be monitored to obtain encounter information (e.g., machine vision encounter information 102 and/or audio encounter information 106) during these various portions of the patient encounter (e.g., while meeting with the doctor, while vital signs and statistics are obtained, and while imaging is performed). Further, a patient "check-out" area within monitored space 130 may be monitored to obtain encounter information (e.g., machine vision encounter information 102 and/or audio encounter information 106) during this post-visit portion of the patient encounter (e.g., encounter participant 228 visiting the doctor's office). Additionally and as discussed above, this post-visit encounter information may be obtained via e.g., virtual assistant 238 after the patient (e.g., encounter participant 228) has left monitored space 130. Further and via machine vision encounter information 102, visual speech recognition (via visual lip-reading functionality) may be utilized by automated clinical documentation process 10 to further effectuate the gathering of audio encounter information 106.

Accordingly, a complete recording of the patient encounter (e.g., encounter participant 228 visiting the doctor's office) may be generated, wherein this encounter information (e.g., machine vision encounter information 102 and/or audio encounter information 106) may be processed 302 to generate an encounter transcript (e.g., encounter transcript 234).

As is known in the art, a semantic frame (e.g., semantic frame 240) may be a collection of facts that specify "characteristic features, attributes, and functions of a denotatum, and its characteristic interactions with things necessarily or typically associated with it." Accordingly, a semantic frame (e.g., semantic frame 240) may be defined as a coherent structure of related concepts that are related such that without knowledge of all of the related concepts, one does not have complete knowledge of any of the related concepts. Further, a semantic frame (e.g., semantic frame 240) may be based on recurring experiences, wherein e.g., a commercial transaction semantic frame may be based upon recurring experiences in the commercial transactions space. Accordingly, a semantic frame (e.g., semantic frame 240) may define an abstract meaning of a portion of an encounter transcript.

Accordingly, automated clinical documentation process 10 may generate 700 at least one semantic frame (e.g., semantic frame 240) based, at least in part, upon at least one portion of encounter transcript 234, wherein the at least one semantic frame (e.g., semantic frame 240) may define an abstract meaning for the at least one portion of encounter transcript 234.

Referring also to FIGS. 13A-13E, there are shown various illustrative examples concerning the manner in which automated clinical documentation process 10 may generate 700 at least one semantic frame (e.g., semantic frame 240) based, at least in part, upon at least one portion of encounter transcript 234, Specifically and as shown in these figures, various discrete portions of encounter transcript 234 may be mapped onto the various semantic frames.

Automated clinical documentation process 10 may then process 702 the at least one semantic frame (e.g., semantic frame 240) to populate at least a portion of a medical record (e.g., medical record 236) associated with the patient encounter (e.g., a visit to a doctor's office).

Referring also to FIGS. 14A-14B, there are shown various illustrative examples concerning the manner in which automated clinical documentation process 10 may process 702 the at least one semantic frame (e.g., semantic frame 240) to populate at least a portion of a medical record (e.g., medical record 236). Specifically and as shown in these figures, various discrete pieces of data defined within the various semantic frames (e.g., semantic frame 240) may be used to populate medical record 236.

As discussed above, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office).

Accordingly and when obtaining 300 encounter information (e.g., machine vision encounter information 102 and/or audio encounter information 106), automated clinical documentation process 10 may utilize 312 a virtual assistant (e.g., virtual assistant 238) to prompt the patient to provide at least a portion of the encounter information (e.g., machine vision encounter information 102 and/or audio encounter information 106) during a pre-visit portion of the patient encounter (e.g., a visit to a doctor's office).

Further and when obtaining 300 encounter information (e.g., machine vision encounter information 102 and/or audio encounter information 106), automated clinical documentation process 10 may utilize 314 a virtual assistant (e.g., virtual assistant 238) to prompt the patient to provide at least a portion of the encounter information (e.g., machine vision encounter information 102 and/or audio encounter information 106) during a post-visit portion of the patient encounter (e.g., a visit to a doctor's office).

Automated clinical documentation process 10 may be configured to track the movement and/or interaction of humanoid shapes within the monitored space (e.g., monitored space 130) during the patient encounter (e.g., a visit to a doctor's office) so that e.g., the automated clinical documentation process 10 knows when encounter participants (e.g., one or more of encounter participants 226, 228, 230) enter, exit or cross paths within monitored space 130.

Figure 15:
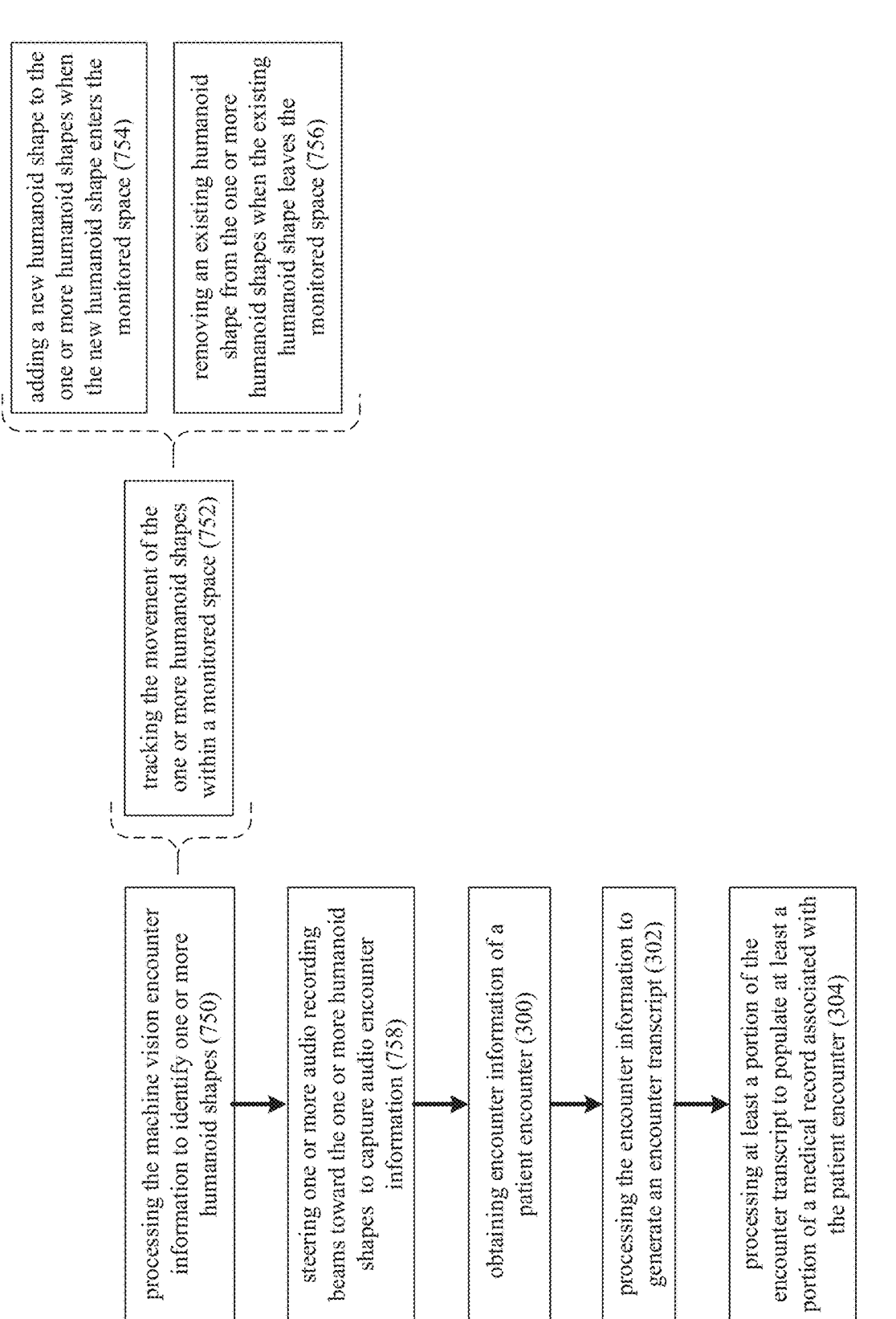
FIG. 15 is a flow chart of another implementation of the automated clinical documentation process of FIG. 1.

Accordingly and referring also to FIG. 15, automated clinical documentation process 10 may process 750 the machine vision encounter information (e.g., machine vision encounter information 102) to identify one or more humanoid shapes. As discussed above, examples of machine vision system 100 generally (and ACD client electronic device 34 specifically) may include but are not limited to one or more of an RGB imaging system, an infrared imaging system, an ultraviolet imaging system, a laser imaging system, a SONAR imaging system, a RADAR imaging system, and a thermal imaging system).

When ACD client electronic device 34 includes a visible light imaging system (e.g., an RGB imaging system), ACD client electronic device 34 may be configured to monitor various objects within monitored space 130 by recording motion video in the visible light spectrum of these various objects. When ACD client electronic device 34 includes an invisible light imaging systems (e.g., a laser imaging system, an infrared imaging system and/or an ultraviolet imaging system), ACD client electronic device 34 may be configured to monitor various objects within monitored space 130 by recording motion video in the invisible light spectrum of these various objects. When ACD client electronic device 34 includes an X-ray imaging system, ACD client electronic device 34 may be configured to monitor various objects within monitored space 130 by recording energy in the X-ray spectrum of these various objects. When ACD client electronic device 34 includes a SONAR imaging system, ACD client electronic device 34 may be configured to monitor various objects within monitored space 130 by transmitting soundwaves that may be reflected off of these various objects. When ACD client electronic device 34 includes a RADAR imaging system, ACD client electronic device 34 may be configured to monitor various objects within monitored space 130 by transmitting radio waves that may be reflected off of these various objects. When ACD client electronic device 34 includes a thermal imaging system, ACD client electronic device 34 may be configured to monitor various objects within monitored space 130 by tracking the thermal energy of these various objects.

As discussed above, ACD compute system 12 may be configured to access one or more datasources 118 (e.g., plurality of individual datasources 120, 122, 124, 126, 128), wherein examples of which may include but are not limited to one or more of a user profile datasource, a voice print datasource, a voice characteristics datasource (e.g., for adapting the automated speech recognition models), a face print datasource, a humanoid shape datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource.

Accordingly and when processing 750 the machine vision encounter information (e.g., machine vision encounter information 102) to identify one or more humanoid shapes, automated clinical documentation process 10 may be configured to compare the humanoid shapes defined within one or more datasources 118 to potential humanoid shapes within the machine vision encounter information (e.g., machine vision encounter information 102).

When processing 750 the machine vision encounter information (e.g., machine vision encounter information 102) to identify one or more humanoid shapes, automated clinical documentation process 10 may track 752 the movement of the one or more humanoid shapes within the monitored space (e.g., monitored space 130). For example and when tracking 752 the movement of the one or more humanoid shapes within monitored space 130, automated clinical documentation process 10 may add 754 a new humanoid shape to the one or more humanoid shapes when the new humanoid shape enters the monitored space (e.g., monitored space 130) and/or may remove 756 an existing humanoid shape from the one or more humanoid shapes when the existing humanoid shape leaves the monitored space (e.g., monitored space 130).

For example, assume that a lab technician (e.g., encounter participant 242) temporarily enters monitored space 130 to chat with encounter participant 230. Accordingly, automated clinical documentation process 10 may add 754 encounter participant 242 to the one or more humanoid shapes being tracked 752 when the new humanoid shape (i.e., encounter participant 242) enters monitored space 130. Further, assume that the lab technician (e.g., encounter participant 242) leaves monitored space 130 after chatting with encounter participant 230. Therefore, automated clinical documentation process 10 may remove 756 encounter participant 242 from the one or more humanoid shapes being tracked 752 when the humanoid shape (i.e., encounter participant 242) leaves monitored space 130.

Also and when tracking 752 the movement of the one or more humanoid shapes within monitored space 130, automated clinical documentation process 10 may monitor the trajectories of the various humanoid shapes within monitored space 130. Accordingly, assume that when leaving monitored space 130, encounter participant 242 walks in front of (or behind) encounter participant 226. As automated clinical documentation process 10 is monitoring the trajectories of (in this example) encounter participant 242 (who is e.g., moving from left to right) and encounter participant 226 (who is e.g., stationary), when encounter participant 242 passes in front of (or behind) encounter participant 226, the identities of these two humanoid shapes may not be confused by automated clinical documentation process 10.

Automated clinical documentation process 10 may be configured to obtain 300 the encounter information of the patient encounter (e.g., a visit to a doctor's office), which may include machine vision encounter information 102 (in the manner described above) and/or audio encounter information 106.

Automated clinical documentation process 10 may steer 758 one or more audio recording beams (e.g., audio recording beams 220, 222, 224) toward the one or more humanoid shapes (e.g., encounter participants 226, 228, 230) to capture audio encounter information (e.g., audio encounter information 106), wherein audio encounter information 106 may be included within the encounter information (e.g., machine vision encounter information 102 and/or audio encounter information 106).

Specifically, automated clinical documentation process 10 (via modular ACD system 54 and/or audio recording system 104) may utilize one or more of the discrete audio acquisition devices (e.g., audio acquisition devices 202, 204, 206, 208, 210, 212, 214, 216, 218) to form an audio recording beam. For example, automated clinical documentation process 10 may utilize audio acquisition device 210 to form audio recording beam 220, thus enabling the capturing of audio (e.g., speech) produced by encounter participant 226 (as audio acquisition device 210 is pointed to (i.e., directed toward) encounter participant 226). Additionally, automated clinical documentation process 10 may utilize audio acquisition devices 204, 206 to form audio recording beam 222, thus enabling the capturing of audio (e.g., speech) produced by encounter participant 228 (as audio acquisition devices 204, 206 are pointed to (i.e., directed toward) encounter participant 228). Additionally, automated clinical documentation process 10 may utilize audio acquisition devices 212, 214 to form audio recording beam 224, thus enabling the capturing of audio (e.g., speech) produced by encounter participant 230 (as audio acquisition devices 212, 214 are pointed to (i.e., directed toward) encounter participant 230).

Once obtained, automated clinical documentation process 10 may process 302 the encounter information (e.g., machine vision encounter information 102 and/or audio encounter information 106) to generate encounter transcript 234 and may process 304 at least a portion of encounter transcript 234 to populate at least a portion of a medical record (e.g., medical record 236) associated with the patient encounter (e.g., a visit to a doctor's office).

Automated clinical documentation process 10 may be configured to filter out audio that does not belong within audio recording beams (e.g., audio recording beams 220, 222, 224) using e.g., echo cancellation and/or blind source processing.

Figure 16:
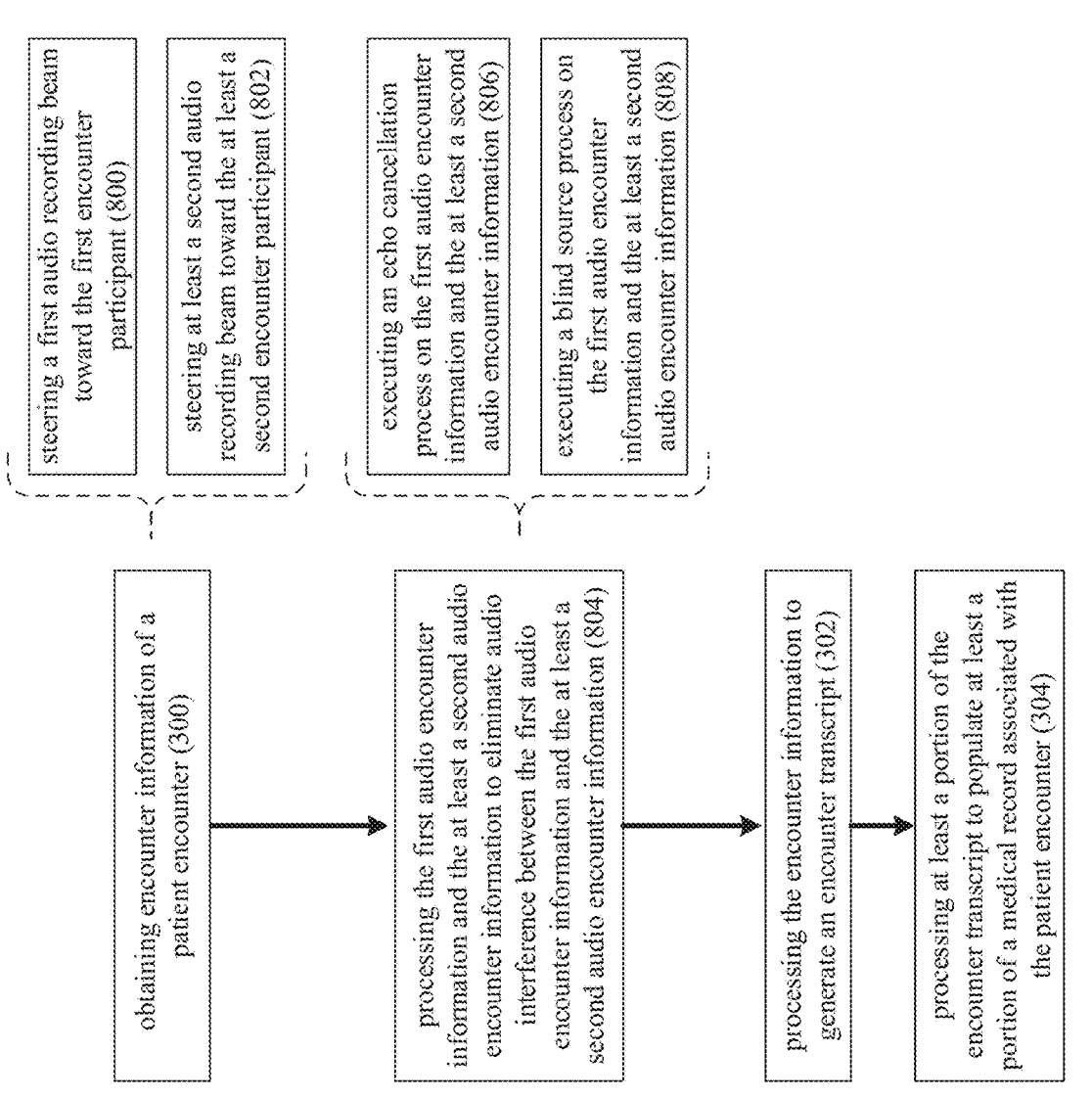
FIG. 16 is a flow chart of another implementation of the automated clinical documentation process of FIG. 1.

Accordingly and referring also to FIG. 16, automated clinical documentation process 10 may be configured to obtain 300 encounter information (e.g., machine vision encounter information 102 and/or audio encounter information 106) of a patient encounter (e.g., a visit to a doctor's office), wherein the encounter information (e.g., machine vision encounter information 102 and/or audio encounter information 106) includes first audio encounter information obtained from a first encounter participant and at least a second audio encounter information obtained from at least a second encounter participant.

When obtaining 300 encounter information (e.g., machine vision encounter information 102 and/or audio encounter information 106) of a patient encounter (e.g., a visit to a doctor's office), automated clinical documentation process 10 may steer 800 a first audio recording beam toward the first encounter participant; and may steer 802 at least a second audio recording beam toward the at least a second encounter participant.

Specifically, automated clinical documentation process 10 (via modular ACD system 54 and/or audio recording system 104) may utilize one or more of the discrete audio acquisition devices (e.g., audio acquisition devices 202, 204, 206, 208, 210, 212, 214, 216, 218) to form an audio recording beam. For example, automated clinical documentation process 10 may utilize audio acquisition device 210 to form audio recording beam 220, thus enabling the capturing of audio (e.g., speech) produced by encounter participant 226 (as audio acquisition device 210 is pointed to (i.e., directed toward) encounter participant 226). Additionally, automated clinical documentation process 10 may utilize audio acquisition devices 204, 206 to form audio recording beam 222, thus enabling the capturing of audio (e.g., speech) produced by encounter participant 228 (as audio acquisition devices 204, 206 are pointed to (i.e., directed toward) encounter participant 228). Additionally, automated clinical documentation process 10 may utilize audio acquisition devices 212, 214 to form audio recording beam 224, thus enabling the capturing of audio (e.g., speech) produced by encounter participant 230 (as audio acquisition devices 212, 214 are pointed to (i.e., directed toward) encounter participant 230).

As there is a comparatively narrow angle of separation between audio recording beam 220 and audio recording beam 224, automated clinical documentation process 10 may process 804 the first audio encounter information (e.g., audio encounter information 106A from encounter participant 226) and the at least a second audio encounter information (e.g., audio encounter information 106C from encounter participant 230) to eliminate audio interference between the first audio encounter information (e.g., audio encounter information 106A) and the at least a second audio encounter information (e.g., audio encounter information 106C).

One example of such audio interference between the first audio encounter information (e.g., audio encounter information 106A) and the at least a second audio encounter information (e.g., audio encounter information 106C) may include but is not limited to crosstalk between the first audio encounter information (e.g., audio encounter information 106A) and the at least a second audio encounter information (e.g., audio encounter information 106C). As is known in the art, crosstalk may occur when two or more people are speaking simultaneously when e.g., speakers are interrupting each other or during what may be referred to as "active listening" (i.e., basically indicating attention and comprehension with a lot of utterances of e.g., "yes", "got it" and "hmm". Other common sounds (e.g., heavy breathing and deep breathing) by the patient may also impact automated clinical documentation process 10 and may need to be filtered out.

When processing 804 the first audio encounter information (e.g., audio encounter information 106A) and the at least a second audio encounter information (e.g., audio encounter information 106C) to eliminate audio interference, automated clinical documentation process 10 may execute 806 an echo cancellation process on the first audio encounter information (e.g., audio encounter information 106A) and the at least a second audio encounter information (e.g., audio encounter information 106C).

As is known in the art, echo cancellation is a method for improving signal quality by removing echo after it is already present. This method may be called acoustic echo suppression (AES) and acoustic echo cancellation (AEC), and more rarely line echo cancellation (LEC). In some cases, these terms are more precise, as there are various types and causes of echo with unique characteristics, including acoustic echo (sounds from a loudspeaker being reflected and recorded by a microphone, which can vary substantially over time) and line echo (electrical impulses caused by e.g., coupling between the sending and receiving wires, impedance mismatches, electrical reflections, etc., which varies much less than acoustic echo). Accordingly and in this configurations, such echo cancellation methodologies may be utilized to e.g., eliminate the echo of a second speaker that appears in the audio recording beam steered at a closely-positioned first speaker; while also eliminating the echo of the first speaker that appears in the audio recording beam steered at the closely-positioned second speaker.

When processing 804 the first audio encounter information (e.g., audio encounter information 106A) and the at least a second audio encounter information (e.g., audio encounter information 106C) to eliminate audio interference, automated clinical documentation process 10 may execute 808 a blind source separation process on the first audio encounter information (e.g., audio encounter information 106A) and the at least a second audio encounter information (e.g., audio encounter information 106C).

As is known in the art, blind source separation is the separation of a set of source signals from a set of mixed signals, without the aid of information (or with very little information) about the source signals or the mixing process. This problem is in general highly underdetermined but useful solutions can be derived under a surprising variety of conditions. Much of the early literature in this field focuses on the separation of temporal signals such as audio. However, blind source separation is now routinely performed on multidimensional data, such as images and tensors that may involve no time dimension whatsoever. Since the chief difficulty of the problem is its underdetermination, methods for blind source separation generally seek to narrow the set of possible solutions in a way that is unlikely to exclude the desired solution. In one approach, exemplified by principal and independent component analysis, one seeks source signals that are minimally correlated or maximally independent in a probabilistic or information-theoretic sense. A second approach, exemplified by nonnegative matrix factorization, is to impose structural constraints on the source signals. These structural constraints may be derived from a generative model of the signal, but are more commonly heuristics justified by good empirical performance. A common theme in the second approach is to impose some kind of low-complexity constraint on the signal, such as sparsity in some basis for the signal space. This approach can be particularly effective if one requires not the whole signal, but merely its most salient features.

As discussed above, modular ACD system 54 and/or audio recording system 104 may be configured to utilize null-steering precoding to cancel interference between speakers and/or noise.

Once processed 804, automated clinical documentation process 10 may process 302 the encounter information (e.g., machine vision encounter information 102 and/or audio encounter information 106) to generate encounter transcript 234 and may process 304 at least a portion of encounter transcript 234 to populate at least a portion of a medical record (e.g., medical record 236) associated with the patient encounter (e.g., a visit to a doctor's office).

Figure 17:
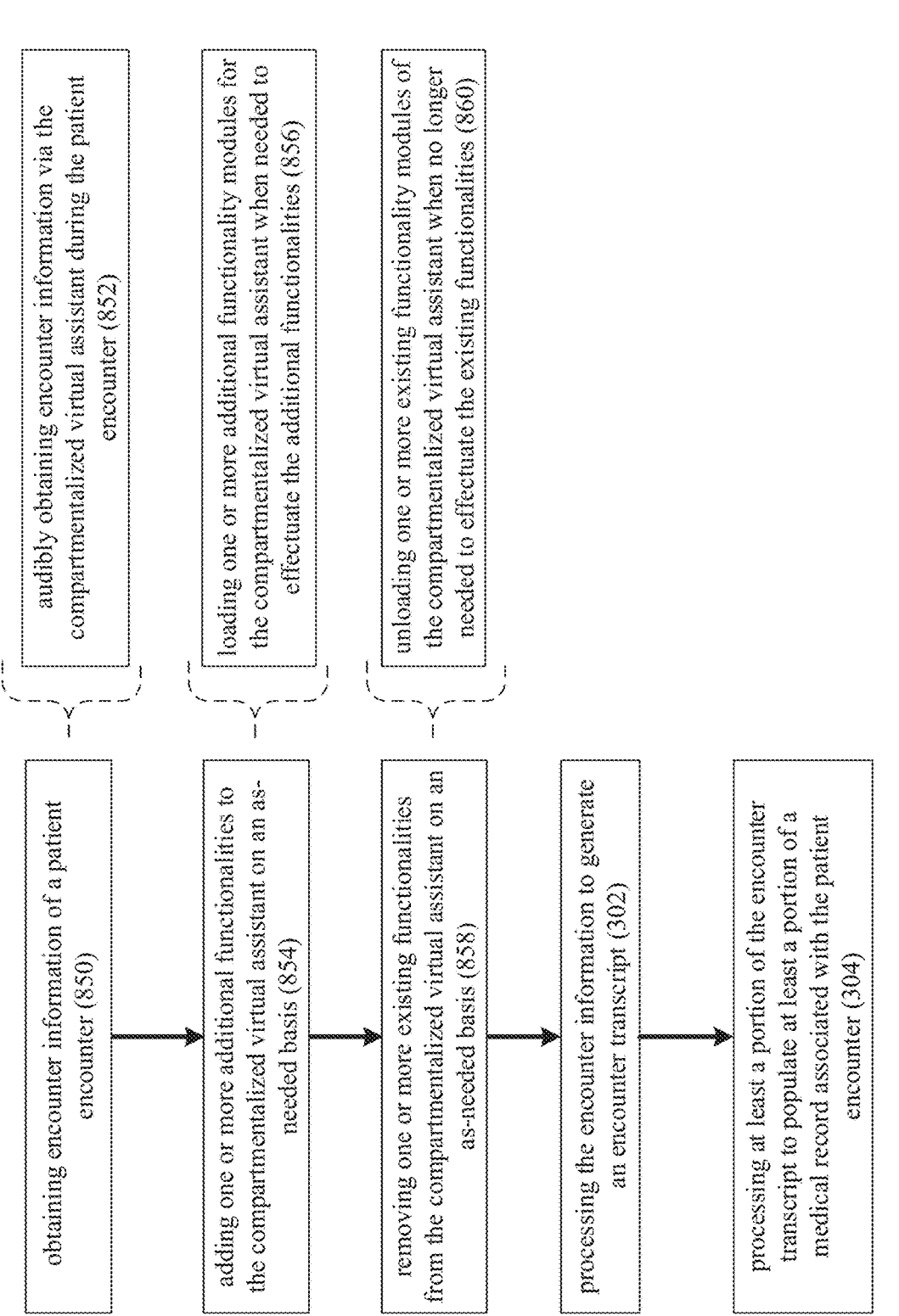
FIG. 17 is a flow chart of another implementation of the automated clinical documentation process of FIG. 1.

Automated clinical documentation process 10 may be configured to include a virtual assistant (e.g., virtual assistant 238) that is modular in design. While this virtual assistant (e.g., virtual assistant 238) may include only one persona (e.g., Nuance's Florence) for interacting with users, this virtual assistant (e.g., virtual assistant 238) may include various functionality modules that may be configured to run in parallel with each other and be added to (or removed from) the virtual assistant (e.g., virtual assistant 238) as needed Accordingly and referring also to FIG. 17, automated clinical documentation process 10 may be configured to obtain 850 encounter information (e.g., machine vision encounter information 102 and/or audio encounter information 106) via a compartmentalized virtual assistant (e.g., virtual assistant 238) during a patient encounter (e.g., a visit to a doctor's office), wherein the compartmentalized virtual assistant (e.g., virtual assistant 238) may include a core functionality module (e.g., core functionality module 244). An example of core functionality module 244 may include but is not limited to a functionality module that verbally interacts with an encounter participant (e.g., encounter participant 228) of the patient encounter (e.g., a visit to a doctor's office).

As discussed above, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office). For example and during a pre-visit portion of the patient encounter (e.g., a visit to a doctor's office), the patient may be directed to a patient "check-in" area within monitored space 130, wherein the compartmentalized virtual assistant (e.g., virtual assistant 238) may verbally interact with the encounter participant (e.g., encounter participant 228). Accordingly and within this "check-in" area, automated clinical documentation process 10 may audibly obtain 852 encounter information (e.g., machine vision encounter information 102 and/or audio encounter information 106) via the compartmentalized virtual assistant (e.g., virtual assistant 238).

The compartmentalized virtual assistant (e.g., virtual assistant 238) may be configured to perform various different types of functionality during the patient encounter (e.g., a visit to a doctor's office). For example and during one portion of the patient encounter (e.g., a visit to a doctor's office), the compartmentalized virtual assistant (e.g., virtual assistant 238) may require functionality to interact with a medical insurance coverage datasource to determine whether a particular medication/medical procedure that was mentioned during a patient encounter (e.g., a visit to a doctor's office) is covered by the medical insurance plan of the patient. However, during other portions of the patient encounter (e.g., a visit to a doctor's office), such functionality may not be needed. Further and during other patient encounters, such functionality may not be needed at all.

Accordingly, automated clinical documentation process 10 may be configured to add 854 one or more additional functionalities to the compartmentalized virtual assistant (e.g., virtual assistant 238) on an as-needed basis. Accordingly and if during the patient encounter (e.g., a visit to a doctor's office), a certain functionality is needed, the appropriate functionality module (e.g., functionality module 246) may be added 854 by automated clinical documentation process 10. When adding 854 one or more additional functionalities to the compartmentalized virtual assistant (e.g., virtual assistant 238) on an as-needed basis, automated clinical documentation process 10 may load 856 one or more additional functionality modules (e.g., functionality module 246) for the compartmentalized virtual assistant (e.g., virtual assistant 238) when needed to effectuate the additional functionalities. Accordingly and by only loading 856 functionality modules (e.g., functionality module 246) on an as-needed basis, modular ACD system 54 will not be unduly loaded, thus efficiently utilizing the system resources (e.g., memory resources, compute resources, network resources, etc.) of modular ACD system 54.

Further, automated clinical documentation process 10 may be configured to remove 858 one or more existing functionalities from the compartmentalized virtual assistant (e.g., virtual assistant 238) on an as-needed basis. Accordingly and when, during the patient encounter (e.g., a visit to a doctor's office) a certain functionality is no longer needed, the appropriate functionality module (e.g., functionality module 248) may be removed 858 by automated clinical documentation process 10. When removing 858 one or more existing functionalities from the compartmentalized virtual assistant (e.g., virtual assistant 238) on an as-needed basis, automated clinical documentation process 10 may unload 860 one or more existing functionality modules (e.g., functionality module 248) of the compartmentalized virtual assistant (e.g., virtual assistant 238) when no longer needed to effectuate the existing functionalities. Accordingly and by unloading 860 functionality modules (e.g., functionality module 248) on an as-needed basis, modular ACD system 54 will not be unduly loaded, thus efficiently utilizing the system resources (e.g., memory resources, compute resources, network resources, etc.) of modular ACD system 54.

Once obtained 850, automated clinical documentation process 10 may process 302 the encounter information (e.g., machine vision encounter information 102 and/or audio encounter information 106) to generate encounter transcript 234 and may process 304 at least a portion of encounter transcript 234 to populate at least a portion of a medical record (e.g., medical record 236) associated with the patient encounter (e.g., a visit to a doctor's office).

Automated clinical documentation process 10 may be configured to allow for direct interaction of various functionality modules (e.g., functionality modules 244, 246, 248) of the compartmentalized virtual assistant (e.g., virtual assistant 238), thus not requiring hub & spoke interaction of these functionality modules.

Figure 18:
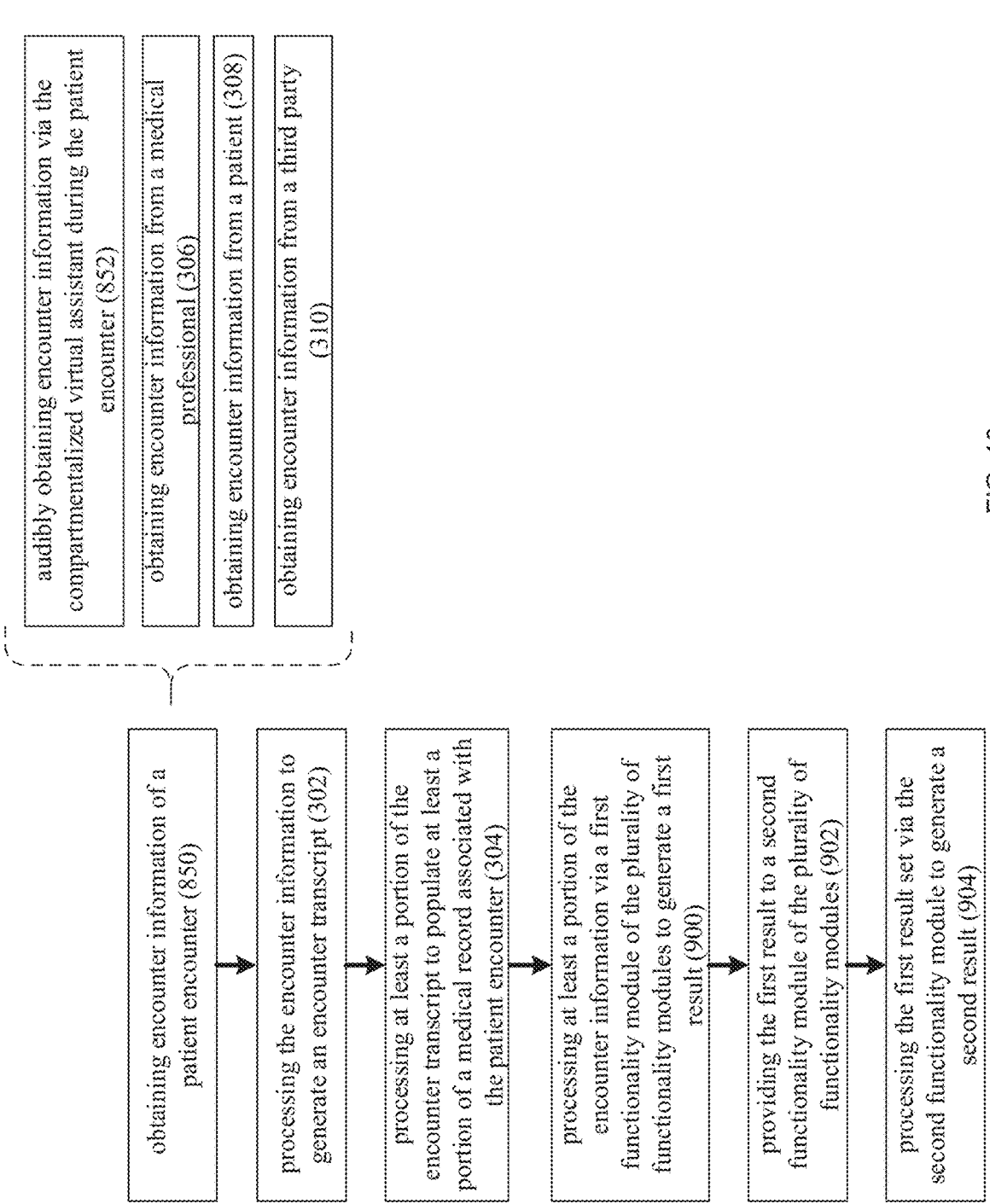
FIG. 18 is a flow chart of another implementation of the automated clinical documentation process of FIG. 1.

Accordingly and referring also to FIG. 18, automated clinical documentation process 10 may be configured to obtain 850 encounter information (e.g., machine vision encounter information 102 and/or audio encounter information 106) via the compartmentalized virtual assistant (e.g., virtual assistant 238) during a patient encounter (e.g., a visit to a doctor's office), wherein the compartmentalized virtual assistant (e.g., virtual assistant 238) may include a plurality of functionality modules (e.g., functionality modules 244, 246, 248).

As discussed above, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office). For example and during a pre-visit portion of the patient encounter (e.g., a visit to a doctor's office), the patient may be directed to a patient "check-in" area within monitored space 130, wherein the compartmentalized virtual assistant (e.g., virtual assistant 238) may verbally interact with the encounter participant (e.g., encounter participant 228). Accordingly and within this "check-in" area, automated clinical documentation process 10 may audibly obtain 852 encounter information (e.g., machine vision encounter information 102 and/or audio encounter information 106) via the compartmentalized virtual assistant (e.g., virtual assistant 238).

When obtaining 850 encounter information (e.g., machine vision encounter information 102 and/or audio encounter information 106), automated clinical documentation process 10 may: obtain 306 encounter information (e.g., machine vision encounter information 102 and/or audio encounter information 106) from a medical professional; obtain 308 encounter information (e.g., machine vision encounter information 102 and/or audio encounter information 106) from a patient; and obtain 310 encounter information (e.g., machine vision encounter information 102 and/or audio encounter information 106) from a third party. Further and when obtaining 300 encounter information (e.g., machine vision encounter information 102 and/or audio encounter information 106), automated clinical documentation process 10 may obtain 300 the encounter information (e.g., machine vision encounter information 102 and/or audio encounter information 106) from previous (related or unrelated) patient encounters. For example, if the current patient encounter is actually the third visit that the patient is making concerning e.g., shortness of breath, the encounter information from the previous two visits (i.e., the previous two patient encounters) may be highly-related and may be obtained 300 by automated clinical documentation process 10.

Once obtained 850, automated clinical documentation process 10 may process 302 the encounter information (e.g., machine vision encounter information 102 and/or audio encounter information 106) to generate encounter transcript 234 and may process 304 at least a portion of encounter transcript 234 to populate at least a portion of a medical record (e.g., medical record 236) associated with the patient encounter (e.g., a visit to a doctor's office).

As will be discussed below in greater detail, automated clinical documentation process 10 may process 900 at least a portion of the encounter information (e.g., machine vision encounter information 102 and/or audio encounter information 106) via a first functionality module (e.g., functionality module 246) of the plurality of functionality modules (e.g., functionality modules 244, 246, 248) to generate a first result (e.g., result set 250). Automated clinical documentation process 10 may provide 902 the first result (e.g., result set 250) to a second functionality module (e.g., functionality module 244) of the plurality of functionality modules (e.g., functionality modules 244, 246, 248). Automated clinical documentation process 10 may then process 904 the first result (e.g., result set 250) via the second functionality module (e.g., functionality module 244) to generate a second result (e.g., result set 252), which may be provided to a third functionality module (e.g., functionality module 248) of the plurality of functionality modules (e.g., functionality modules 244, 246, 248) for processing.

As discussed above, automated clinical documentation process 10 may be configured to include a virtual assistant (e.g., virtual assistant 238) that is modular in design. So while this virtual assistant (e.g., virtual assistant 238) may include only one persona (e.g., Nuance's Florence) for interacting with users, this virtual assistant (e.g., virtual assistant 238) may include various functionality modules (e.g., functionality modules 244, 246, 248) that may be configured to run in parallel with each other and effectuate different functionalities.

Accordingly, assume for this example that encounter participant 226 is going to prescribe an RA medication to encounter participant 228. Accordingly, the first functionality module (e.g., functionality module 246) may be an insurance functionality module that is configured to process 900 this portion of the encounter information and interface with a medical insurance provider of encounter participant 228 to obtain a list of covered RA medications (e.g., first result 250). Functionality module 246 may then provide 902 first result 250 to the second functionality module (e.g., functionality module 244), which may be an adverse interaction functionality module that is configured to identify any potential adverse interactions between the current medications of encounter participant 228 and the approved RA medications defined within first result 250.

Automated clinical documentation process 10 may be configured to utilize machine vision (e.g., an RGB imaging system, an infrared imaging system, an ultraviolet imaging system, a SONAR imaging system, a laser imaging system, a RADAR imaging system and/or a thermal imaging system) to record a visual representation (e.g., machine vision encounter information 102) of the patient encounter (in addition to recording an audio representation (e.g., audio encounter information 106) of the patient encounter), wherein automated clinical documentation process 10 may index/synchronize the visual representation (e.g., machine vision encounter information 102) and the audio representation (e.g., audio encounter information 106) of the patient encounter to produce an encounter recording.

Accordingly and referring also to FIG. 19, automated clinical documentation process 10 may be configured to obtain 300 encounter information (e.g., machine vision encounter information 102 and/or audio encounter information 106) of a patient encounter (e.g., a visit to a doctor's office), wherein the encounter information (e.g., machine vision encounter information 102 and/or audio encounter information 106) includes machine vision encounter information and audio encounter information.

As discussed above, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office).

Accordingly and when obtaining 300 encounter information (e.g., machine vision encounter information 102 and/or audio encounter information 106), automated clinical documentation process 10 may utilize 312 a virtual assistant (e.g., virtual assistant 238) to prompt the patient to provide at least a portion of the encounter information (e.g., machine vision encounter information 102 and/or audio encounter information 106) during a pre-visit portion of the patient encounter (e.g., a visit to a doctor's office).

Further and when obtaining 300 encounter information (e.g., machine vision encounter information 102 and/or audio encounter information 106), automated clinical documentation process 10 may utilize 314 a virtual assistant (e.g., virtual assistant 238) to prompt the patient to provide at least a portion of the encounter information (e.g., machine vision encounter information 102 and/or audio encounter information 106) during a post-visit portion of the patient encounter (e.g., a visit to a doctor's office).

Figure 20:
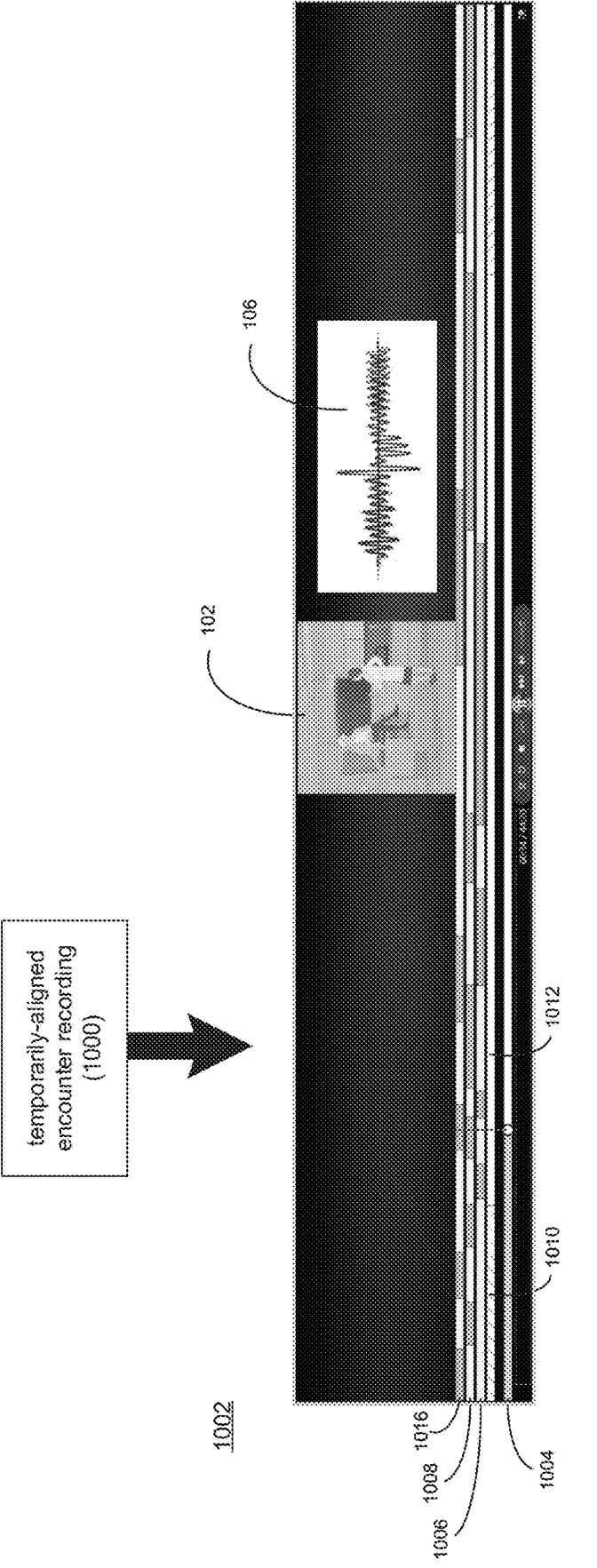
FIG. 20 is a diagrammatic view of an ACD media player for use with the automated clinical documentation process of FIG. 1.

Referring also to FIG. 20, automated clinical documentation process 10 may temporarily-align 950 machine vision encounter information 102 and audio encounter information 106 to produce temporarily-aligned encounter recording 1000, which may be rendered 952 for the user of modular ACD system 54 via ACD media player 1002. Specifically and in one particular implementation of ACD media player 1002, visual representation 1004 of the encounter information may allow the user of modular ACD system 54 to select a particular portion of encounter recording 1000 for rendering, wherein automated clinical documentation process 10 may then render the appropriate portion of machine vision encounter information 102 and audio encounter information 106 in a temporarily aligned fashion.

Automated clinical documentation process 10 may be configured to identify (e.g., temporally & visually) the individual encounter participants (e.g., one or more of encounter participants 226, 228, 230) within an encounter recording of a patient encounter (e.g., a visit to a doctor's office).

Accordingly and referring also to FIG. 21, automated clinical documentation process 10 may be configured to obtain 300 encounter information (e.g., machine vision encounter information 102 and/or audio encounter information 106) of a patient encounter (e.g., a visit to a doctor's office), wherein the encounter information (e.g., machine vision encounter information 102 and/or audio encounter information 106) includes machine vision encounter information and audio encounter information).

As discussed above, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office).

Accordingly and when obtaining 300 the encounter information (e.g., machine vision encounter information 102 and/or audio encounter information 106), automated clinical documentation process 10 may utilize 312 a virtual assistant (e.g., virtual assistant 238) to prompt the patient to provide at least a portion of the encounter information (e.g., machine vision encounter information 102 and/or audio encounter information 106) during a pre-visit portion of the patient encounter (e.g., a visit to a doctor's office).

Further and when obtaining 300 encounter information (e.g., machine vision encounter information 102 and/or audio encounter information 106), automated clinical documentation process 10 may utilize 314 a virtual assistant (e.g., virtual assistant 238) to prompt the patient to provide at least a portion of the encounter information (e.g., machine vision encounter information 102 and/or audio encounter information 106) during a post-visit portion of the patient encounter (e.g., a visit to a doctor's office).

Automated clinical documentation process 10 may generate 1050 an encounter transcript based, at least in part, upon the first portion of the encounter information (e.g., machine vision encounter information 102 and/or audio encounter information 106) and the at least a second portion of the encounter information (e.g., machine vision encounter information 102 and/or audio encounter information 106).

Automated clinical documentation process 10 may process 1052 the information (e.g., machine vision encounter information 102 and/or audio encounter information 106) information to: associate a first portion (e.g., machine vision encounter information 102A and/or audio encounter information 106A) of the encounter information (e.g., machine vision encounter information 102 and/or audio encounter information 106) with a first encounter participant (e.g., encounter participant 226), and associate at least a second portion (e.g., machine vision encounter information 102B and/or audio encounter information 106B) of the encounter information (e.g., machine vision encounter information 102 and/or audio encounter information 106) with at least a second encounter participant (e.g., encounter participant 228). The association of these various encounter information portions with the various encounter participants may be accomplished in one or more of the methodologies described above (via the use of one or more of voice prints, face prints, wearable tokens, utterances, interactions, etc.).

Once the above-described associations are made, automated clinical documentation process 10 may render 1054 a visual representation (e.g., visual representation 1004) of the encounter information (e.g., machine vision encounter information 102 and/or audio encounter information 106). As discussed above, visual representation 1004 of the encounter information may allow the user of modular ACD system 54 to select a particular portion of encounter recording 1000 for rendering.

Automated clinical documentation process 10 may render 1056 a first visual representation (e.g., first visual representation 1006) of the first portion (e.g., machine vision encounter information 102A and/or audio encounter information 106A) of the encounter information (e.g., machine vision encounter information 102 and/or audio encounter information 106) that is temporally-aligned with visual representation 1004 of the encounter information (e.g., machine vision encounter information 102 and/or audio encounter information 106). Specifically, first visual representation 1006 may be visually indicative of the portions of the encounter information during which the first encounter participant (e.g., encounter participant 226) was speaking (as illustrated by darker grey portions versus lighter grey portions).

Further, automated clinical documentation process 10 may render 1058 at least a second visual representation (e.g., second visual representation 1008) of the at least a second portion (e.g., machine vision encounter information 102B and/or audio encounter information 106B) of the encounter information (e.g., machine vision encounter information 102 and/or audio encounter information 106) that is temporally-aligned with visual representation 1004 of the encounter information (e.g., machine vision encounter information 102 and/or audio encounter information 106). Specifically, second visual representation 1008 may be visually indicative of the portions of the encounter information during which the second encounter participant (e.g., encounter participant 228) was speaking (as illustrated by darker grey portions versus lighter grey portions).

Additionally, automated clinical documentation process 10 may be configured to allow the user of modular ACD system 54 to filter 1060 the encounter information (e.g., machine vision encounter information 102 and/or audio encounter information 106) based upon one or more of the first visual representation (e.g., first visual representation 1006) and the at least a second visual representation (e.g., second visual representation 1008). For example, the user of modular ACD system 54 may select (e.g., via clicking) the appropriate visual representation (or appropriate visual representations) and automated clinical documentation process 10 may filter 1060 encounter recording 1000 based upon the user selections.

Automated clinical documentation process 10 may be configured to identify (e.g., temporally & visually) the individual portions of an encounter recording of a patient encounter (e.g., a visit to a doctor's office).

Accordingly and referring also to FIG. 22, automated clinical documentation process 10 may be configured to obtain 300 encounter information (e.g., machine vision encounter information 102 and/or audio encounter information 106) of a patient encounter (e.g., a visit to a doctor's office). When obtaining 300 encounter information (e.g., machine vision encounter information 102 and/or audio encounter information 106), automated clinical documentation process 10 may: obtain 306 encounter information (e.g., machine vision encounter information 102 and/or audio encounter information 106) from a medical professional (e.g., encounter participant 226); obtain 308 encounter information (e.g., machine vision encounter information 102 and/or audio encounter information 106) from a patient (e.g., encounter participant 228); and/or obtain 310 encounter information (e.g., machine vision encounter information 102 and/or audio encounter information 106) from a third party (e.g., encounter participant 230). Further and when obtaining 300 encounter information (e.g., machine vision encounter information 102 and/or audio encounter information 106), automated clinical documentation process 10 may obtain 300 the encounter information (e.g., machine vision encounter information 102 and/or audio encounter information 106) from previous (related or unrelated) patient encounters. For example, if the current patient encounter is actually the third visit that the patient is making concerning e.g., shortness of breath, the encounter information from the previous two visits (i.e., the previous two patient encounters) may be highly-related and may be obtained 300 by automated clinical documentation process 10.

As discussed above, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office).

Accordingly and when obtaining 300 encounter information (e.g., machine vision encounter information 102 and/or audio encounter information 106), automated clinical documentation process 10 may utilize 312 a virtual assistant (e.g., virtual assistant 238) to prompt the patient to provide at least a portion of the encounter information (e.g., machine vision encounter information 102 and/or audio encounter information 106) during a pre-visit portion of the patient encounter (e.g., a visit to a doctor's office).

Further and when obtaining 300 encounter information (e.g., machine vision encounter information 102 and/or audio encounter information 106), automated clinical documentation process 10 may utilize 314 a virtual assistant (e.g., virtual assistant 238) to prompt the patient to provide at least a portion of the encounter information (e.g., machine vision encounter information 102 and/or audio encounter information 106) during a post-visit portion of the patient encounter (e.g., a visit to a doctor's office).

Automated clinical documentation process 10 may process 1100 the encounter information (e.g., machine vision encounter information 102 and/or audio encounter information 106) to: associate a first portion of the encounter information (e.g., machine vision encounter information 102 and/or audio encounter information 106) with a first patient encounter portion (e.g., a pre-visit portion), and associate at least a second portion of the encounter information (e.g., machine vision encounter information 102 and/or audio encounter information 106) with at least a second patient encounter portion (e.g., the visit portion). The association of these various encounter information portions with the various patient encounter portions may be accomplished in one or more of the methodologies described above (via the use of one or more of voice prints, face prints, wearable tokens, utterances, interactions, etc., as well as the specific locations within monitored space 130 in which the various portions of the encounter information were generated).

Once the above-described associations are made, automated clinical documentation process 10 may render 1102 a visual representation (e.g., visual representation 1004) of the encounter information (e.g., machine vision encounter information 102 and/or audio encounter information 106). As discussed above, visual representation 1004 of the encounter information may allow the user of modular ACD system 54 to select a particular portion of encounter recording 1000 for rendering.

Automated clinical documentation process 10 may render 1104 a first visual representation (e.g., first visual representation 1010) of the first portion (e.g., a pre-visit portion) of the encounter information (e.g., machine vision encounter information 102 and/or audio encounter information 106) that is temporally-aligned with the visual representation 1004 of the encounter information (e.g., machine vision encounter information 102 and/or audio encounter information 106). Specifically, first visual representation 1010 may be visually indicative of the pre-visit portion of the encounter information.

Automated clinical documentation process 10 may render 1106 at least a second visual representation (e.g., second visual representation 1012) of the at least a second portion (e.g., a visit portion) of the encounter information (e.g., machine vision encounter information 102 and/or audio encounter information 106) that is temporally-aligned with visual representation 1004 of the encounter information (e.g., machine vision encounter information 102 and/or audio encounter information 106). Specifically, second visual representation 1012 may be visually indicative of the visit portion of the encounter information.

Additionally, automated clinical documentation process 10 may be configured to allow the user of modular ACD system 54 to filter 1108 the encounter information (e.g., machine vision encounter information 102 and/or audio encounter information 106) based upon one or more of the first visual representation (e.g., first visual representation 1010) and the at least a second visual representation (e.g., second visual representation 1012). For example, the user of modular ACD system 54 may select (e.g., via clicking) the appropriate visual representation (or appropriate visual representations) and automated clinical documentation process 10 may filter 1108 encounter recording 1000 based upon the user selections.

Automated clinical documentation process 10 may be configured to reactively identify (at the request of a user) the various portions of the encounter recording that are indicative of a specific medical condition.

Figure 23:
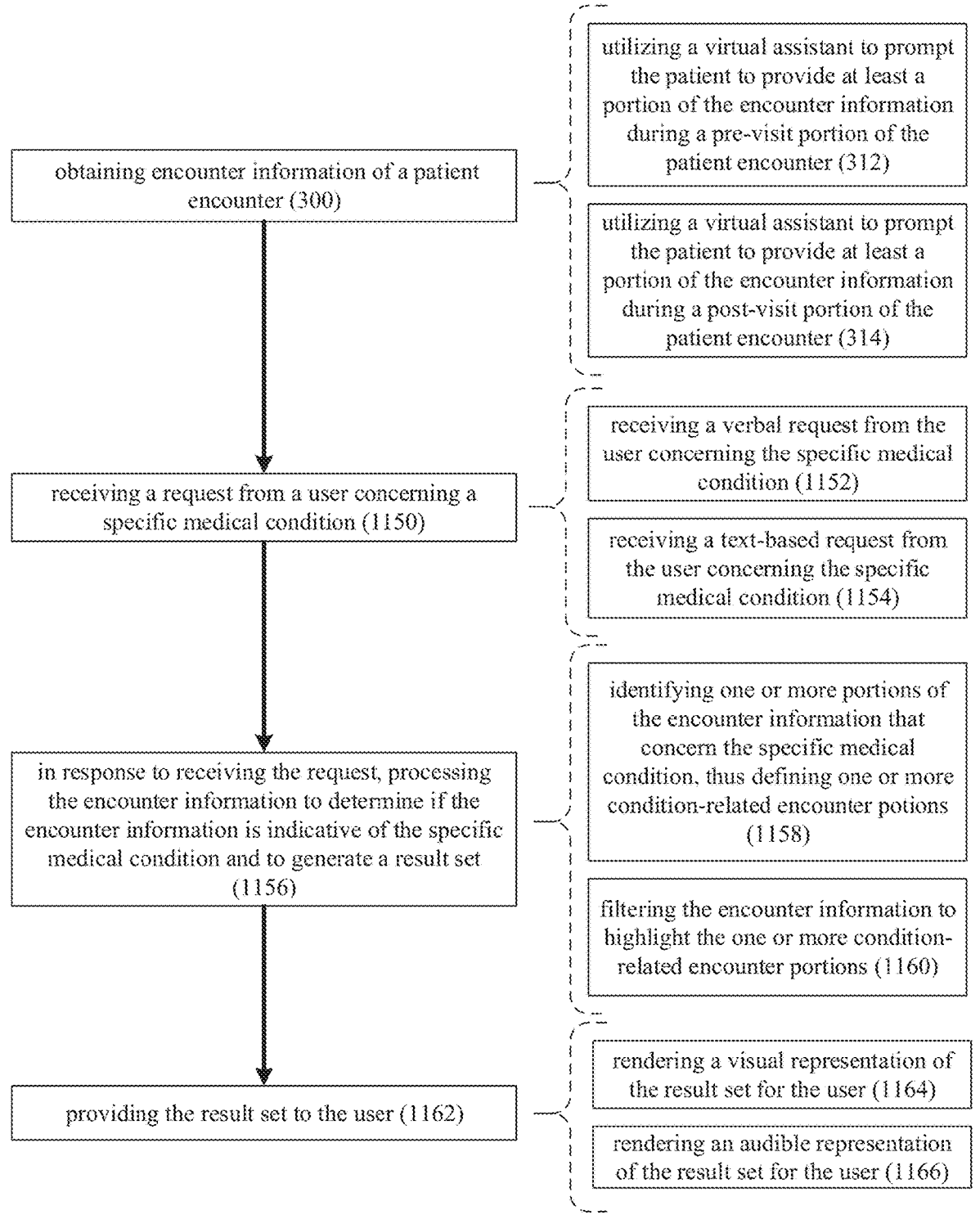
FIG. 23 is a flow chart of another implementation of the automated clinical documentation process of FIG. 1.

Accordingly and referring also to FIG. 23, automated clinical documentation process 10 may be configured to obtain 300 encounter information (e.g., machine vision encounter information 102 and/or audio encounter information 106) of a patient encounter (e.g., a visit to a doctor's office).

As discussed above, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office).

Accordingly and when obtaining 300 encounter information (e.g., machine vision encounter information 102 and/or audio encounter information 106), automated clinical documentation process 10 may utilize 312 a virtual assistant (e.g., virtual assistant 238) to prompt the patient to provide at least a portion of the encounter information (e.g., machine vision encounter information 102 and/or audio encounter information 106) during a pre-visit portion of the patient encounter (e.g., a visit to a doctor's office).

Further and when obtaining 300 encounter information (e.g., machine vision encounter information 102 and/or audio encounter information 106), automated clinical documentation process 10 may utilize 314 a virtual assistant (e.g., virtual assistant 238) to prompt the patient to provide at least a portion of the encounter information (e.g., machine vision encounter information 102 and/or audio encounter information 106) during a post-visit portion of the patient encounter (e.g., a visit to a doctor's office).

As discussed above, since machine vision system 100 and audio recording system 104 may be positioned throughout monitored space 130, all of the interactions between medical professionals (e.g., encounter participant 226), patients (e.g., encounter participant 228) and third parties (e.g., encounter participant 230) that occur during the patient encounter (e.g., encounter participant 228 visiting the doctor's office) within the monitored space (e.g., monitored space 130) of the clinical environment (e.g., the doctor's office) may be monitored/recorded/processed. Accordingly, a patient "check-in" area within monitored space 130 may be monitored to obtain encounter information (e.g., machine vision encounter information 102 and/or audio encounter information 106) during this pre-visit portion of the patient encounter (e.g., encounter participant 228 visiting the doctor's office). Additionally and as discussed above, this pre-visit encounter information may be obtained via e.g., virtual assistant 238 before the patient (e.g., encounter participant 228) has entered monitored space 130. Further, various rooms within monitored space 130 may be monitored to obtain encounter information (e.g., machine vision encounter information 102 and/or audio encounter information 106) during these various portions of the patient encounter (e.g., while meeting with the doctor, while vital signs and statistics are obtained, and while imaging is performed). Further, a patient "check-out" area within monitored space 130 may be monitored to obtain encounter information (e.g., machine vision encounter information 102 and/or audio encounter information 106) during this post-visit portion of the patient encounter (e.g., encounter participant 228 visiting the doctor's office). Additionally and as discussed above, this post-visit encounter information may be obtained via e.g., virtual assistant 238 after the patient (e.g., encounter participant 228) has left monitored space 130. Further and via machine vision encounter information 102, visual speech recognition (via visual lip-reading functionality) may be utilized by automated clinical documentation process 10 to further effectuate the gathering of audio encounter information 106.

Accordingly, a complete recording of the patient encounter (e.g., encounter participant 228 visiting the doctor's office) may be generated, wherein this encounter information (e.g., machine vision encounter information 102 and/or audio encounter information 106) may be processed 302 to generate an encounter transcript (e.g., encounter transcript 234) and at least a portion of this encounter transcript (e.g., encounter transcript 234) may be processed 304 to populate at least a portion of a medical record (e.g., medical record 236) associated with the patient encounter (e.g., the visit to the doctor's office).

Automated clinical documentation process 10 may receive 1150 a request from a user (e.g., a user of modular ACD system 54) concerning a specific medical condition. When receiving 1150 a request from a user (e.g., a user of modular ACD system 54), automated clinical documentation process 10 may: receive 1152 a verbal request from the user (e.g., a user of modular ACD system 54) concerning the specific medical condition; and/or receive 1154 a text-based request from the user (e.g., a user of modular ACD system 54) concerning the specific medical condition.

For example, assume that the user of modular ACD system 54 is encounter participant 226 (e.g., the doctor) who is examining encounter participant 228 (e.g., the patient). Accordingly, assume that encounter participant 226 (e.g., the doctor) is concerned that encounter participant 228 (e.g., the patient) may have diabetes. Accordingly, automated clinical documentation process 10 may receive 1150 a request (either verbal or text-based) from encounter participant 226 requesting that automated clinical documentation process 10 identify any portions of the encounter information (e.g., machine vision encounter information 102 and/or audio encounter information 106) that may be indicative of the presence of diabetes with respect to encounter participant 228.

In response to receiving 1150 the request, automated clinical documentation process 10 may process 1156 the encounter information (e.g., machine vision encounter information 102 and/or audio encounter information 106) to determine if the encounter information (e.g., machine vision encounter information 102 and/or audio encounter information 106) is indicative of this specific medical condition and to generate a result set.

As discussed above, ACD compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource.

Accordingly, automated clinical documentation process 10 may access the appropriate datasource to identify the symptoms for diabetes and may compare those identified symptoms to the data included within the encounter information (e.g., machine vision encounter information 102 and/or audio encounter information 106).

When processing 1156 the encounter information (e.g., machine vision encounter information 102 and/or audio encounter information 106), automated clinical documentation process 10 may identify 1158 one or more portions of the encounter information (e.g., machine vision encounter information 102 and/or audio encounter information 106) that concern the specific medical condition (in this example, diabetes), thus defining one or more condition-related encounter portions. Automated clinical documentation process 10 may then filter 1160 the encounter information (e.g., machine vision encounter information 102 and/or audio encounter information 106) to highlight the one or more condition-related encounter portions (thus defining result set 1016).

Automated clinical documentation process 10 may then provide 1162 result set 1016 to the user (e.g., encounter participant 226). When providing 1162 result set 1016 to the user (e.g., encounter participant 226), automated clinical documentation process 10 may render 1164 a visual representation of result set 1016 for the user (e.g., encounter participant 226) and/or may render 1166 an audible representation of result set 1016 for the user (e.g., encounter participant 226).

For example, automated clinical documentation process 10 may provide 1162 result set 1016 to encounter participant 226 in the manner shown in FIG. 20, wherein result set 1016 is visually indicative of the portions of the encounter information that concern a specific medical condition (in this example, diabetes). Additionally/alternatively, automated clinical documentation process 10 may provide 1162 result set 1016 as a private verbal message (e.g., that is rendered on an earbud worn by encounter participant 226) that provides the information requested by encounter participant 226 (e.g., "There are 23 portions of this patient encounter that indicate that this patient may have diabetes. An A1C test is recommended".

Automated clinical documentation process 10 may be configured to proactively scan the entire encounter recording to identify any specific medical conditions.

Figure 24:
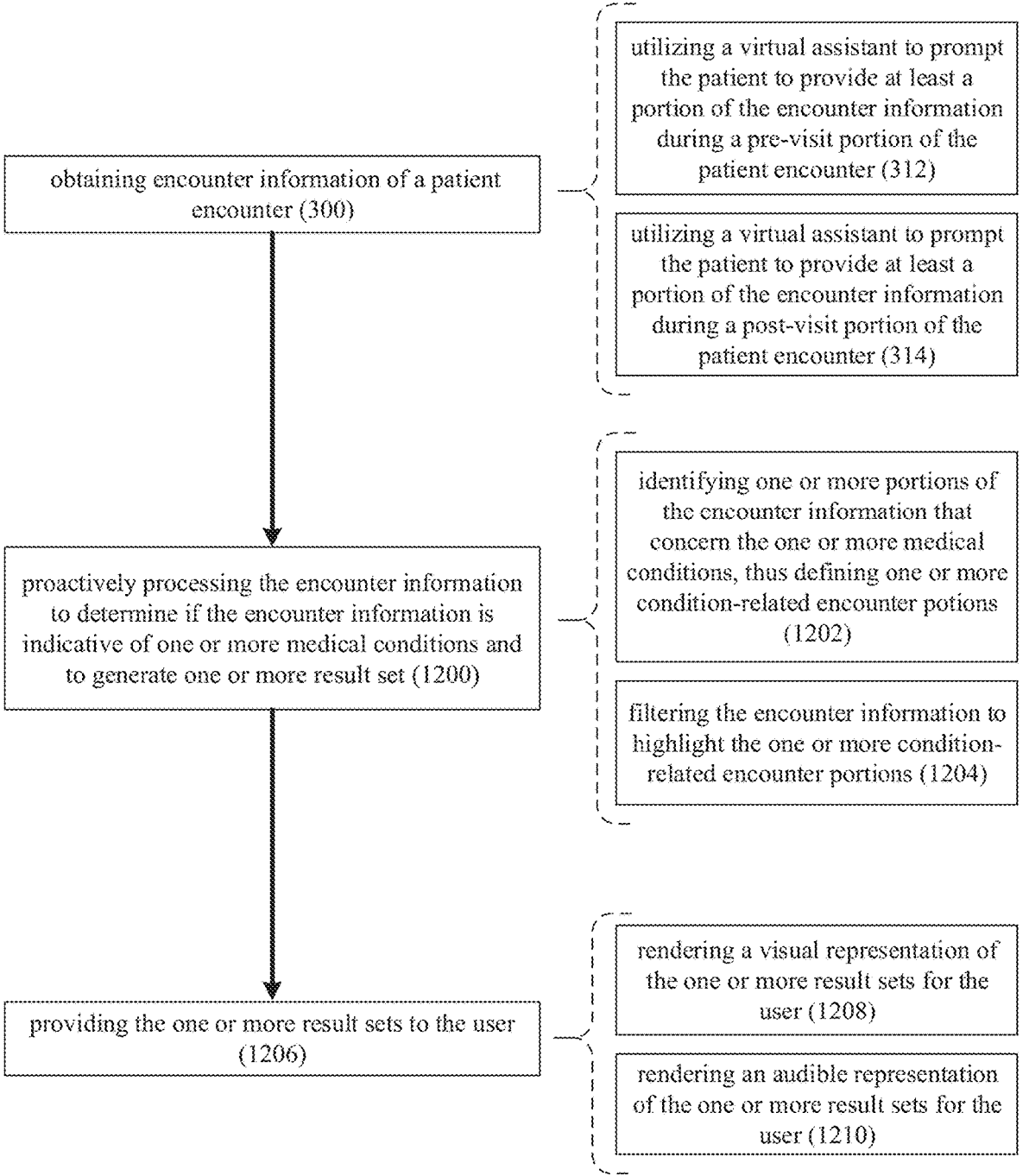
FIG. 24 is a flow chart of another implementation of the automated clinical documentation process of FIG. 1.

Accordingly and referring also to FIG. 24, automated clinical documentation process 10 may be configured to obtain 300 encounter information (e.g., machine vision encounter information 102 and/or audio encounter information 106) of a patient encounter (e.g., a visit to a doctor's office).

As discussed above, virtual assistant 238 may be configured to aid medical professionals (e.g., doctors, nurses, physician's assistants, lab technicians, physical therapists, scribes (e.g., a transcriptionist) and/or staff members involved in the patient encounter) with the gathering of encounter information (e.g., machine vision encounter information 102 and/or audio encounter information 106) during various portions of the patient encounter (e.g., encounter participant 228 visiting the doctor's office).

Accordingly and when obtaining 300 encounter information (e.g., machine vision encounter information 102 and/or audio encounter information 106), automated clinical documentation process 10 may utilize 312 a virtual assistant (e.g., virtual assistant 238) to prompt the patient to provide at least a portion of the encounter information (e.g., machine vision encounter information 102 and/or audio encounter information 106) during a pre-visit portion of the patient encounter (e.g., a visit to a doctor's office).

Further and when obtaining 300 encounter information (e.g., machine vision encounter information 102 and/or audio encounter information 106), automated clinical documentation process 10 may utilize 314 a virtual assistant (e.g., virtual assistant 238) to prompt the patient to provide at least a portion of the encounter information (e.g., machine vision encounter information 102 and/or audio encounter information 106) during a post-visit portion of the patient encounter (e.g., a visit to a doctor's office).

As discussed above, since machine vision system 100 and audio recording system 104 may be positioned throughout monitored space 130, all of the interactions between medical professionals (e.g., encounter participant 226), patients (e.g., encounter participant 228) and third parties (e.g., encounter participant 230) that occur during the patient encounter (e.g., encounter participant 228 visiting the doctor's office) within the monitored space (e.g., monitored space 130) of the clinical environment (e.g., the doctor's office) may be monitored/recorded/processed. Accordingly, a patient "check-in" area within monitored space 130 may be monitored to obtain encounter information (e.g., machine vision encounter information 102 and/or audio encounter information 106) during this pre-visit portion of the patient encounter (e.g., encounter participant 228 visiting the doctor's office). Additionally and as discussed above, this pre-visit encounter information may be obtained via e.g., virtual assistant 238 before the patient (e.g., encounter participant 228) has entered monitored space 130. Further, various rooms within monitored space 130 may be monitored to obtain encounter information (e.g., machine vision encounter information 102 and/or audio encounter information 106) during these various portions of the patient encounter (e.g., while meeting with the doctor, while vital signs and statistics are obtained, and while imaging is performed). Further, a patient "check-out" area within monitored space 130 may be monitored to obtain encounter information (e.g., machine vision encounter information 102 and/or audio encounter information 106) during this post-visit portion of the patient encounter (e.g., encounter participant 228 visiting the doctor's office). Additionally and as discussed above, this post-visit encounter information may be obtained via e.g., virtual assistant 238 after the patient (e.g., encounter participant 228) has left monitored space 130. Further and via machine vision encounter information 102, visual speech recognition (via visual lip-reading functionality) may be utilized by automated clinical documentation process 10 to further effectuate the gathering of audio encounter information 106.

Accordingly, a complete recording of the patient encounter (e.g., encounter participant 228 visiting the doctor's office) may be generated, wherein this encounter information (e.g., machine vision encounter information 102 and/or audio encounter information 106) may be processed 302 to generate an encounter transcript (e.g., encounter transcript 234) and at least a portion of this encounter transcript (e.g., encounter transcript 234) may be processed 304 to populate at least a portion of a medical record (e.g., medical record 236) associated with the patient encounter (e.g., the visit to the doctor's office).

Automated clinical documentation process 10 may proactively process 1200 the encounter information (e.g., machine vision encounter information 102 and/or audio encounter information 106) to determine if the encounter information (e.g., machine vision encounter information 102 and/or audio encounter information 106) is indicative of one or more medical conditions and to generate one or more result sets. For example, automated clinical documentation process 10 may continuously (or regularly) scan the encounter information (e.g., machine vision encounter information 102 and/or audio encounter information 106) to determine if this encounter information (e.g., machine vision encounter information 102 and/or audio encounter information 106) is indicative of one or more medical conditions.

As discussed above, ACD compute system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an inter-action identifier datasource, a medical conditions symptoms datasource, a prescriptions compatibility datasource, a medi-cal insurance coverage datasource, and a home healthcare datasource. Accordingly, automated clinical documentation process 10 may proactively access the appropriate data-source to identify the symptoms of various medical condi-tions (e.g., diabetes) and may compare the identified symp-toms of the various medical conditions to the data included within the encounter information (e.g., machine vision encounter information 102 and/or audio encounter informa-tion 106).

When proactively processing 1200 the encounter infor-mation (e.g., machine vision encounter information 102 and/or audio encounter information 106), automated clinical documentation process 10 may identify 1202 one or more portions of the encounter information (e.g., machine vision encounter information 102 and/or audio encounter informa-tion 106) that concern one or more medical conditions, thus defining one or more condition-related encounter portions. Automated clinical documentation process 10 may then filter 1204 the encounter information (e.g., machine vision encounter information 102 and/or audio encounter informa-tion 106) to highlight the one or more condition-related encounter portions.

Automated clinical documentation process 10 may pro-vide 1206 the one or more result sets (e.g., result set 1016) to the user (e.g., encounter participant 226). The one or more result sets (e.g., result set 1016) may include: a first result set indicative of a first medical condition; and at least a second result set indicative of at least a second medical condition. For example, while FIG. 20 illustrates a single/consolidated result set, this is for illustrative purpose only and is not intended to be a limitation of this disclosure, as other configurations are possible and are considered to be within the scope of this disclosure. For example, assume that automated clinical documentation process 10 found (within the encounter information) data that indicates that encounter participant 228 may have diabetes and may have heart disease. Accordingly and in such a situation, result set 1016 may include a first result set that is indicative of diabetes and a second result set indicative of heart disease.

When providing 1206 the one or more result sets (e.g., result set 1016) to the user (e.g., encounter participant 226), automated clinical documentation process 10 may render 1208 a visual representation of the one or more result sets (e.g., result set 1016) for the user (e.g., encounter participant 226) and/or may render 1210 an audible representation of the one or more result sets (e.g., result set 1016) for the user (e.g., encounter participant 226).

For example, automated clinical documentation process 10 may provide 1206 result set 1016 to encounter participant 226 in the manner shown in FIG. 20, wherein result set 1016 is visually indicative of the portions of the encounter information that concern a specific medical condition (in this example, diabetes and/or heart disease). Additionally/alter-natively, automated clinical documentation process 10 may provide 1206 result set 1016 as a private verbal message (e.g., that is rendered on an earbud worn by encounter participant 226) that provides the information requested by encounter participant 226 (e.g., "There are 23 portions of this patient encounter that indicate that this patient may have diabetes. An A1C test is recommended There are 16 portions of this patient encounter that indicate that this patient may have heart disease. An echocardiogram is recommended." Non-Medical Applications:

While automated clinical documentation process 10 is described above as being utilized to automate the collection and processing of clinical encounter information to generate/store/distribute medical records, this is for illustrative pur-poses only and is not intended to be a limitation of this disclosure, as other configurations are possible and are considered to be within the scope of this disclosure.

As is known in the art, Merriam-Webster defines "clini-cal" as "analytical or coolly dispassionate". Accordingly, automated clinical documentation process 10 is a process that documents an encounter in a detached and analytical fashion, free from emotion/opinion/bias. Therefore, auto-mated clinical documentation process 10 generally (and/or ACD system 54 specifically) may be configured to automate the collection and processing of various types of encounter information and to generate/store/distribute/process such information.

Specifically, automated clinical documentation process 10 generally (and/or ACD system 54 specifically) may be configured to be utilized in any environment in which people gather and converse. Accordingly, automated clinical docu-mentation process 10 generally (and/or ACD system 54 specifically) may be configured to monitor discussions in any environment in which people gather and converse, wherein these discussions may be analyzed to extract and organize information included/defined within these conver-sations, so that e.g.:

participants may be identified;
    information may be diarized/summarized/stored/verified/
        supplemented;
    forms may be populated/stored;
    data may be accessed/obtained/integrated;
    orders may be placed/processed/verified;
    recommendations may be made/received;
    input/feedback may be received;
    products/services may be identified/offered;
    solutions may be identified/offered;
    inconsistences may be identified/addressed;
    conflicts may be identified/resolved;
    action items may be defined/assigned;
    calendar entries may be defined/scheduled;
    intake tasks may be defined/scheduled/automated; and
    follow-up tasks may be defined/scheduled/automated.

Specific and illustrative examples of such encounter infor-mation that may be monitored and processed may include but are not limited to:
Financial Information:

For example, automated clinical documentation process 10 generally (and/or ACD system 54 specifically) may be configured to automate the collection and processing of financial data that is generated during an encounter in which financial information is discussed. An example of such an encounter may include but is not limited to a meeting between an individual and a financial advisor. For example, automated clinical documentation process 10 may be con-figured to supplement/complement a financial advisor's knowledge by recommending products, answering questions and making offers based on the conversation that the finan-cial advisor is having with a client in essentially real time, as well as completing various forms, mortgage applications, stock purchase/sale orders, estate planning documents, etc.

Benefits: The benefits achievable by automated clinical documentation process 10 when configured to process financial information may be considerable. For example and as is understandable, financial advisors may not know all things concerning e.g., financial and investment instruments. Accordingly, automated clinical documentation process 10 (when configured to process financial information) may monitor a conversation between the financial advisor and the client. Automated clinical documentation process 10 may then utilize natural language processing and artificial intelligence to identify issues/questions within the conversation and leverage collective knowledge to provide pertinent information to the financial advisor.

For example, assume that a client visits a financial advisor seeking financial advice concerning tax free/tax deferred retirement savings. Accordingly and through the use of the various systems described above (e.g., audio input device 30, display device 32, machine vision input device 34, and audio rendering device 116), automated clinical documentation process 10 (when configured to process financial information) may monitor the conversation between the financial advisor and the client. Assuming that this is the first time that this client is meeting with his financial advisor, the information obtained during this initial meeting may be parsed and used to populate the various fields of a client intake form. For example, the client may identify themself and their name may be entered into the client intake form. Additionally, automated clinical documentation process 10 may be configured to define a voiceprint and/or face print for the client so that e.g. in the future this voiceprint and/or face print may be utilized to authenticate the client's identity when they want to access their data. Additionally, when the client identifies e.g. their age, their marital status, their spouse's name, their spouse's age, and whether or not they have children and (if so) the age of their children, all of this information may be used to populate this client intake form.

Continuing with the above stated example, assume that the client asks about tax-free/tax-deferred retirement savings plans. The financial advisor may then ask them what their income was last year. As automated clinical documentation process 10 may be monitoring this conversation via audio input device 30, automated clinical documentation process 10 may "hear" that the client is interested in tax-free/tax-deferred retirement savings plans and what their income level is. Accordingly and through the use of the above-described natural language processing and artificial intelligence, automated clinical documentation process 10 may determine whether or not the client qualifies for a 401(k) retirement plan, a pre-tax/post-tax traditional IRA plan, and/or a pre-tax/post-tax Roth IRA plan. Upon making such a determination, automated clinical documentation process 10 may provide supplemental information to the financial advisor so that the financial advisor may provide guidance to the client.

For example, automated clinical documentation process 10 may render (on display device 32) a list of the tax-free/tax-deferred retirement savings plans for which the client qualifies. Additionally/alternatively, this information may be audibly rendered (e.g. covertly into an earbud worn by the financial advisor) so that the financial advisor may provide such information to the client.

Accordingly and through the use of such a system, automated clinical documentation process 10 (when configured to process financial information) may monitor the conversation between (in this example) the financial advisor and a client to e.g. gather information and populate client intake forms, generate voice prints and/or face prints for client authentication, listen to inquiries made by the client, and provide responses to those inquiries so that the financial advisor may provide guidance to the client.

Additionally, automated clinical documentation process 10 may be configured to monitor the advice that the financial advisor is providing to the client and confirm the accuracy of the same, wherein covert corrections/notifications may be provided to the financial advisor in the event that the financial advisor misspoke (e.g., advising the client that they qualify for a retirement plan when they actually do not qualify).

Further, automated clinical documentation process 10 may be configured to provide guidance to the financial advisor/client even when such guidance is not sought. For example, if this client said that they have children, automated clinical documentation process 10 may prompt the financial advisor to inquire as to what college savings plans (e.g. 529$s$) they have in place for their children. And if none are in place, the financial advisor may be prompted to explain the tax benefits of such plans.

Further still, automated clinical documentation process 10 may be configured to covertly provide information to the financial advisor that may assist in building a relationship between the financial advisor and client. For example, assume that the client explained that his wife's name was Jill (during the first meeting between the client and the financial advisor) and the client explained that he and his wife were going to be visiting Italy over the summer. Assume that the client returns to meet with the financial advisor in the fall. During the first visit, automated clinical documentation process 10 may (as discussed above) populate a client intake form that identifies the client spouse as Jill. Further, automated clinical documentation process 10 may make a note that the client and Jill are going to be visiting Italy in the summer of 2020. Assuming that this follow-up meeting is after the summer of 2020, automated clinical documentation process 10 may covertly prompt the financial advisor to ask the client if he and Jill enjoyed Italy, thus enabling the establishment of goodwill between the client and the financial advisor.

Automated clinical documentation process 10 may further be configured to auto-populate forms that may be required based upon the needs of the client. For example, if the client needs to fill out a certain tax form concerning an IRA rollover, automated clinical documentation process 10 may be configured to obtain necessary information based on a conversation between the financial advisor and the client and/or proactively obtain the required information from a datastore accessible by automated clinical documentation process 10, populate the appropriate form needed to effectuate e.g., the IRA rollover with the data obtained from the datastore, and render (e.g. print) the populated form so that the client may execute the same.

Automated clinical documentation process 10 may further be configured to effectuate the functionality of a digital assistant, wherein automated clinical documentation process 10 may monitor the conversation between (in this example) the financial advisor and the client so that items that were mentioned may be flagged for follow-up. For example, assume that during the above-described conversation between the financial advisor and the client that the client stated that they are interested in setting up 529 college savings accounts for their children and they asked the financial advisor to provide them information concerning the same. Accordingly, automated clinical documentation process may enter (e.g. into a client-specific to do list) "Send 529 information to the Smith family". Additionally, in the event that the client says they would like to have a follow-up meeting in three weeks to chat about 529's, automated clinical documentation process 10 may schedule a meeting within the calendar of the financial advisor for such a discussion.

Life Coach Information:

For example, automated clinical documentation process 10 generally (and/or ACD system 54 specifically) may be configured to automate the collection and processing of life coach data that is generated during an encounter in which life coach information is discussed. An example of such an encounter may include but is not limited to a meeting between a life coach professional and a person whom they are representing. For example, automated clinical documentation process 10 may be configured to supplement/complement a life coach professional's knowledge by recommending strategies, answering questions and providing advice based on the conversation that the life coach professional is having with their client in essentially real time, as well as documenting/memorializing the conversation, making a list of action items, setting goals, identifying milestones, etc.

Benefits: The benefits achievable by automated clinical documentation process 10 when configured to process life coach information may be considerable. For example and as is understandable, life coach professionals may not know all things concerning e.g., the latest motivational and goal setting strategies and procedures. Accordingly, automated clinical documentation process 10 generally (and/or ACD system 54 specifically) may be configured to supplement the knowledge of the life coach professional, as well as monitor the life coach session to ensure that the life coach professional is e.g., utilizing best practices and adhering to industry norms.

For example and as is known in the art, a life coach professional may work one-on-one with a client to e.g., support personal growth, effectuate behavior modification, and enable goal-setting. Based on the premise that most people can achieve their goals if properly guided, a life coach professional may act as a mentor and may assist the client in the process of taking the life-improving actions necessary to take control of their future.

General duties of a life coach may include but are not limited to:

Meeting with clients to discuss needs and goals;

Developing strategies and plans to assist the client in addressing those needs and meeting those goals; and Keeping records of the progress of the client.

Some of the areas in which life coaching may be beneficial may include but are not limited to:

Health and fitness;

Career goals;

Work-life balance;

Finding your purpose in life;

Work productivity;

Setting educational goals;

Dating;

Spirituality;

Prioritization; and

General life motivation.

Accordingly, automated clinical documentation process 10 (when configured to process life coach information) may monitor a conversation between the life coach professional and the client. Automated clinical documentation process 10 may then utilize natural language processing and artificial intelligence to identify issues/questions within the conversation and leverage collective knowledge to provide pertinent information to the life coach professional.

Legal Information:

For example, automated clinical documentation process 10 generally (and/or ACD system 54 specifically) may be configured to automate the collection and processing of legal data that is generated during an encounter in which legal information is discussed. An example of such an encounter may include but is not limited to a meeting between a legal professional and a person whom they are representing. For example, automated clinical documentation process 10 may be configured to supplement/complement a legal professional's knowledge by recommending strategies, answering questions and providing advice based on the conversation that the legal professional is having with their client in essentially real time, as well as completing hearing/deposition transcripts, warrants, court orders/judgements, various applications for the foregoing and other items, etc.

Benefits: The benefits achievable by automated clinical documentation process 10 when configured to process legal information may be considerable. For example and as is understandable, legal professionals may not know all things concerning e.g., various legal situations, events and procedures. Accordingly, automated clinical documentation process 10 (when configured to process legal information) may monitor a conversation between the legal professional and the client. Automated clinical documentation process 10 may then utilize natural language processing and artificial intelligence to identify issues/questions within the conversation and leverage collective knowledge to provide pertinent information to the legal professional.

For example, assume that a deposition is occurring where a defendant in a lawsuit (who is being represented by a first group of attorneys) is being asked questions by the plaintiff in the law suit (who is being represented by a second group of attorneys). Accordingly and through the use of the various systems described above (e.g., audio input device 30, display device 32, machine vision input device 34, and audio rendering device 116), automated clinical documentation process 10 (when configured to process legal information) may monitor the conversation between the defendant/first group of attorneys and the plaintiff/second group of attorneys. In such a situation, automated clinical documentation process 10 (when configured to process legal information) may be configured to effectuate the functionality of a court transcriptionist.

For example, the participants in the deposition may be asked to identify themselves (e.g. provide name and title). Automated clinical documentation process 10 may use this information to populate an attendance log concerning the deposition and may be configured to define a voiceprint and/or face print for each attendee of the deposition.

Accordingly and once the deposition actually starts, automated clinical documentation process 10 may monitor the deposition and may (via the above described voice prints/face prints) diarize the same, essentially replicating the functionality of a court transcriptionist. Basically, automated clinical documentation process 10 may generate a diary of the deposition proceeding that reads like a movie script, wherein e.g. each spoken statement is transcribed and the speaker of that spoken statement is identified (via the voiceprint/face print).

Additionally and through the use of the above-describe natural language processing and artificial intelligence, traditional legal tasks may be efficiently effectuated. For example, suppose that (during the deposition) an objection is made and a piece of case law is cited as the basis for the objection. If the non-objecting attorney believes that this piece of case law is no longer valid (e.g. due to it being overturned by a higher court), the non-objecting attorney may ask automated clinical documentation process 10 (when configured to process legal information) to determine the status of the relied-upon piece of case law (i.e., whether the piece of case law is still valid or has been overturned). Automated clinical documentation process may then provide an answer to the non-objecting attorney (e.g., the case is still valid or the case was overturned by the 1$^{st}$ Circuit Court of Appeals in 2016, which was affirmed by the US Supreme Court in 2017).

Telecom Information:

For example, automated clinical documentation process 10 generally (and/or ACD system 54 specifically) may be configured to automate the collection and processing of telecom data that is generated during an encounter between a caller and a sales/service representative. An example of such an encounter may include but is not limited to a telephone call and/or chat session between a sales/service representative and a customer who is having a problem with their cable television service. For example, automated clinical documentation process 10 may be configured to supplement/complement a service representative's knowledge by recommending plans/products, trouble-shooting procedures, answering questions and providing advice based on the conversation that the service representative is having with their customer in essentially real time.

Benefits: The benefits achievable by automated clinical documentation process 10 when configured to process telecom information may be considerable. For example and as is understandable, sales/service representatives may not know all things concerning e.g., various service plans, available products, trouble-shooting procedures, and warranty coverage. Accordingly and through the use of the various systems described above (e.g., audio input device 30, display device 32, machine vision input device 34, and audio rendering device 116), automated clinical documentation process 10 (when configured to process telecom information) may monitor a conversation (e.g., voice or text) between the service representative and the caller. Automated clinical documentation process 10 may then utilize natural language processing and artificial intelligence to identify issues/questions within the conversation and leverage collective knowledge to provide pertinent information to the telecom salesperson.

For example, assume that a user of a cable television service is having a difficult time tuning to one of their pay channels within their cable TV channel list. Accordingly, this user may call up (or message) their cable television service and chat with a customer service representative. Automated clinical documentation process 10 (when configured to process telecom information) may e.g. utilize caller ID, IP addresses and/or voice prints to identify the caller and obtain information concerning their account, their location, their equipment, their service plan, etc.

Assume for this example that the caller explains to the service representative that they cannot tune their cable box to the desired channel. Automated clinical documentation process 10 may e.g. first confirm that their current service plan includes the channel that the caller is trying to access. In the event that the service plan does not include such channel, automated clinical documentation process 10 may notify the service representative (e.g. via a text-based message visible on a display accessible by the service representative or via an earbud) that the channel is not included in their service plan. Automated clinical documentation process 10 may then provide information to the service representative concerning which service plans include the channel about which the caller is inquiring to see if e.g., they want to upgrade/change their plan to one that includes the channel in question. Accordingly, automated clinical documentation process 10 may assist the service representative in upselling products/services by identifying which service plans include access to the channel that the caller wishes to watch.

Further, automated clinical documentation process 10 may assist the service representative by identifying any promotional products/services that the cable television service is offering. For example, if the channel in question is available via the ABC Package and there is a promotional offer in which you can get the ABC Package for free if you upgrade to higher speed internet, automated clinical documentation process 10 may assist the service representative by informing the service representative of this promotion so that the service representative may explain this offer to the caller and see if the caller is interested.

Additionally, assume that automated clinical documentation process 10 determines that the reason that the desired channel is no longer viewable is because the cable modem that the caller is using is out-of-date. Accordingly, automated clinical documentation process 10 may notify the service representative (e.g., via a display or an earbud) that the caller's cable modem is out-of-date and may provide information to the service representative that the cable television service has a service plan that would keep all of the caller's hardware up-to-date for only $10 per month, thus allowing the service representative to provide such information to the caller.

In the event that the channel is indeed included in the current service plan of the caller, automated clinical documentation process 10 may begin to provide prompts to the service representative concerning a troubleshooting procedure that may be utilized to identify the problem. For example, automated clinical documentation process 10 (via e.g. a display or an earbud) may provide the service representative with a sequence of steps that the caller can perform in order to (hopefully) rectify the situation. For example, the service representative may instruct the caller to first unplug the cable box from the electrical outlet and let it sit for 30 seconds and then plug it in so that it may reboot. In the event that this procedure does not fix the problem, the list provided by automated clinical documentation process 10 may instruct the service representative to send a reset signal to the cable box in question. In the event that this procedure does not fix the problem, automated clinical documentation process 10 may determine that a new cable box is needed and may assist the service representative in scheduling a service call so that the faulty cable box may be replaced by a service technician.

As discussed above, automated clinical documentation process 10 (when configured to process telecom information) may monitor a conversation (e.g., voice or text) between a service representative and a caller. Further, automated clinical documentation process 10 may be configured to generate a summary report that may be provided to a Customer Relationship Management (CRM) platform for quality assurance purposes, engagement recordkeeping, service representative reviews, etc.

Additionally/alternatively, automated clinical documentation process 10 may be configured to generate an engagement plan that may be provided to the caller. For example, assume that a caller was calling a service representative concerning their cellular plan, explaining that they are going to be travelling internationally and needed to have their phone configured for international roaming. Automated clinical documentation process 10 may monitor this conversation between the service representative and the caller via a voice call or chat session (e.g., live/asynchronous/virtual), wherein the service representative provides instructions to the caller concerning how to enable international roaming. Automated clinical documentation process 10 may transcribe the conversation, identify one or more action items (i.e., next steps), create a summary report, and auto-generate an outbound message that is provided to the caller, wherein such an outbound message may contain the summary report and may identify the action items for the caller.

An example of such an outbound message may be as follows:

Hi Robert, thank you for talking to Ken (your ATT engagement specialist) to set up international roaming for your ATT phone. The summary of your discussion is as follows:

Action: Set up roaming for 555.123.1234 for travel to Spain and UK

When: Starting on 12 Nov. 2020 and Ending on 30 Nov. 2020

Action Items:

Please shut down your ATT phone.

Please restart your ATT phone.

Please confirm that roaming is on within Settings>>General Roaming. Click this link to see an example video.

ATT has some of the best deals on the hottest new iPhones and there is still time to get one before your trip. Click this link to see the latest offers.

Retail Information:

For example, automated clinical documentation process 10 generally (and/or ACD system 54 specifically) may be configured to automate the collection and processing of retail data that is generated during an encounter in which retail information is discussed. An example of such an encounter may include but is not limited to a meeting between a salesclerk at a department store and a person interested in purchasing a particular product. For example, automated clinical documentation process 10 may be configured to supplement/complement a salesclerk's knowledge by recommending products, answering questions and providing advice based upon the conversation that the salesclerk is having with their customer in essentially real time, as well as enabling electronic checkout (i.e., without the need to visit a register), completing work order forms, financial/sales agreements, product order forms, warranty forms, etc.

Benefits: The benefits achievable by automated clinical documentation process 10 when configured to process retail information may be considerable. For example and as is understandable, salesclerks may not know all things concerning e.g., the assortment of products offered and the location of the same. Accordingly and through the use of the various systems described above (e.g., audio input device 30, display device 32, machine vision input device 34, and audio rendering device 116), automated clinical documentation process 10 (when configured to process retail information) may monitor a conversation between the salesclerk and the customer. Automated clinical documentation process 10 may then utilize natural language processing and artificial intelligence to identify issues/questions within the conversation and leverage collective knowledge to provide pertinent information to the salesclerk.

For example, assume that a customer goes to a local department store and they are looking for several items, including an electric drill. So this customer approaches a salesclerk and asks them if they sell electric drills and, if so, where they are. Automated clinical documentation process 10 (when configured to process retail information) may monitor this conversation and identify the issues that need to be addressed through the use of the above-described natural language processing and artificial intelligence. For example, automated clinical documentation process 10 may identify the phrase "electric drill" within the statement made by the customer and may examine inventory records for the department store and determine that the department store does indeed sell electric drills. Further, automated clinical documentation process 10 may determine that the customer is asking about the location of these electric drills and, upon checking product stocking charts for the department store, may determine that electric drills are in the hardware section (aisle 23, bays 16-20).

Additionally, automated clinical documentation process 10 may be configured to address additional questions that the customer may have, such as "What electric drills the have that cost under $30?", "What electric drill has the longest warranty?", "What electric drills do you have from DeWalt?" and "Do you have drill bits for drilling into cement?". When providing answers concerning these questions raised by the customer, automated clinical documentation process 10 may overtly provide the information onto a display screen (e.g. a handheld electronic device) so that the customer may review the same. Alternatively, automated clinical documentation process 10 may covertly provide the information in an earbud so that the salesclerk may verbally provide the information to the customer.

Further, assume that a family goes into a local wireless carrier store to inquire about cell phones and cell phone plans. Accordingly and through the use of the various systems described above (e.g., audio input device 30, display device 32, machine vision input device 34, and audio rendering device 116), automated clinical documentation process 10 (when configured to process retail information) may monitor the conversation between the family and salesclerk and provide guidance and insight with respect to such conversation through the use of the above-described natural language processing and artificial intelligence. For example, assume that the family asks the salesclerk if there are any sales/promotions on the latest iPhones. If so, automated clinical documentation process 10 (when configured to process retail information) may covertly provide a list of sales/promotions to the salesclerk via e.g., an earbud assembly or may overly provide a list of sales/promotions to the salesclerk via e.g., a client electronic device (e.g., a smart phone, a tablet, a laptop, or a display).

Additionally, assume that the family inquires as to what is the best phone to buy and/or what is the best data plan to be on when you do extensive international traveling. Accordingly, automated clinical documentation process 10 (when configured to process retail information) may e.g. render a list of applicable phones/data plans on a client electronic device (e.g. a smart phone, a tablet, a laptop, or display) so that such options may be reviewed with the salesclerk. Further, in the event that automated clinical documentation process 10 determines that one or more members of the family is interested in a cellular telephone that is not compatible with the cellular networks in various countries around the world, automated clinical documentation process 10 may prompt the salesclerk to inquire as to whether this family member travels to e.g., Countries A, B or C.

Additionally, as automated clinical documentation process 10 may be monitoring the conversation between the family and the salesclerk, automated clinical documentation process 10 may determine the quantity of cellular telephones they are interested in purchasing. Automated clinical documentation process 10 may then review the various promotional plans being offered by the cell phone manufacturers, as well as any the available data plan options, so that automated clinical documentation process 10 may present the phones and data plans that are most advantageous to the family.

Additionally, automated clinical documentation process 10 may monitor the conversation between the family and the salesclerk to identify and/or correct any mistakes or misrepresentations that the salesclerk may have inadvertently made. For example, if the user said that they often travel to Country X and they are in the process of purchasing Cellular Telephone Y (which is not usable within Country X), automated clinical documentation process 10 may covertly notify (e.g. via an earbud) the salesclerk that Cellular Telephone Y will not function properly within Country X.

Business Information:

For example, automated clinical documentation process 10 generally (and/or ACD system 54 specifically) may be configured to automate the collection and processing of business data that is generated during an encounter in which business information is discussed. Examples of such an encounter may include but are not limited to business meetings, business presentations, business events, tradeshows, promotions, full video and/or audio conferences (i.e., where there is no physical meeting and all of the participants are attending the meeting "electronically") and partial video/audio conferences (i.e., where there is a physical meeting and some of the participants are attending the meeting "electronically"). For example, automated clinical documentation process 10 may be configured to monitor discussions during a Board of Directors meeting, where corporate business plans are discussed, corporate milestones are defined, and corporate progress is analyzed.

Benefits: The benefits achievable by automated clinical documentation process 10 when configured to process business information may be considerable. For example and through the use of the various systems described above (e.g., audio input device 30, display device 32, machine vision input device 34, and audio rendering device 116), automated clinical documentation process 10 (when configured to process business information) may monitor such business discussions/conversations. Automated clinical documentation process 10 may then utilize natural language processing and artificial intelligence to identify, record and analyze such discussions. identify issues/questions within these discussions and leverage collective knowledge to provide pertinent information to the appropriate parties.

For example, assume that the Jones Corporation is having their annual Board of Directors meeting at their corporate offices. Accordingly, automated clinical documentation process 10 (when configured to process business information) may be configured to monitor discussions during this Board of Directors meeting. For example, the various systems described above (e.g., audio input device 30, display device 32, machine vision input device 34, and audio rendering device 116) may be positioned throughout the room in which the Board of Directors meeting is occurring so that discussions during this meeting may be recorded and processed by automated clinical documentation process 10.

For example and when initiating the Board of Directors meeting, attendees may be asked to identify themselves so that automated clinical documentation process 10 may assign a voiceprint and/or a face print to each attendee. Further, automated clinical documentation process 10 may be configured to transcribe any and all discussions that occur during this Board of Directors meeting. As the identity of the individual speakers would be known via the above-described voice prints/face prints, this transcription of the discussions during the Board of Directors meeting may be diarized so that individual statements may be associated with individual speakers/attendees.

Assume that during this Board of Directors meeting, the previous performance of the Jones Corporation is discussed, as is the anticipated future performance of the Jones Corporation. Accordingly, previous performance may be analyzed, sales projections may be made, hiring projections may be made, revenue projections may be made, etc. Through the use of artificial intelligence and machine learning, such information embedded within these discussions may be identified/summarized/expanded upon for use in various corporate reports (e.g. such as shareholder reports, employee reports, and management reports). Additionally, future targets and/or milestones may be identified, wherein automated clinical documentation process 10 may identify these targets and/or milestones as action items. For example, assume that one of these milestones is to expand sales in the Pacific Rim by 20% over the next calendar year. Accordingly, automated clinical documentation process 10 may identify this as a milestone. Further, assume that the Board of Directors tasked Susan Smith (Executive Vice President of sales in Asia) as the point person that should spearhead this expansion effort. Accordingly, the milestone "Expand Sales in the Pacific Rim by 20%" may be assigned to Susan Smith (Executive Vice President of sales in Asia).

As automated clinical documentation process 10 may have access to e.g. sales figures in the Pacific Rim, automated clinical documentation process 10 may access such sales figures during subsequent Board of Directors meetings so that the success of the "Expand Sales in the Pacific Rim by 20%" (as spearheaded by Susan Smith) may be determined/analyzed.

Additionally, the use of automated clinical documentation process 10 need not be mono-directional in nature. For example, automated clinical documentation process 10 may be configured so that attendees of the Board of Directors meeting may make inquiries concerning various pieces of data. Therefore, an attendee of the Board of Directors meeting may ask automated clinical documentation process 10 what the sales figures were for Australia in calendar year 2018. Automated clinical documentation process 10 (e.g., through the use of various APIs and external data stores) may access such information and provide the same to the requester (e.g. via a display or an earbud).

Further, automated clinical documentation process 10 may be configured to perform more complex tasks. For example, assume for illustrative purposes that during this Board of Directors meeting, the board members discuss the issuance of an additional 1,000,000 shares of Jones Corporation common stock to generate revenue to fund the above-described Pacific Rim expansion. Accordingly, automated clinical documentation process 10 may be configured to identify the pertinent information within that statement (e.g., "issue", "1 million shares" and "common stock") so that this information (and other information obtained via remote datastores) may be utilized to populate the various forms required to initiate such a stock offering (e.g., SEC forms, disclosure forms, etc.). Once populated, automated clinical documentation process 10 may be configured to provide these populated forms to the appropriate parties (e.g. the CEO of the Jones Corporation, the CFO of the Jones Corporation, the corporate legal department of the Jones Corporation, and outside counsel of the Jones Corporation) for review/execution/filing.

Concept #1

As discussed above, automated clinical documentation process 10 may be executed within one or more of: a financial environment; a life coach environment; a legal environment; a telecom environment; a retail environment; and a business environment.

Figure 25:
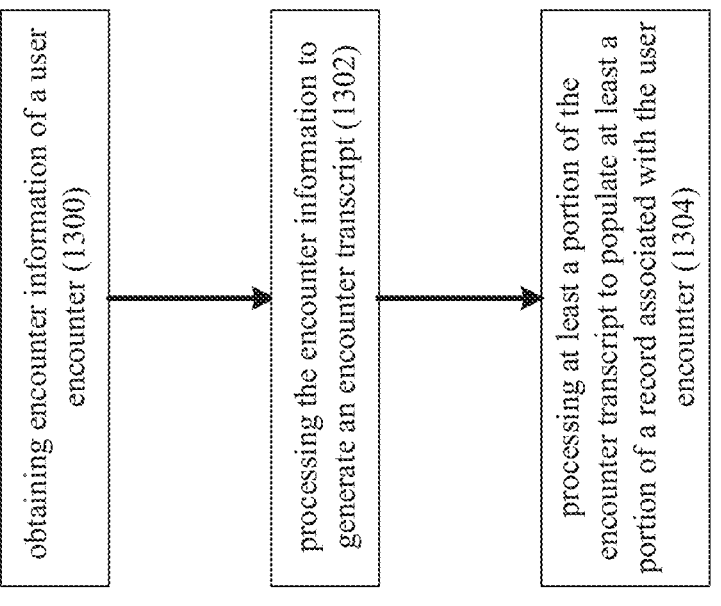
FIG. 25 is a flow chart of another implementation of the automated clinical documentation process of FIG. 1.

Referring also to FIG. 25 and as discussed above, automated clinical documentation process 10 may be configured to obtain 1300 encounter information (e.g., machine vision encounter information 102 and/or audio encounter information 106) of a user encounter.

This user encounter may include one or more of: a financial encounter; a life coach encounter; a legal encounter; a telecom encounter; a retail encounter; and a business encounter, wherein the encounter information (e.g., machine vision encounter information 102 and/or audio encounter information 106) may include one or more of: financial information; life coach information; legal information; telecom information; retail information; and business information.

As discussed above, the encounter information (e.g., machine vision encounter information 102 and/or audio encounter information 106) may be processed 1302 to generate an encounter transcript (e.g., encounter transcript 234). At least a portion of the encounter transcript (e.g., encounter transcript 234) may be processed 1304 to populate at least a portion of a record associated with the user encounter. Examples of such a record may include but are not limited to a financial record; a legal record; a telecom record; a retail record; and a business record.

Concept #2

As discussed above, automated clinical documentation process 10 may be executed within one or more of: a financial environment; a life coach environment; a legal environment; a telecom environment; a retail environment; and a business environment.

Figure 26:
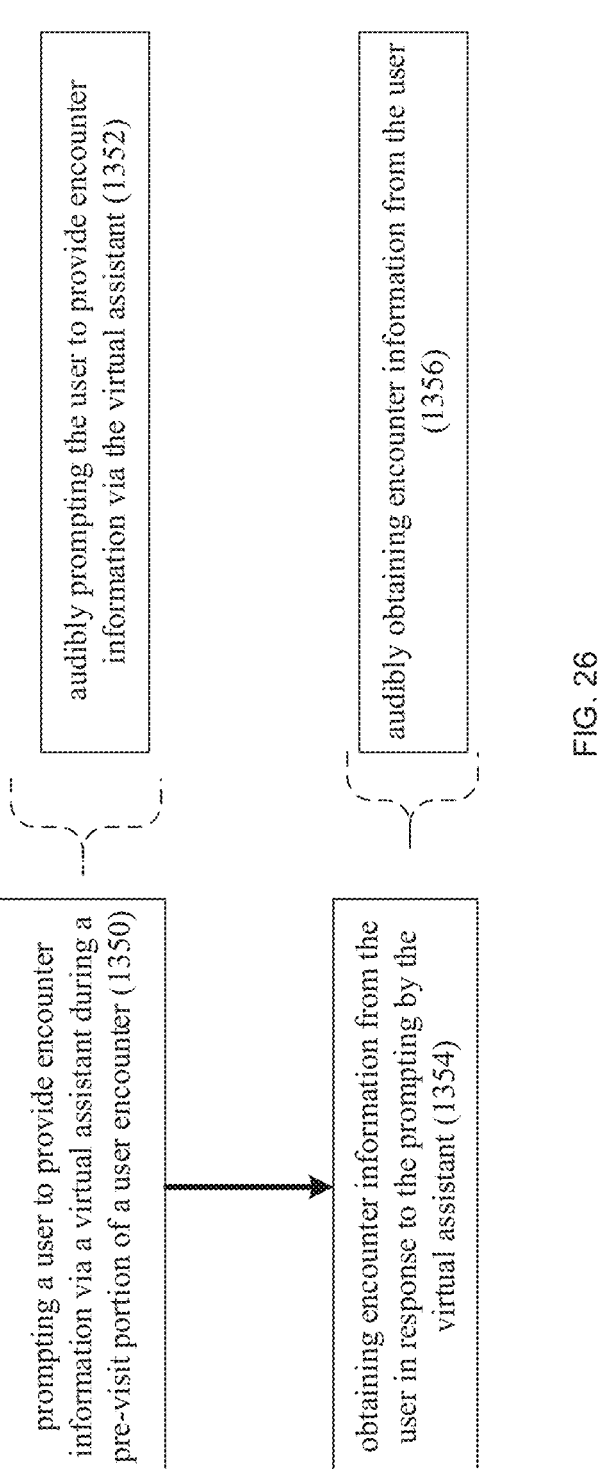
FIG. 26 is a flow chart of another implementation of the automated clinical documentation process of FIG. 1.

Referring also to FIG. 26 and as discussed above, automated clinical documentation process 10 may be configured to automate an intake process and may include prompting 1350 a user to provide encounter information (e.g., machine vision encounter information 102 and/or audio encounter information 106) via a virtual assistant (e.g., virtual assistant 238) during a pre-visit portion of a user encounter. Examples of such a user may include but are not limited to: a financial user; a legal user; a telecom user; a retail user; and a business user. Prompting 1350 a user to provide encounter information (e.g., machine vision encounter information 102 and/or audio encounter information 106) via a virtual assistant (e.g., virtual assistant 238) during a pre-visit portion of a user encounter may include audibly prompting 1352 a user to provide encounter information (e.g., machine vision encounter information 102 and/or audio encounter information 106) via a virtual assistant (e.g., virtual assistant 238) during a pre-visit portion of a user encounter This user encounter may include one or more of: a financial encounter; a life coach encounter; a legal encounter; a telecom encounter; a retail encounter; and a business encounter, wherein the encounter information (e.g., machine vision encounter information 102 and/or audio encounter information 106) may include one or more of: financial information; life coach information; legal information; telecom information; retail information; and business information.

As discussed above, the encounter information (e.g., machine vision encounter information 102 and/or audio encounter information 106) may be obtained 1354 from the user in response to the prompting by the virtual assistant (e.g., virtual assistant 238). Obtaining 1354 the encounter information from the user in response to the prompting by the virtual assistant (e.g., virtual assistant 238) may include audibly obtaining 1356 the encounter information (e.g., machine vision encounter information 102 and/or audio encounter information 106) from the user.

Concept #3

As discussed above, automated clinical documentation process 10 may be executed within one or more of: a financial environment; a life coach environment; a legal environment; a telecom environment; a retail environment; and a business environment.

Figure 27:
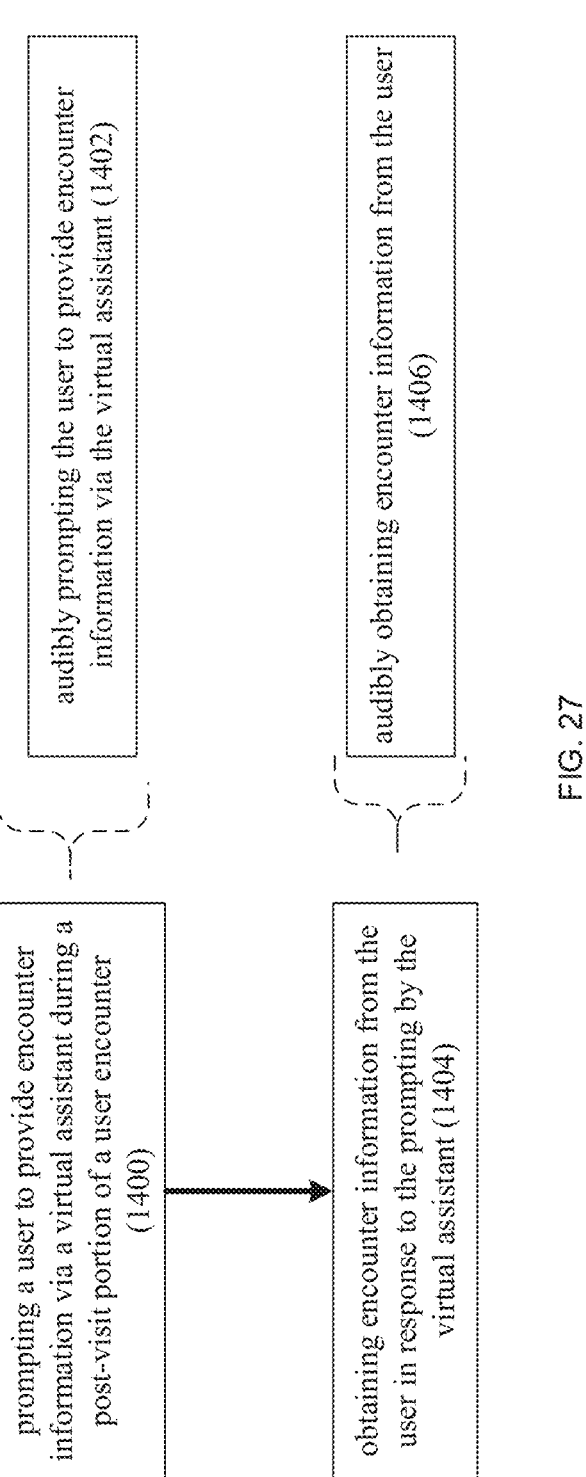
FIG. 27 is a flow chart of another implementation of the automated clinical documentation process of FIG. 1.

Referring also to FIG. 27 and as discussed above, automated clinical documentation process 10 may be configured to automate a follow-up process and may include prompting 1400 a user to provide encounter information (e.g., machine vision encounter information 102 and/or audio encounter information 106) via a virtual assistant (e.g., virtual assistant 238) during a post-visit portion of a user encounter. Examples of such a user may include but are not limited to: a financial user; a legal user; a telecom user; a retail user; and a business user. Prompting 1400 a user to provide encounter information (e.g., machine vision encounter information 102 and/or audio encounter information 106) via a virtual assistant (e.g., virtual assistant 238) during a post-visit portion of a user encounter may include audibly prompting 1402 a user to provide encounter information (e.g., machine vision encounter information 102 and/or audio encounter information 106) via a virtual assistant (e.g., virtual assistant 238) during a post-visit portion of a user encounter.

This user encounter may include one or more of: a financial encounter; a life coach encounter; a legal encounter; a telecom encounter; a retail encounter; and a business encounter, wherein the encounter information (e.g., machine vision encounter information 102 and/or audio encounter information 106) may include one or more of: financial information; life coach information; legal information; telecom information; retail information; and business information.

As discussed above, the encounter information (e.g., machine vision encounter information 102 and/or audio encounter information 106) may be obtained 1404 from the user in response to the prompting by the virtual assistant (e.g., virtual assistant 238). Obtaining 1404 the encounter information from the user in response to the prompting by the virtual assistant (e.g., virtual assistant 238) may include audibly obtaining 1406 the encounter information (e.g., machine vision encounter information 102 and/or audio encounter information 106) from the user.

Concept #4

As discussed above, automated clinical documentation process 10 may be executed within one or more of: a financial environment; a life coach environment; a legal environment; a telecom environment; a retail environment; and a business environment.

Figure 28:
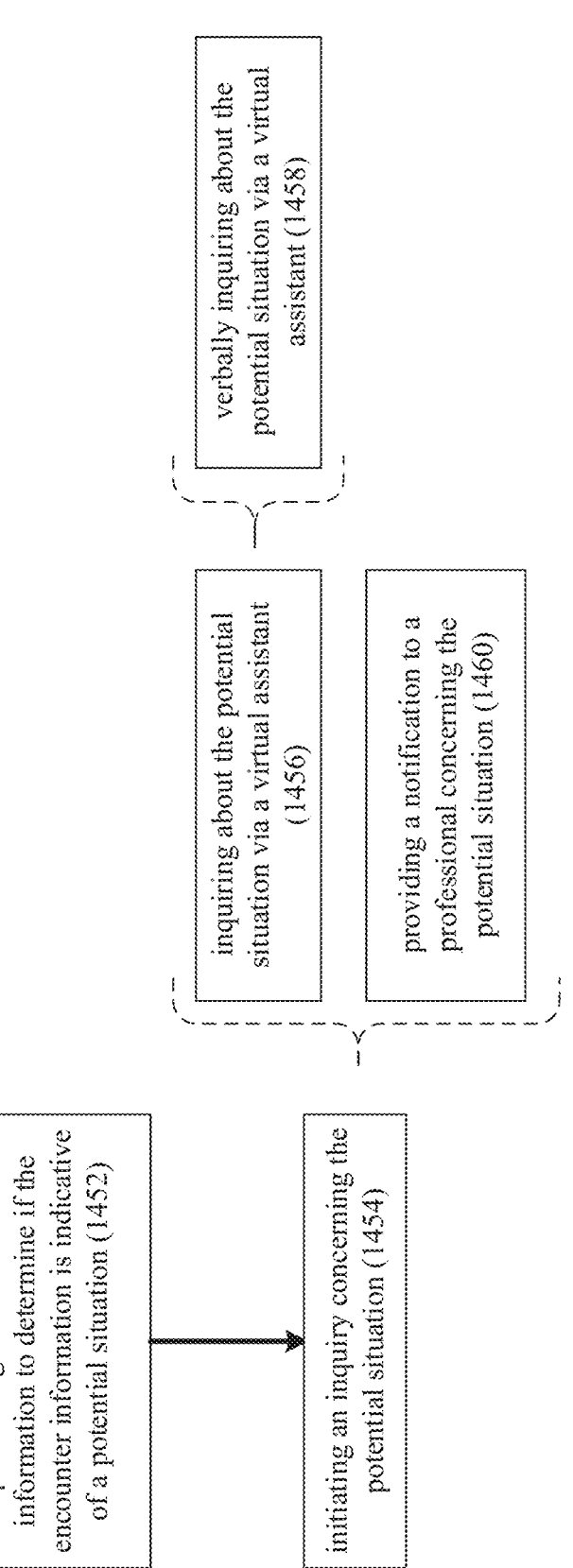
FIG. 28 is a flow chart of another implementation of the automated clinical documentation process of FIG. 1.

Referring also to FIG. 28 and as discussed above, automated clinical documentation process 10 may be configured to automate a monitoring process and may include obtaining 1450 encounter information (e.g., machine vision encounter information 102 and/or audio encounter information 106) of a user encounter.

This user encounter may include one or more of: a financial encounter; a life coach encounter; a legal encounter; a telecom encounter; a retail encounter; and a business encounter, wherein the encounter information (e.g., machine vision encounter information 102 and/or audio encounter information 106) may include one or more of: financial information; life coach information; legal information; telecom information; retail information; and business information.

As discussed above, the encounter information (e.g., machine vision encounter information 102 and/or audio encounter information 106) may be processed 1452 to determine if the encounter information (e.g., machine vision encounter information 102 and/or audio encounter information 106) is indicative of a potential situation. An inquiry may be initiated 1454 concerning the potential situation. Initiating 1454 an inquiry concerning the potential situation may include inquiring 1456 about the potential situation via a virtual assistant (e.g., virtual assistant 238), wherein inquiring 1456 about the potential situation via a virtual assistant (e.g., virtual assistant 238) may include verbally inquiring 1458 about the potential situation via a virtual assistant (e.g., virtual assistant 238). Initiating 1454 an inquiry concerning the potential situation may include providing 1460 a notification to a professional concerning the potential situation.

Concept #5

As discussed above, automated clinical documentation process 10 may be executed within one or more of: a financial environment; a life coach environment; a legal environment; a telecom environment; a retail environment; and a business environment.

Figure 29:
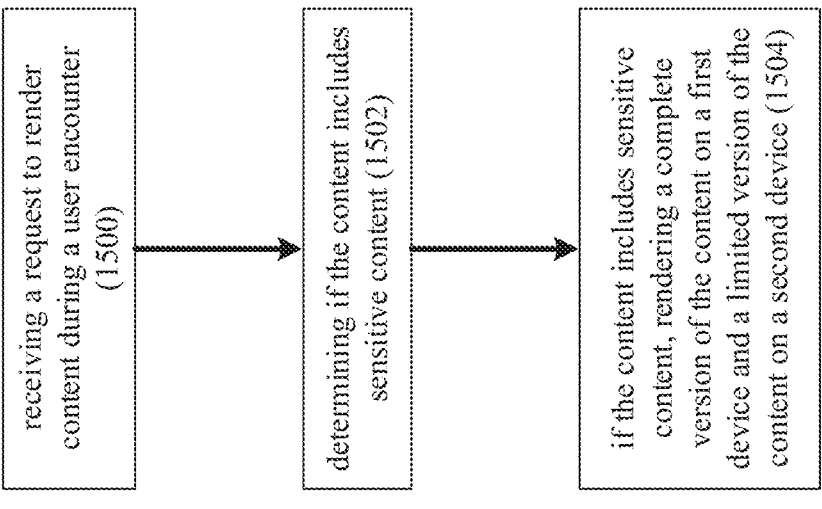
FIG. 29 is a flow chart of another implementation of the automated clinical documentation process of FIG. 1.

Referring also to FIG. 29 and as discussed above, automated clinical documentation process 10 may be configured to render content and may include receiving 1500 a request to render content during a user encounter.

This user encounter may include one or more of: a financial encounter; a life coach encounter; a legal encounter; a telecom encounter; a retail encounter; and a business encounter, wherein the encounter information (e.g., machine vision encounter information 102 and/or audio encounter information 106) may include one or more of: financial information; life coach information; legal information; telecom information; retail information; and business information. The content rendered may include financial content; life coach content; legal content; telecom content; retail content; and business content As discussed above, if it is determined 1502 that the content includes sensitive content, a complete version of the content may be rendered 1504 on a first device (wherein the complete version of the content includes the sensitive content) and a limited version of the content may be rendered on a second device (wherein the limited version of the content excludes the sensitive content).

Concept #6

As discussed above, automated clinical documentation process 10 may be executed within one or more of: a financial environment; a life coach environment; a legal environment; a telecom environment; a retail environment; and a business environment.

Referring again to FIG. 2, a modular ACD system 54 may be configured to automate clinical documentation and may include a machine vision system (e.g., machine vision system 100) configured to obtain machine vision encounter information (e.g., machine vision encounter information 102) concerning a user encounter.

The machine vision system (e.g., machine vision system 100) may include one or more of: an RGB imaging system; an infrared imaging system; an ultraviolet imaging system; a laser imaging system; an X-ray imaging system; a SONAR imaging system; a RADAR imaging system; and a thermal imaging system.

This user encounter may include one or more of: a financial encounter; a life coach encounter; a legal encounter; a telecom encounter; a retail encounter; and a business encounter, wherein the encounter information (e.g., machine vision encounter information 102 and/or audio encounter information 106) may include one or more of: financial information; life coach information; legal information; telecom information; retail information; and business information.

As discussed above, an audio recording system (e.g., audio recording system 104) may be configured to obtain audio encounter information (e.g., audio encounter information 106) concerning the user encounter. The audio recording system (e.g., audio recording system 104) may include: a directional microphone array (e.g., directional microphone array 200) that includes a plurality of discrete microphone assemblies (e.g., audio acquisition devices 202, 204, 206, 208, 210, 212, 214, 216, 218).

The modular ACD system (e.g., modular ACD system 54) may be configured to form one or more audio recording beams (e.g., audio recording beams 220, 222, 224) via the discrete audio acquisition devices (e.g., audio acquisition devices 202, 204, 206, 208, 210, 212, 214, 216, 218) included within the audio recording system (e.g., audio recording system 104).

A compute system (e.g., ACD compute system 12) may be configured to receive the machine vision encounter information (e.g., machine vision encounter information 102) and the audio encounter information (e.g., audio encounter information 106).

Concept #7

As discussed above, automated clinical documentation process 10 may be executed within one or more of: a financial environment; a life coach environment; a legal environment; a telecom environment; a retail environment; and a business environment.

Referring also to FIG. 30 and as discussed above, automated clinical documentation process 10 may be configured to automate diarization and may include obtaining 1550 encounter information (e.g., machine vision encounter information 102 and/or audio encounter information 106) of a user encounter.

This user encounter may include one or more of: a financial encounter; a life coach encounter; a legal encounter; a telecom encounter; a retail encounter; and a business encounter, wherein the encounter information (e.g., machine vision encounter information 102 and/or audio encounter information 106) may include one or more of: financial information; life coach information; legal information; telecom information; retail information; and business information.

As discussed above, the encounter information (e.g., machine vision encounter information 102 and/or audio encounter information 106) may be processed 1552 to: associate a first portion of the encounter information with a first encounter participant, and associate at least a second portion of the encounter information with at least a second encounter participant. An encounter transcript (e.g., encounter transcript 234) may be generated 1554 based, at least in part, upon the first portion of the encounter information and the at least a second portion of the encounter information.

Concept #8

As discussed above, automated clinical documentation process 10 may be executed within one or more of: a financial environment; a life coach environment; a legal environment; a telecom environment; a retail environment; and a business environment.

Referring also to FIG. 31 and as discussed above, automated clinical documentation process 10 may be configured to automate role assignment and may include obtaining 1600 encounter information (e.g., machine vision encounter information 102 and/or audio encounter information 106) of a user encounter.

This user encounter may include one or more of: a financial encounter; a life coach encounter; a legal encounter; a telecom encounter; a retail encounter; and a business encounter, wherein the encounter information (e.g., machine vision encounter information 102 and/or audio encounter information 106) may include one or more of: financial information; life coach information; legal information; telecom information; retail information; and business information.

As discussed above, the encounter information (e.g., machine vision encounter information 102 and/or audio encounter information 106) may be processed 1602 to associate a first portion of the encounter information (e.g., machine vision encounter information 102 and/or audio encounter information 106) with a first encounter participant. Processing 1602 the encounter information (e.g., machine vision encounter information 102 and/or audio encounter information 106) to associate a first portion of the encounter information (e.g., machine vision encounter information 102 and/or audio encounter information 106) with a first encounter participant may include processing 1604 the encounter information (e.g., machine vision encounter information 102 and/or audio encounter information 106) to associate a first portion of the machine vision encounter information (e.g., machine vision encounter information 102) with the first encounter participant. A first role may be assigned 1606 to the first encounter participant.

Concept #9

As discussed above, automated clinical documentation process 10 may be executed within one or more of: a financial environment; a life coach environment; a legal environment; a telecom environment; a retail environment; and a business environment.

Figure 32:
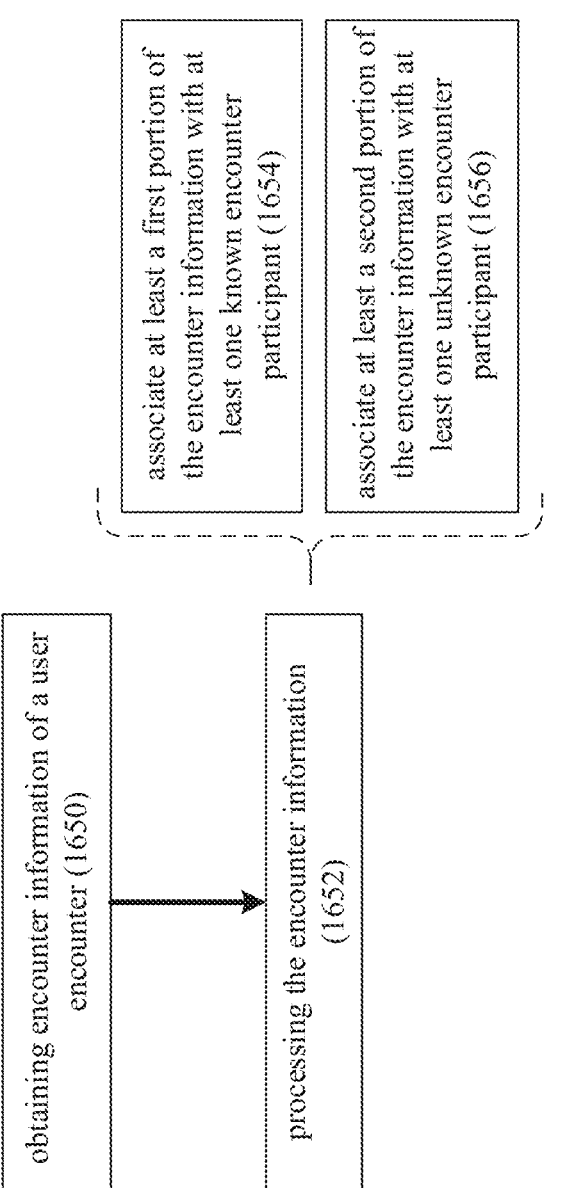
FIG. 32 is a flow chart of another implementation of the automated clinical documentation process of FIG. 1.

Referring also to FIG. 32 and as discussed above, automated clinical documentation process 10 may be configured to monitor a plurality of encounter participants and may include obtaining 1650 encounter information (e.g., machine vision encounter information 102 and/or audio encounter information 106) of a user encounter.

This user encounter may include one or more of: a financial encounter; a life coach encounter; a legal encounter; a telecom encounter; a retail encounter; and a business encounter, wherein the encounter information (e.g., machine vision encounter information 102 and/or audio encounter information 106) may include one or more of: financial information; life coach information; legal information; telecom information; retail information; and business information.

As discussed above, the encounter information (e.g., machine vision encounter information 102 and/or audio encounter information 106) may be processed 1652 to: associate 1654 at least a first portion of the encounter information (e.g., machine vision encounter information 102 and/or audio encounter information 106) with at least one known encounter participant, and associate 1656 at least a second portion of the encounter information (e.g., machine vision encounter information 102 and/or audio encounter information 106) with at least one unknown encounter participant.

Concept #10

As discussed above, automated clinical documentation process 10 may be executed within one or more of: a financial environment; a life coach environment; a legal environment; a telecom environment; a retail environment; and a business environment.

Figure 33:
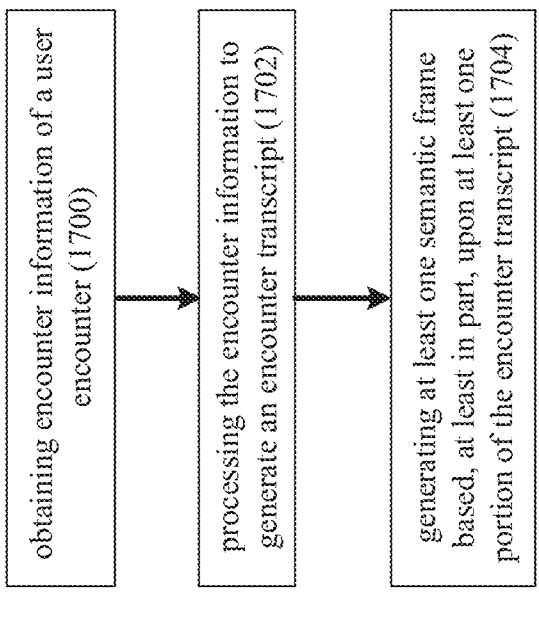
FIG. 33 is a flow chart of another implementation of the automated clinical documentation process of FIG. 1.

Referring also to FIG. 33 and as discussed above, automated clinical documentation process 10 may be configured to populate records via semantic frames and may include obtaining 1700 encounter information (e.g., machine vision encounter information 102 and/or audio encounter information 106) of a user encounter. Examples of such a records may include but are not limited to a financial records; a legal records; a telecom records; a retail records; and a business records.

This user encounter may include one or more of: a financial encounter; a life coach encounter; a legal encounter; a telecom encounter; a retail encounter; and a business encounter, wherein the encounter information (e.g., machine vision encounter information 102 and/or audio encounter information 106) may include one or more of: financial information; life coach information; legal information; telecom information; retail information; and business information.

As discussed above, the encounter information (e.g., machine vision encounter information 102 and/or audio encounter information 106) may be processed 1702 to generate an encounter transcript (e.g., encounter transcript 234). At least one semantic frame may be generated 1704 based, at least in part, upon at least one portion of the encounter transcript (e.g., encounter transcript 234), wherein the at least one semantic frame may define an abstract meaning for the at least one portion of the encounter transcript (e.g., encounter transcript 234).

Concept #11

As discussed above, automated clinical documentation process 10 may be executed within one or more of: a financial environment; a life coach environment; a legal environment; a telecom environment; a retail environment; and a business environment.

Referring again to FIG. 2, a mixed-media ACD device (e.g., mixed-media ACD device 232) may be configured to monitor one or more encounter participants of a user encounter and may include a machine vision system (e.g., machine vision system 100) configured to obtain machine vision encounter information (e.g., machine vision encounter information 102) concerning the user encounter. The mixed-media ACD device (e.g., mixed-media ACD device 232) may be configured to monitor a monitored space (e.g., monitored space 130) in a clinical environment.

The machine vision system (e.g., machine vision system 100) may include one or more of: an RGB imaging system; an infrared imaging system; an ultraviolet imaging system; a laser imaging system; an X-ray imaging system; a SONAR imaging system; a RADAR imaging system; and a thermal imaging system.

This user encounter may include one or more of: a financial encounter; a life coach encounter; a legal encounter; a telecom encounter; a retail encounter; and a business encounter, wherein the encounter information (e.g., machine vision encounter information 102 and/or audio encounter information 106) may include one or more of: financial information; life coach information; legal information; telecom information; retail information; and business information.

As discussed above, an audio recording system (e.g., audio recording system 104) may be configured to obtain audio encounter information (e.g., audio encounter information 106) concerning the user encounter, wherein the audio recording system (e.g., audio recording system 104) may include a plurality of discrete audio acquisition devices (e.g., audio acquisition devices 202, 204, 206, 208, 210, 212, 214, 216, 218 of FIG. 3).

Concept #12

As discussed above, automated clinical documentation process 10 may be executed within one or more of: a financial environment; a life coach environment; a legal environment; a telecom environment; a retail environment; and a business environment.

Figure 34:
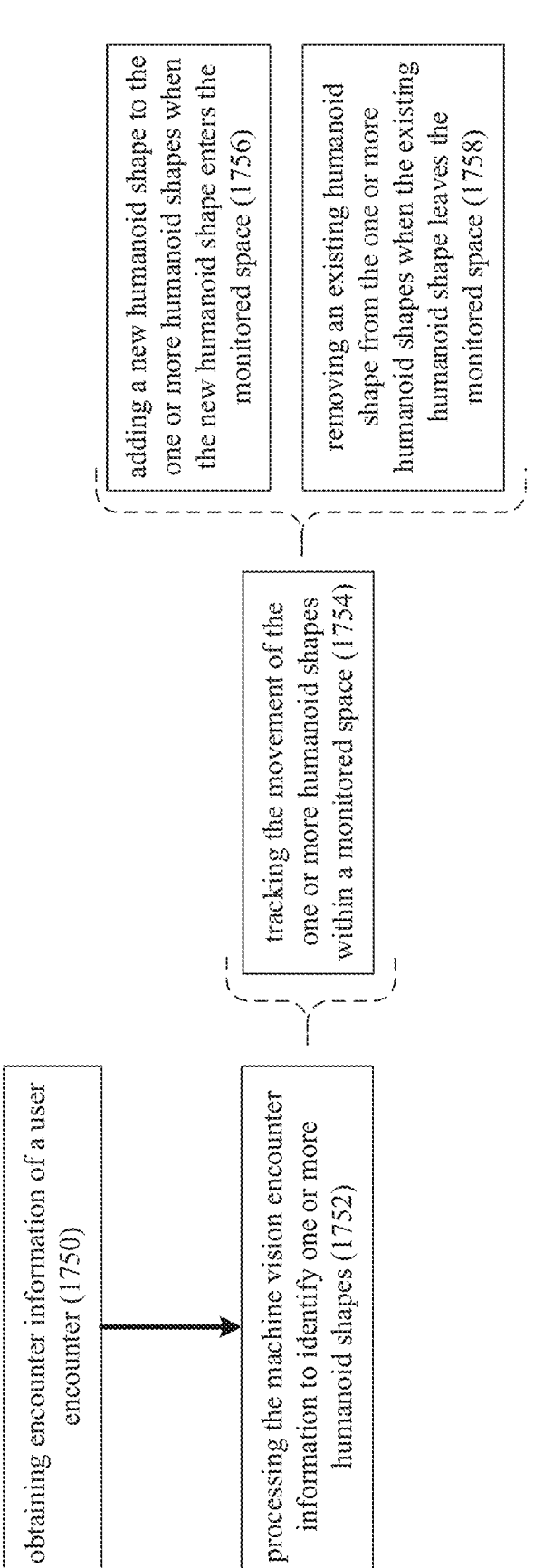
FIG. 34 is a flow chart of another implementation of the automated clinical documentation process of FIG. 1.

Referring also to FIG. 34 and as discussed above, automated clinical documentation process 10 may be configured to track encounter participants and may include obtaining 1750 encounter information (e.g., machine vision encounter information 102 and/or audio encounter information 106) of a user encounter, wherein the encounter information (e.g., machine vision encounter information 102 and/or audio encounter information 106) may include machine vision encounter information (e.g., machine vision encounter information 102) obtained via one or more machine vision systems (e.g., machine vision system 100).

This user encounter may include one or more of: a financial encounter; a life coach encounter; a legal encounter; a telecom encounter; a retail encounter; and a business encounter, wherein the encounter information (e.g., machine vision encounter information 102 and/or audio encounter information 106) may include one or more of: financial information; life coach information; legal information; telecom information; retail information; and business information.

As discussed above, the machine vision encounter information (e.g., machine vision encounter information 102) may be processed 1752 to identify one or more humanoid shapes. Processing 1752 the machine vision encounter information (e.g., machine vision encounter information 102) to identify one or more humanoid shapes may include: tracking 1754 the movement of the one or more humanoid shapes within a monitored space (e.g., monitored space 130).

Tracking 1754 the movement of the one or more humanoid shapes within the monitored space (e.g., monitored space 130) may include: adding 1756 a new humanoid shape to the one or more humanoid shapes when the new humanoid shape enters the monitored space (e.g., monitored space 130) and/or removing 1758 an existing humanoid shape from the one or more humanoid shapes when the existing humanoid shape leaves the monitored space (e.g., monitored space 130).

Concept #13

As discussed above, automated clinical documentation process 10 may be executed within one or more of: a financial environment; a life coach environment; a legal environment; a telecom environment; a retail environment; and a business environment.

Figure 35:
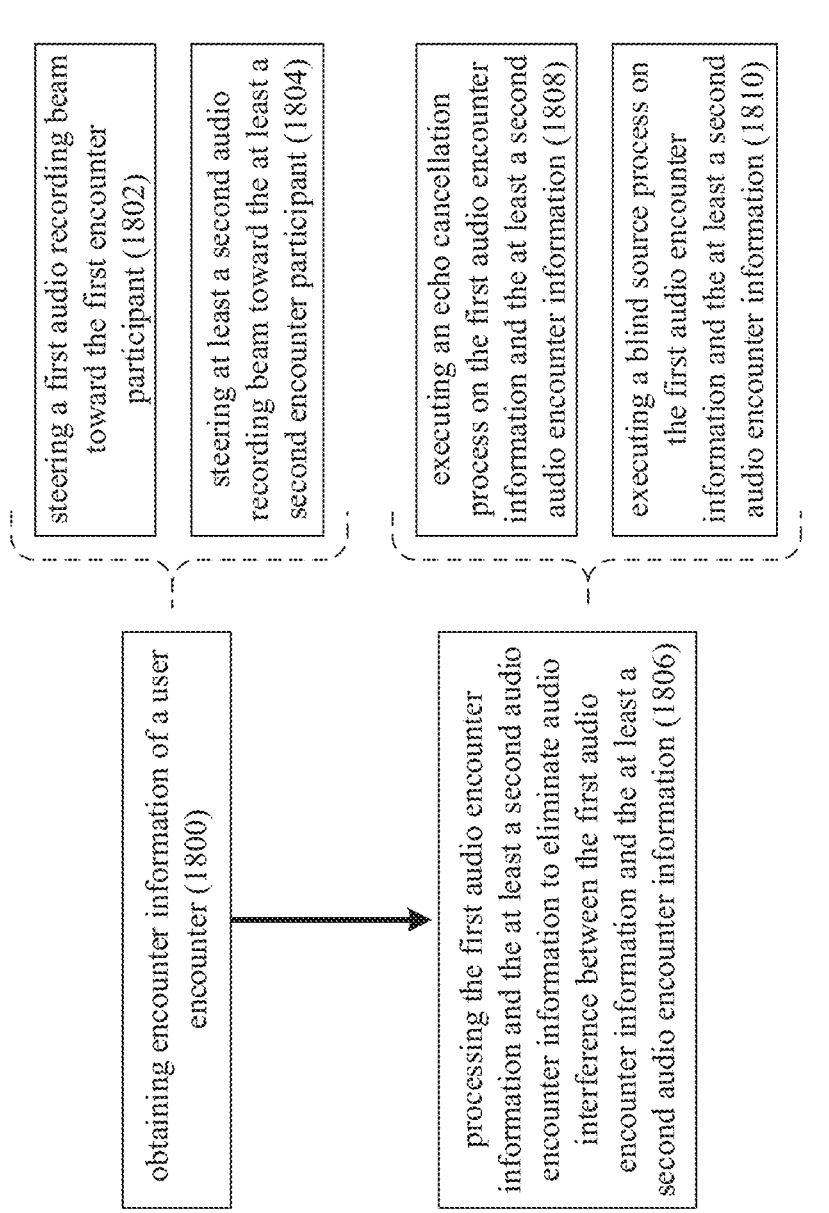
FIG. 35 is a flow chart of another implementation of the automated clinical documentation process of FIG. 1.

Referring also to FIG. 35 and as discussed above, automated clinical documentation process 10 may be configured to effectuate source separation and may include obtaining 1800 encounter information (e.g., machine vision encounter information 102 and/or audio encounter information 106) of a user encounter, wherein the encounter information (e.g., machine vision encounter information 102 and/or audio encounter information 106) may include first audio encounter information obtained from a first encounter participant and at least second audio encounter information obtained from at least a second encounter participant.

This user encounter may include one or more of: a financial encounter; a life coach encounter; a legal encounter; a telecom encounter; a retail encounter; and a business encounter, wherein the encounter information (e.g., machine vision encounter information 102 and/or audio encounter information 106) may include one or more of: financial information; life coach information; legal information; telecom information; retail information; and business information.

Obtaining 1800 the encounter information (e.g., machine vision encounter information 102 and/or audio encounter information 106) of a user encounter may include: steering 1802 a first audio recording beam toward the first encounter participant; and steering 1804 at least a second audio recording beam toward the at least a second encounter participant.

As discussed above, the first audio encounter information and the at least second audio encounter information may be processed 1806 to eliminate audio interference between the first audio encounter information and the at least second audio encounter information.

Processing 1806 the first audio encounter information and the at least a second audio encounter information to eliminate audio interference may include: executing 1808 an echo cancellation process on the first audio encounter information and the at least a second audio encounter information and/or executing 1810 a blind source process on the first audio encounter information and the at least a second audio encounter information.

Concept #14

As discussed above, automated clinical documentation process 10 may be executed within one or more of: a financial environment; a life coach environment; a legal environment; a telecom environment; a retail environment; and a business environment.

Figure 36:
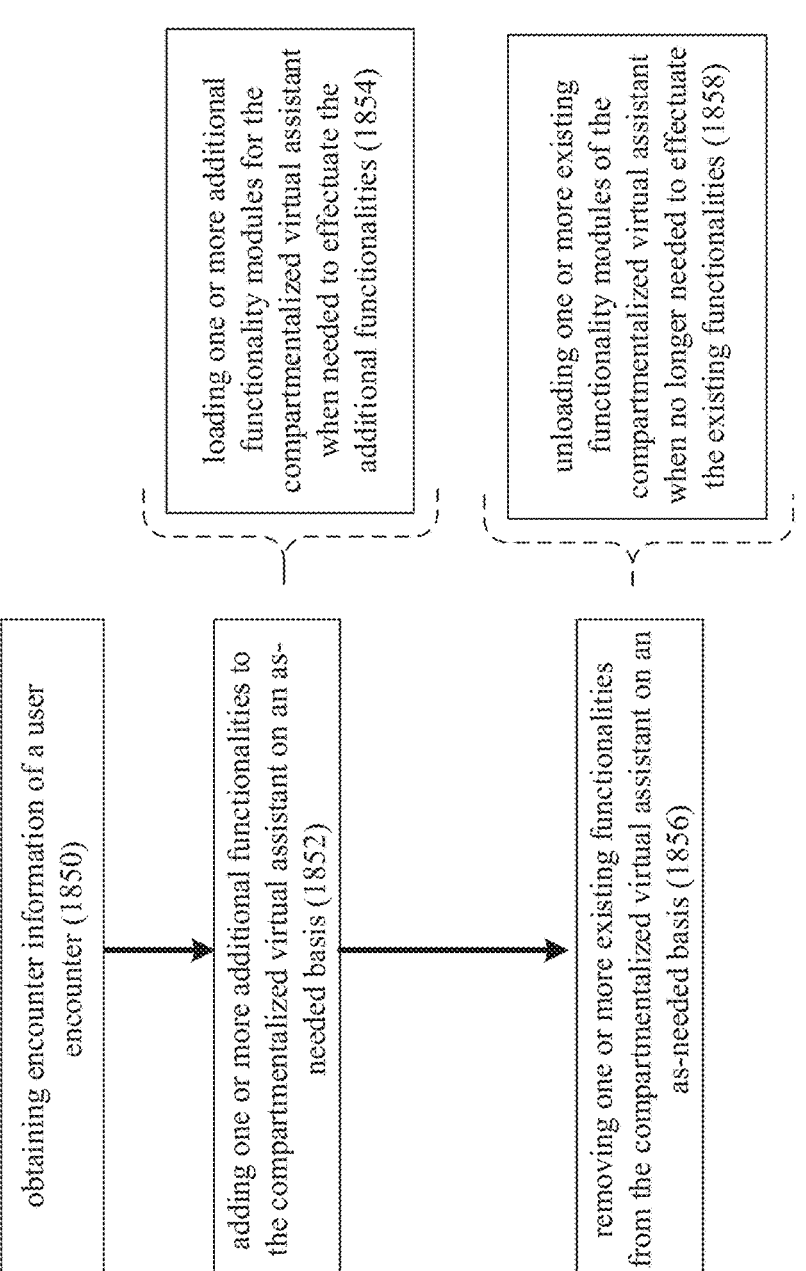
FIG. 36 is a flow chart of another implementation of the automated clinical documentation process of FIG. 1.

Referring also to FIG. 36 and as discussed above, automated clinical documentation process 10 may be configured to compartmentalize a virtual assistant (e.g., virtual assistant 238) and may include obtaining 1850 encounter information (e.g., machine vision encounter information 102 and/or audio encounter information 106) via a compartmentalized virtual assistant (e.g., virtual assistant 238) during a user encounter, wherein the compartmentalized virtual assistant (e.g., virtual assistant 238) may include a core functionality module.

This user encounter may include one or more of: a financial encounter; a life coach encounter; a legal encounter; a telecom encounter; a retail encounter; and a business encounter, wherein the encounter information (e.g., machine vision encounter information 102 and/or audio encounter information 106) may include one or more of: financial information; life coach information; legal information; telecom information; retail information; and business information.

As discussed above, one or more additional functionalities may be added 1852 to the compartmentalized virtual assistant (e.g., virtual assistant 238) on an as-needed basis. Adding 1852 one or more additional functionalities to the compartmentalized virtual assistant (e.g., virtual assistant 238) on an as-needed basis may include: loading 1854 one or more additional functionality modules (e.g., functionality module 246) for the compartmentalized virtual assistant (e.g., virtual assistant 238) when needed to effectuate the additional functionalities.

Further, one or more existing functionalities may be removed 1856 from the compartmentalized virtual assistant (e.g., virtual assistant 238) on an as-needed basis. Removing 1856 one or more existing functionalities from the compartmentalized virtual assistant (e.g., virtual assistant 238) on an as-needed basis may include: unloading 1858 one or more existing functionality modules (e.g., functionality module 248) of the compartmentalized virtual assistant (e.g., virtual assistant 238) when no longer needed to effectuate the existing functionalities.

Concept #15

As discussed above, automated clinical documentation process 10 may be executed within one or more of: a financial environment; a life coach environment; a legal environment; a telecom environment; a retail environment; and a business environment.

Referring also to FIG. 37 and as discussed above, automated clinical documentation process 10 may be configured to effectuate functionality module communication and may include obtaining 1900 encounter information (e.g., machine vision encounter information 102 and/or audio encounter information 106) via a compartmentalized virtual assistant (e.g., virtual assistant 238) during a user encounter, wherein the compartmentalized virtual assistant (e.g., virtual assistant 238) may include a plurality of functionality modules.

This user encounter may include one or more of: a financial encounter; a life coach encounter; a legal encounter; a telecom encounter; a retail encounter; and a business encounter, wherein the encounter information (e.g., machine vision encounter information 102 and/or audio encounter information 106) may include one or more of: financial information; life coach information; legal information; telecom information; retail information; and business information.

Obtaining 1900 encounter information (e.g., machine vision encounter information 102 and/or audio encounter information 106) via a compartmentalized virtual assistant (e.g., virtual assistant 238) during a user encounter may include audibly obtaining 1902 encounter information (e.g., machine vision encounter information 102 and/or audio encounter information 106) via the compartmentalized virtual assistant (e.g., virtual assistant 238) during the user encounter.

As discussed above, at least a portion of the encounter information (e.g., machine vision encounter information 102 and/or audio encounter information 106) may be processed 1904 via a first functionality module of the plurality of functionality modules to generate a first result. The first result may be provided 1906 to a second functionality module of the plurality of functionality modules. The first result set may be processed 1908 via the second functionality module to generate a second result.

Concept #16

As discussed above, automated clinical documentation process 10 may be executed within one or more of: a financial environment; a life coach environment; a legal environment; a telecom environment; a retail environment; and a business environment.

Figure 38:
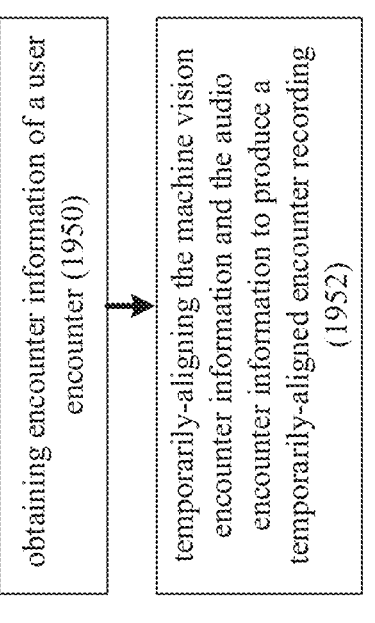
FIG. 38 is a flow chart of another implementation of the automated clinical documentation process of FIG. 1.

Referring also to FIG. 38 and as discussed above, automated clinical documentation process 10 may be configured to synchronize machine vision and audio and may include obtaining 1950 encounter information (e.g., machine vision encounter information 102 and/or audio encounter information 106) of a user encounter, wherein the encounter information (e.g., machine vision encounter information 102 and/or audio encounter information 106) may include machine vision encounter information (e.g., machine vision encounter information 102) and audio encounter information (e.g., audio encounter information 106).

This user encounter may include one or more of: a financial encounter; a life coach encounter; a legal encounter; a telecom encounter; a retail encounter; and a business encounter, wherein the encounter information (e.g., machine vision encounter information 102 and/or audio encounter information 106) may include one or more of: financial information; life coach information; legal information; telecom information; retail information; and business information.

As discussed above, the machine vision encounter information (e.g., machine vision encounter information 102) and the audio encounter information (e.g., audio encounter information 106) may be temporally-aligned to 1952 produce a temporarily-aligned encounter recording.

Concept #17

As discussed above, automated clinical documentation process 10 may be executed within one or more of: a financial environment; a life coach environment; a legal environment; a telecom environment; a retail environment; and a business environment.

Referring also to FIG. 39 and as discussed above, automated clinical documentation process 10 may be configured to effectuate visual diarization of a user encounter and may include obtaining 2000 encounter information (e.g., machine vision encounter information 102 and/or audio encounter information 106) of the user encounter.

This user encounter may include one or more of: a financial encounter; a life coach encounter; a legal encounter; a telecom encounter; a retail encounter; and a business encounter, wherein the encounter information may include one or more of: financial information; life coach information; legal information; telecom information; retail information; and business information.

As discussed above, the encounter information (e.g., machine vision encounter information 102 and/or audio encounter information 106) may be processed 2002 to: associate a first portion of the encounter information (e.g., machine vision encounter information 102 and/or audio encounter information 106) with a first encounter participant, and associate at least a second portion of the encounter information (e.g., machine vision encounter information 102 and/or audio encounter information 106) with at least a second encounter participant. A visual representation of the encounter information (e.g., machine vision encounter information 102 and/or audio encounter information 106) may be rendered 2004. A first visual representation of the first portion of the encounter information may be rendered 2006 that is temporally-aligned with the visual representation of the encounter information (e.g., machine vision encounter information 102 and/or audio encounter information 106). At least a second visual representation of the at least a second portion of the encounter information may be rendered 2008 that is temporally-aligned with the visual representation of the encounter information (e.g., machine vision encounter information 102 and/or audio encounter information 106).

Concept #18

As discussed above, automated clinical documentation process 10 may be executed within one or more of: a financial environment; a life coach environment; a legal environment; a telecom environment; a retail environment; and a business environment.

Referring also to FIG. 40 and as discussed above, automated clinical documentation process 10 may be configured to effectuate visual compartmentalization of a user encounter and may include obtaining 2050 encounter information (e.g., machine vision encounter information 102 and/or audio encounter information 106) of the user encounter.

This user encounter may include one or more of: a financial encounter; a life coach encounter; a legal encounter; a telecom encounter; a retail encounter; and a business encounter, wherein the encounter information (e.g., machine vision encounter information 102 and/or audio encounter information 106) may include one or more of: financial information; life coach information; legal information; telecom information; retail information; and business information.

As discussed above, the encounter information (e.g., machine vision encounter information 102 and/or audio encounter information 106) may be processed 2052 to: associate a first portion of the encounter information (e.g., machine vision encounter information 102 and/or audio encounter information 106) with a first encounter portion, and associate at least a second portion of the encounter information (e.g., machine vision encounter information 102 and/or audio encounter information 106) with at least a second encounter portion. A visual representation of the encounter information (e.g., machine vision encounter information 102 and/or audio encounter information 106) may be rendered 2054. A first visual representation of the first portion of the encounter information may be rendered 2056 that is temporally-aligned with the visual representation of the encounter information (e.g., machine vision encounter information 102 and/or audio encounter information 106). At least a second visual representation of the at least a second portion of the encounter information may be rendered 2058 that is temporally-aligned with the visual representation of the encounter information (e.g., machine vision encounter information 102 and/or audio encounter information 106).

Concept #19

Figure 41:
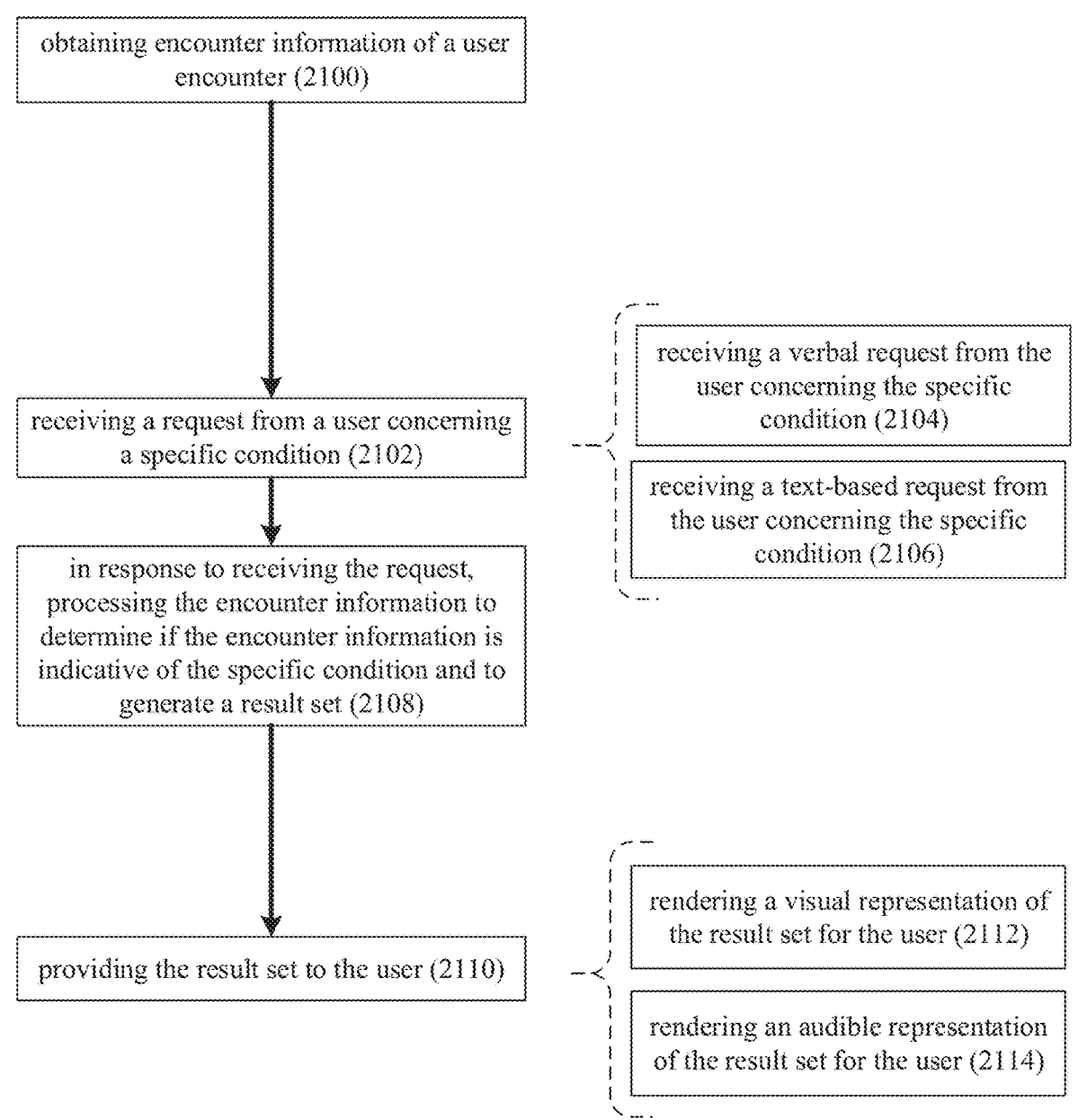
FIG. 41 is a flow chart of another implementation of the automated clinical documentation process of FIG. 1.

As discussed above, automated clinical documentation process 10 may be executed within one or more of: a financial environment; a life coach environment; a legal environment; a telecom environment; a retail environment; and a business environment. Referring also to FIG. 41 and as discussed above, automated clinical documentation process 10 may be configured to effectuate reactive encounter scanning and may include obtaining 2100 encounter information (e.g., machine vision encounter information 102 and/or audio encounter information 106) of a user encounter.

This user encounter may include one or more of: a financial encounter; a life coach encounter; a legal encounter; a telecom encounter; a retail encounter; and a business encounter, wherein the encounter information (e.g., machine vision encounter information 102 and/or audio encounter information 106) may include one or more of: financial information; life coach information; legal information; telecom information; retail information; and business information.

As discussed above, a request may be received 2102 from a user concerning a specific condition. Examples of such a user may include but are not limited to: a financial user; a legal user; a telecom user; a retail user; and a business user. Receiving 2102 a request from a user may include: receiving 2104 a verbal request from the user concerning the specific condition; and/or receiving 2106 a text-based request from the user concerning the specific condition.

In response to receiving the request, the encounter information (e.g., machine vision encounter information 102 and/or audio encounter information 106) may be processed 2108 to determine if the encounter information (e.g., machine vision encounter information 102 and/or audio encounter information 106) is indicative of the specific condition and to generate a result set.

The result set may be provided 2110 to the user. Providing 2110 the result set to the user may include: rendering 2112 a visual representation of the result set for the user and/or rendering 2114 an audible representation of the result set for the user.

Concept #20

Figure 42:
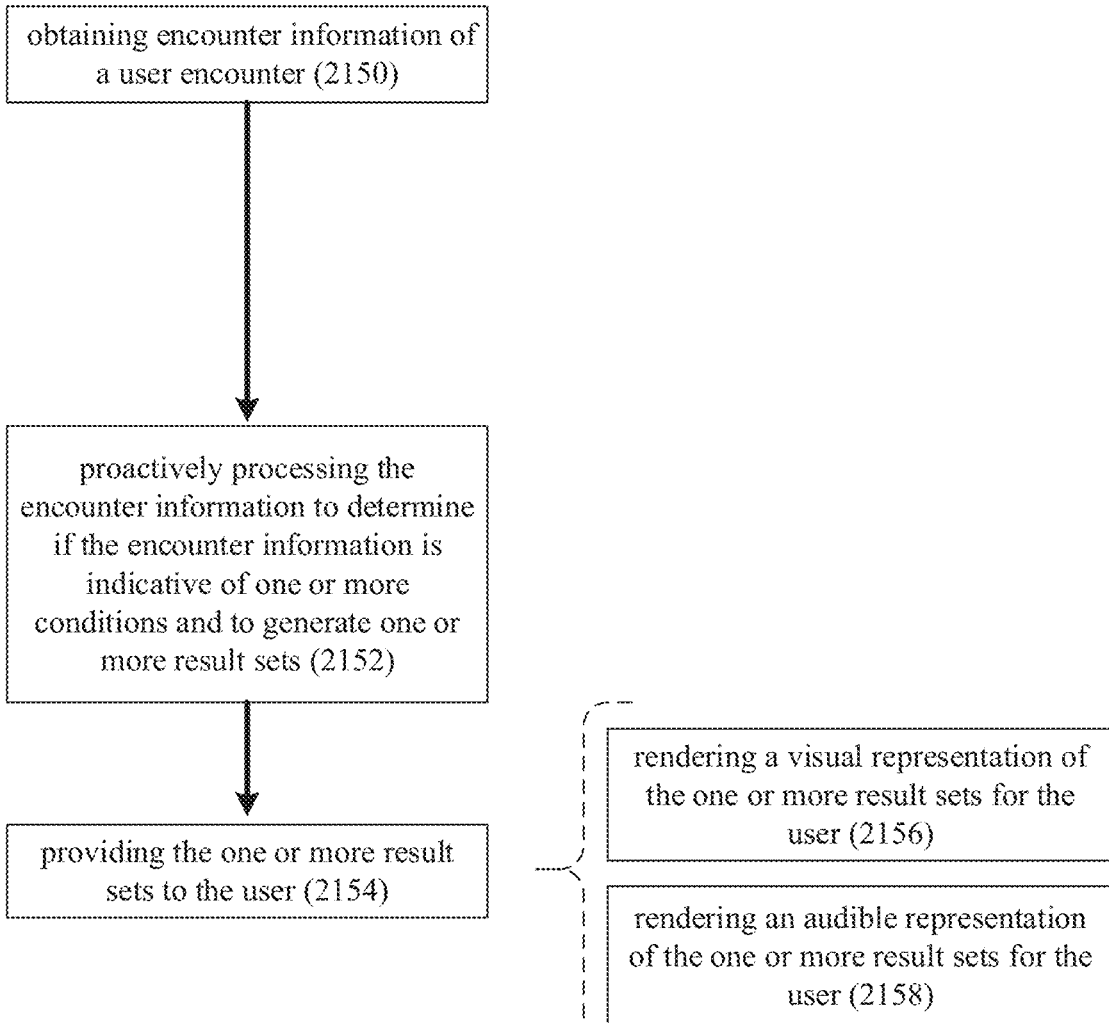
FIG. 42 is a flow chart of another implementation of the automated clinical documentation process of FIG. 1.

As discussed above, automated clinical documentation process 10 may be executed within one or more of: a financial environment; a life coach environment; a legal environment; a telecom environment; a retail environment; and a business environment. Referring also to FIG. 42 and as discussed above, automated clinical documentation process 10 may be configured to effectuate proactive encounter scanning device and may include obtaining 2150 encounter information (e.g., machine vision encounter information 102 and/or audio encounter information 106) of a user encounter.

This user encounter may include one or more of: a financial encounter; a life coach encounter; a legal encounter; a telecom encounter; a retail encounter; and a business encounter, wherein the encounter information (e.g., machine vision encounter information 102 and/or audio encounter information 106) may include one or more of: financial information; life coach information; legal information; telecom information; retail information; and business information.

As discussed above, the encounter information (e.g., machine vision encounter information 102 and/or audio encounter information 106) may be proactively processed 2152 to determine if the encounter information (e.g., machine vision encounter information 102 and/or audio encounter information 106) is indicative of one or more conditions and to generate one or more result sets. The one or more result sets may be provided 2154 to the user. Examples of such a user may include but are not limited to: a financial user; a legal user; a telecom user; a retail user; and a business user.

General:

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method comprising:

recording, by one or more machine vision devices of an automated clinical documentation (ACD) system, machine vision encounter information of a clinical encounter that includes a patient meeting with a participant in a clinical environment monitored by the ACD system, the one or more machine vision devices of the ACD system being deployed in the clinical environment;

recording, by one or more audio sensors of the ACD system, audio encounter information of the clinical encounter, the one or more audio sensors of the ACD system being deployed in the clinical environment, wherein the one or more audio sensors are not synchronized with the one or more machine vision devices such that the machine vision encounter information and the audio encounter information lack synchronization at the time of recording;

temporally-aligning the machine vision encounter information and the audio encounter information to produce a temporally-aligned encounter recording that synchronizes the machine vision encounter information with the audio encounter information;

generating, by the ACD system, a transcript of the clinical encounter based on the temporally-aligned encounter recording, wherein at least a portion of the transcript is generated by performing visual speech recognition on the synchronized machine vision encounter information;

proactively scanning, by the ACD system, the transcript based on a medical conditions symptoms datasource to identify indications of a specific medical condition, wherein the medical conditions symptoms datasource defines symptoms for various medical conditions;

sending, by the ACD system during the clinical encounter, a message to a participant of the clinical encounter responsive to determining that a number of the indications of the specific medical condition exceeds a threshold, the message recommending that the patient undergo testing for the specific medical condition; and displaying, via a display of the ACD system, a visual representation of the transcript, the visual representation of the transcript identifying portions of the transcript that indicate the specific medical condition.

2. The computer-implemented method of claim 1, wherein the one or more machine vision devices include at least one of:

an RGB imaging system;
an infrared imaging system;
an ultraviolet imaging system;
a laser imaging system;
an X-ray imaging system;
a SONAR imaging system;
a RADAR imaging system; or
a thermal imaging system.

3. The computer-implemented method of claim 1, wherein the message recommending that the patient undergo testing for the specific medical condition is a text message sent to an electronic device of the participant.

4. The computer-implemented method of claim 1, wherein the message recommending that the patient undergo testing for the specific medical condition is an audio message.

5. The computer-implemented method of claim 4, wherein the audio message is played through an earbud worn by the participant during the clinical encounter.

6. The computer-implemented method of claim 1, wherein the message recommending that the patient undergo testing for the specific medical condition is displayed via the display of the ACD system.

7. An automated clinical documentation (ACD) system comprising:

one or more machine vision devices configured to record machine vision encounter information of a clinical encounter that includes a patient meeting with a participant in a clinical environment monitored by the ACD system;

one or more audio sensors configured to record audio encounter information of the clinical encounter, the one or more audio sensors and the one or more machine vision devices of the ACD system being deployed in the clinical environment, wherein the one or more audio sensors are not synchronized with the one or more machine vision devices such that the machine vision encounter information and the audio encounter information lack synchronization at the time of recording, and wherein the machine vision encounter information and the audio encounter information are temporally aligned to produce a temporally-aligned encounter recording that synchronizes the machine vision encounter information with the audio encounter information;

at least one processor configured to generate a transcript of the clinical encounter based on the temporally-aligned encounter recording, wherein at least a portion of the transcript is generated by performing visual speech recognition on the synchronized machine vision encounter information, and wherein the at least one processor is further configured to proactively scan the transcript based on a medical conditions symptoms datasource to identify indications of a specific medical condition, wherein the medical conditions symptoms datasource defines symptoms for various medical conditions, and wherein the ACD system sends a message to a participant of the clinical encounter during the clinical encounter responsive to determining that a number of the indications of the specific medical condition exceeds a threshold, the message recommending that the patient undergo testing for the specific medical condition; and a display configured to display a visual representation of the transcript, the visual representation of the transcript identifying portions of the transcript that indicate the specific medical condition.

8. The ACD system of claim 7, wherein the one or more machine vision devices include at least one of:

an RGB imaging system;
an infrared imaging system;
an ultraviolet imaging system;
a laser imaging system;
an X-ray imaging system;
a SONAR imaging system;
a RADAR imaging system; or
a thermal imaging system.

9. The ACD system of claim 7, wherein the message recommending that the patient undergo testing for the specific medical condition is a text message sent to an electronic device of the participant.

10. The ACD system of claim 7, wherein the message recommending that the patient undergo testing for the specific medical condition is an audio message.

11. The ACD system of claim 10, wherein the audio message is played through an earbud worn by the participant during the clinical encounter.

12. The ACD system of claim 7, wherein the message recommending that the patient undergo testing for the specific medical condition is displayed via the display of the ACD system.

13. An automated clinical documentation (ACD) system comprising:

at least one processor; and a memory storing programming instructions for execution by the at least one processor, the programming instructions, upon execution by the at least one processor, causing the ACD system to perform the following operations:

recording, by one or more machine vision devices of the ACD system, machine vision encounter information of a clinical encounter that includes a patient meeting with a participant in a clinical environment monitored by the ACD system, the one or more machine vision devices of the ACD system being deployed in the clinical environment;

recording, by one or more audio sensors of the ACD system, audio encounter information of the clinical encounter, the one or more audio sensors of the ACD system being deployed in the clinical environment, wherein the one or more audio sensors are not synchronized with the one or more machine vision devices such that the machine vision encounter information and the audio encounter information lack synchronization at the time of recording;

temporally-aligning the machine vision encounter information and the audio encounter information to produce a temporally-aligned encounter recording that synchronizes the machine vision encounter information with the audio encounter information;

generating, by the ACD system, a transcript of the clinical encounter based on the temporally-aligned encounter recording, wherein at least a portion of the transcript is generated by performing visual speech recognition on the synchronized machine vision encounter information;

proactively scanning, by the ACD system, the transcript based on a medical conditions symptoms datasource to identify indications of a specific medical condition, wherein the medical conditions symptoms datasource defines symptoms for various medical conditions;

sending, by the ACD system during the clinical encounter, a message to a participant of the clinical encounter responsive to determining that a number of the indications of the specific medical condition exceeds a threshold, the message recommending that the patient undergo testing for the specific medical condition; and displaying, via a display of the ACD system, a visual representation of the transcript, the visual representation of the transcript identifying portions of the transcript that indicate the specific medical condition.

14. The ACD system of claim 13, wherein the one or more machine vision devices include at least one of:

an RGB imaging system;

an infrared imaging system;

an ultraviolet imaging system;

a laser imaging system;

an X-ray imaging system;

a SONAR imaging system;

a RADAR imaging system; or a thermal imaging system.

15. The ACD system of claim 13, wherein the message recommending that the patient undergo testing for the specific medical condition is a text message sent to an electronic device of the participant.

16. The ACD system of claim 13, wherein the message recommending that the patient undergo testing for the specific medical condition is an audio message.

17. The ACD system of claim 16, wherein the audio message is played through an earbud worn by the participant during the clinical encounter.

18. The ACD system of claim 13, wherein the message recommending that the patient undergo testing for the specific medical condition is displayed via the display of the ACD system.

* * * * *